(12) United States Patent
Fassihi et al.

(10) Patent No.: US 10,166,161 B2
(45) Date of Patent: ***Jan. 1, 2019

(54) PREMATURE INFANT AMNIOTIC BATH INCUBATOR

(71) Applicant: Amnion Life, LLC, Newport Beach, CA (US)

(72) Inventors: Amir Fassihi, Newport Beach, CA (US); Milos Ljubisa Radovanovic, Pozega (RS)

(73) Assignee: Amnion Life, LLC, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/495,383

(22) Filed: Apr. 24, 2017

(65) Prior Publication Data

US 2017/0281444 A1    Oct. 5, 2017

Related U.S. Application Data

(63) Continuation of application No. 15/342,988, filed on Nov. 3, 2016, now Pat. No. 9,662,257.

(Continued)

(51) Int. Cl.
*A61G 11/00* (2006.01)
*A61H 33/00* (2006.01)
*A61G 7/00* (2006.01)

(52) U.S. Cl.
CPC ......... *A61G 11/00* (2013.01); *A61H 33/6005* (2013.01); *A61H 33/6021* (2013.01);
(Continued)

(58) Field of Classification Search
CPC .... A61G 11/00; A61G 11/001; A61G 11/002; A61G 11/003; A61G 11/004;
(Continued)

(56) References Cited

U.S. PATENT DOCUMENTS

| 2,237,177 A | * | 4/1941 | Fischer | ................. | A47K 3/127 |
| | | | | | 4/572.1 |
| 3,025,831 A | | 3/1962 | Berardi | | |

(Continued)

FOREIGN PATENT DOCUMENTS

| CA | 2614632 A1 | 1/2007 |
| CN | 203663028 U | 6/2014 |

(Continued)

OTHER PUBLICATIONS

Partridge, Emily A. "An Extra-Uterine System to Physiologically Support the Extreme Premature Lamb", dated Apr. 25, 2017, Nature Communications, https://www.nature.com/articles/ncomms15112.

(Continued)

*Primary Examiner* — Carrie R Dorna
(74) *Attorney, Agent, or Firm* — Knobbe, Martens, Olson & Bear, LLP

(57) ABSTRACT

Devices, systems, and methods described herein can provide a simulated fluid environment similar to the mother's womb to recreate an ideal or more familiar environment for infants who are born before their ideal due date. In some embodiments, the premature infant amniotic bath incubator can comprise an incubating tank with synthetic or simulated amniotic fluid, a heating element(s), a temperature sensor(s), and/or thermostat(s) for temperature regulation.

26 Claims, 34 Drawing Sheets

Related U.S. Application Data

(60) Provisional application No. 62/252,060, filed on Nov. 6, 2015.

(52) U.S. Cl.
CPC ....... *A61H 33/6068* (2013.01); *A61G 7/0005* (2013.01); *A61H 2201/0207* (2013.01); *A61H 2201/5082* (2013.01)

(58) Field of Classification Search
CPC .. A61G 11/005; A61G 11/006; A61G 11/007; A61G 11/008; A61G 11/009; A61H 33/6005; A61H 33/6021; A61H 33/6068; A61H 2201/0207; A61H 2201/0582
See application file for complete search history.

(56) References Cited

U.S. PATENT DOCUMENTS

| | | |
|---|---|---|
| 4,048,684 A | 9/1977 | Korner et al. |
| 5,459,887 A | 10/1995 | Roman |
| 5,582,574 A | 12/1996 | Cramer |
| 7,186,158 B1 | 3/2007 | Barber |
| 8,292,798 B2 | 10/2012 | California |
| 9,662,257 B1 | 5/2017 | Fassihi et al. |
| 2004/0193096 A1* | 9/2004 | Cooper ............ A61G 10/00 604/19 |
| 2008/0038372 A1* | 2/2008 | Kabayama ......... A61K 33/00 424/663 |
| 2008/0097143 A1* | 4/2008 | Califorrniaa ......... A01N 1/02 600/22 |
| 2013/0316980 A1 | 11/2013 | Tchirikov |

FOREIGN PATENT DOCUMENTS

| | | |
|---|---|---|
| CN | 203988807 U | 12/2014 |
| JP | 2013233194 A | 11/2013 |
| RU | 2140248 C1 | 10/1997 |
| RU | 79420 U1 | 1/2009 |
| RU | 118863 U1 | 8/2012 |
| WO | WO 2013/124086 A1 | 8/2013 |
| WO | WO 2014145494 | 9/2014 |
| WO | WO 2017/079477 | 5/2017 |

OTHER PUBLICATIONS

International Search Report in Application No. PCT/US2016/060388 dated Feb. 27, 2017, in 7 pages.

\* cited by examiner

VARIATION 3:
AC HEATER WITH HEAT EXCHANGER

BATH FLUID PREPARATION - CENTRAL WATER TREATMENT SYSTEM WITH HEATER - C3

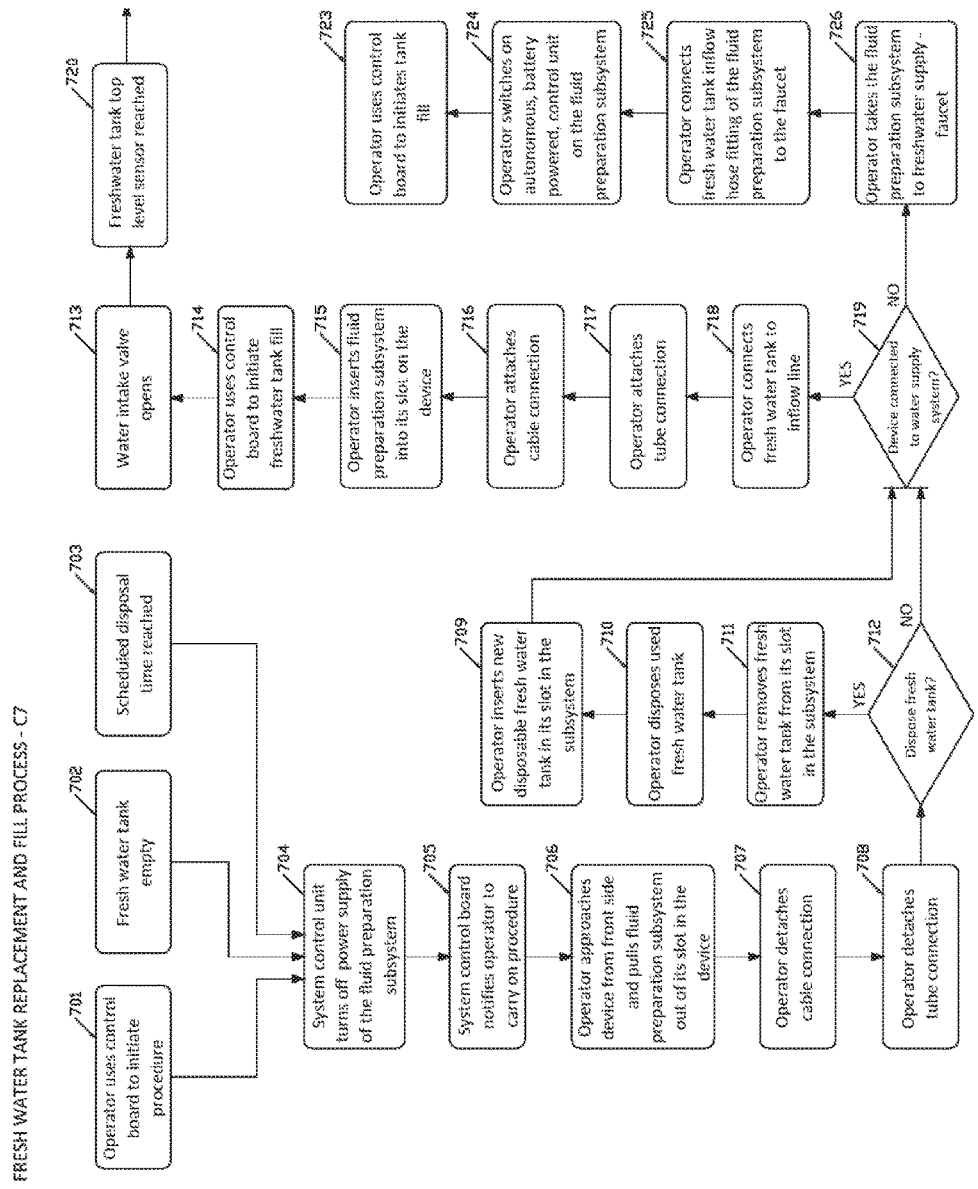
FIG. 26A FRESH WATER TANK REPLACEMENT AND FILL PROCESS - C7

PREMATURE INFANT AMNIOTIC BATH INCUBATOR

CROSS-REFERENCE TO RELATED APPLICATIONS

This application is a continuation of U.S. application Ser. No. 15/342,988, filed on Nov. 3, 2016, entitled "PREMATURE INFANT AMNIOTIC BATH INCUBATOR", which claims the benefit under 35 U.S.C. § 119(e) of U.S. Provisional Application No. 62/252,060, filed Nov. 6, 2015, and entitled "PREMATURE INFANT AMNIOTIC BATH INCUBATOR." Each of the foregoing applications is hereby incorporated herein by reference in its entirety under 37 C.F.R. § 1.57.

BACKGROUND

The systems, devices, and methods disclosed herein relate to the care of infants, and particular prematurely born infants. Preterm birth affects about one of every nine infants born in the United States. This amounts to 400,000 infants each year in the US alone and nearly 15 million globally. Preterm birth is a leading contributor to infant death and the leading cause of long-term neurological disabilities in children. Of those born preterm, 75,464 babies were very preterm, or born before 32 weeks, contributing to the largest number of infant deaths. These infants on average had a length of stay of 46.2 days in the neonatal intensive care unit (NICU).

Care of premature infants generally involves careful control of the environment surrounding the infant. Due to heightened risks of health complications, maintaining body temperature and sterility is of primary importance. Infants in general and preterm infants in particular have relatively large surface area to mass ratios, making them extremely vulnerable to heat loss. They also exhibit thin and poor thermal insulation compared to adults and a small amount of mass to act as a heatsink.

Current methods of care generally include swaddling the infant in warm clothing and providing heating apparatuses. While these apparatuses may adequately warm an infant to some degree, they fail to address issues of dermal desiccation even when humidified air is provided. They may also result in difficulty of movement due to the infant's removal from a fluid environment. Further, difficulties associated with administering medications may arise as well.

There is therefore a need for a premature infant incubator that allows movement and exercise of infant arms and legs within a fluid environment, improves thermal regulation of the infant, and surrounds the infant in a fluid environment. There is also a need for an incubation method that provides transdermal hydration of the infant and transdermal topical nutrition and pharmaceutical treatment for the infant through addition of nutritional and/or pharmaceutical content to the simulated amniotic fluid.

SUMMARY

As such, in some embodiments, the devices, systems, and methods described herein are directed to an infant amniotic bath incubator to address the shortcomings of existing technologies. In some embodiments, a premature infant amniotic bath incubator can comprise an incubating tank with a volume of synthetic or simulated amniotic fluid, a heating element(s), a temperature sensor(s), and/or thermostat(s) for temperature regulation. In certain embodiments, the premature infant amniotic bath incubator can further comprise an inflow channel for adding synthetic or simulated amniotic fluid and/or an outflow drainage channel for removing waste fluid from the bath.

In some embodiments, a neonatal incubator comprises: an amniotic bath comprising synthetic amniotic fluid, wherein the synthetic amniotic fluid comprises one or more electrolytes and one or more minerals, wherein the synthetic amniotic fluid is produced by: installing a cartridge in the neonatal incubator, wherein the cartridge comprises the one or more electrolytes and the one or more minerals; and dissolving contents of the cartridge in purified water; a purified water supply tank configured to provide the purified water for dissolving contents of the cartridge; a waste water removal tank configured to remove waste water from the amniotic bath; and a bath cover selectively attachable to the amniotic bath, wherein the bath cover is sterile and disposable, and wherein the bath cover comprises a safety harness configured to maintain a position of the infant inside the amniotic bath such that a head of the infant is not submerged in the amniotic bath.

In certain embodiments, the neonatal incubator can further comprise a temperature sensor configured to detect a temperature of the synthetic amniotic fluid; and a heater configured to heat the synthetic amniotic fluid when the detected temperature is below a predetermined threshold value. In some embodiments, the purified water supply tank is selectively removable from the neonatal incubator. In certain embodiments, the waste water removal tank is selectively removable from the neonatal incubator. In some embodiments, the waste water removal tank can comprise one or more rechargeable batteries and/or one or more pumps.

In certain embodiments, the synthetic amniotic fluid further comprises albumin. In some embodiments, the cartridge further comprises albumin. In certain embodiments, the synthetic amniotic fluid further comprises glucose and one or more amino acids, wherein the glucose and the one or more amino acids are dissolved in the synthetic amniotic fluid by dissolving contents of a second cartridge, wherein the second cartridge comprises the glucose and the one or more amino acids. In some embodiments, the cartridge can further comprise glucose and/or the one or more amino acids, which can be dissolved in the synthetic amniotic fluid together with other components, such as electrolytes and/or minerals. In some embodiments, the synthetic amniotic fluid further comprises one or more medicines configured to be absorbed by the infant, wherein the one or more medicines are dissolved in the synthetic amniotic fluid by dissolving contents of a second cartridge, wherein the second cartridge comprises the one or more medicines. In some embodiments, the same cartridge can further comprise the one or more medicines, which can be dissolved in the synthetic amniotic fluid together with other components, such as electrolytes and/or minerals. In certain embodiments, the synthetic amniotic fluid comprises a pH level between a range of about 7.5 and about 9.0. In some embodiments, a pH level and osmolality of the synthetic amniotic fluid is modified according to growth of the infant.

In certain embodiments, the neonatal incubator further comprises a synthetic amniotic fluid disposal unit configured to facilitate disposal of stool and the synthetic amniotic fluid to the waste water tank, wherein the synthetic amniotic fluid disposal unit further comprises a stool collector, a bath fluid inflow portion, one or more filters, and a plug unit. In certain embodiments, the neonatal incubator further comprises an adapter seat configured to be coupled to the bath cover, wherein the adapter seat comprises the adapter seat is selected from a plurality of adapter seats, wherein each of the plurality of adapter seats comprises different sizes. In some embodiments, the synthetic amniotic fluid is provided to the bath through a divergent nozzle.

In some embodiments, the neonatal incubator further comprises a fluid sensor configured to be worn around a neck or face of the infant, wherein the fluid sensor is configured to detect presence of fluid in contact with the fluid sensor, wherein detection of presence of fluid in contact with the fluid sensor causes at least a portion of the synthetic amniotic fluid to be automatically removed from the amniotic bath through the waste water removal system. In certain embodiments, the neonatal incubator further comprises an alarm, wherein detection of presence of fluid in contact with the fluid sensor further causes to automatically trigger the alarm. In some embodiments, oxygenation can be provided to the infant through the umbilical cord and/or through extracorporal membrane oxygenation (ECMO) and/or an endotracheal tube deemed safe for submersion. In such embodiments, the infant face and neck can also be submerged in the synthetic amniotic fluid.

In some embodiments, the neonatal incubator further comprises one or more bridges placed over the bath cover. In certain embodiments, the one or bridges are configured to anchor a first end of one or more of a feeding tube, an oxygen tube, cardiac lead wiring, pulse oximeter wiring, and an umbilical cord or catheter over the synthetic amniotic fluid. In some embodiments, a second end of one or more of the feeding tube, the oxygen tube, and the umbilical catheter is connected to the infant.

In certain embodiments, a neonatal incubator for an infant comprises: an amniotic bath comprising synthetic amniotic fluid, wherein the synthetic amniotic fluid comprises one or more electrolytes and one or more minerals, and in some embodiments one or more amino acids, glucose, proteins, and/or pharmaceuticals or other therapeutic agents, wherein the synthetic amniotic fluid is produced by: installing a cartridge in the neonatal incubator, wherein the cartridge comprises the one or more electrolytes and the one or more minerals, and in some embodiments one or more amino acids, glucose, proteins, and/or pharmaceuticals; and dissolving contents of the cartridge in purified water; a purified water supply tank configured to provide the purified water for dissolving contents of the cartridge, for example through use of an internal or external water purification system such as reverse osmosis and/or deionizing exchanger with or without a micro filter or a UV light filter; a waste water removal tank configured to remove waste water from the amniotic bath; and a bath cover selectively attachable to the amniotic bath, wherein the bath cover is sterile and disposable, wherein the bath cover comprises a safety harness configured to maintain a position of the infant inside the amniotic bath such that a head of the infant is not submerged in the amniotic bath, and wherein two peripheral sides of the bath cover are connected by a bridge over the bath, wherein the bridge comprises an anchoring mechanism for anchoring one end of an umbilical cord or one or more catheters, tubes, lines, and/or wiring over the synthetic amniotic fluid. In certain embodiments, the bridge can only be anchored to one side of the bath and its position can be adjusted over the infant through a swiveling mechanism of the anchor to the disposable cover.

In some embodiments, the neonatal incubator further comprises a fluid sensor configured to be worn around a neck or face of the infant, wherein the fluid sensor is configured to detect presence of fluid in contact with the fluid sensor, wherein detection of presence of fluid in contact with the fluid sensor causes at least a portion of the synthetic amniotic fluid to be automatically removed from the amniotic bath through the waste water removal system, such as sufficient to prevent fluid from entering the nasal or oropharyngeal passageways of the infant. In certain embodiments, the bridge is configured to further anchor a first end of a feeding or other tube over the synthetic amniotic fluid. In some embodiments, a second end of the umbilical catheter is connected to the infant.

In certain embodiments, the synthetic amniotic fluid further comprises one or more therapeutic agents, such as medicines configured to be absorbed by the infant, wherein the one or more medicines are dissolved in the synthetic amniotic fluid by dissolving contents of a second cartridge, wherein the second cartridge comprises the one or more medicines. In another embodiment, one or more medicines can be added to the same cartridge comprising electrolytes, minerals, amino acids, and/or glucose, in which contents of a single cartridge can be mixed with purified water.

In some embodiments, a method of incubating an infant comprises: providing a neonatal incubator for the infant, wherein the neonatal incubator comprises an amniotic bath; providing purified water to the amniotic bath; dissolving contents of a cartridge in the purified water to obtain a synthetic amniotic fluid, wherein the contents of the cartridge comprise one or more electrolytes and one or more minerals; placing a selectively attachable bath cover over the amniotic bath, wherein the bath cover is sterile and disposable; placing the infant in the amniotic bath and attaching the infant to a safety harness of the bath cover, wherein the safety harness maintains a position of the infant inside the amniotic bath such that a head of the infant is not submerged in the synthetic amniotic fluid; attaching a first end of an umbilical cord to a portion of the infant submerged in the synthetic amniotic fluid and attaching a second end of the umbilical cord to a bridge over the bath, wherein the bridge is configured to connect one or two peripheral sides of the bath cover over the bath; and periodically adding synthetic amniotic fluid and/or removing waste water from the amniotic bath.

In some embodiments, the method further comprises detecting the temperature of purified or unpurified fluid/water prior to mixing to obtain synthetic amniotic fluid and heating the purified or unpurified water when the detected temperature is below a predetermined threshold value, for example about 37° C. In certain embodiments, after the preheated water is mixed with contents of the cartridge and added to the amniotic bath, the method further comprises: detecting a second temperature of the synthetic amniotic fluid; and heating the synthetic amniotic fluid when the detected temperature is below a predetermined threshold value. In some embodiments, the purified water is provided to the amniotic bath by removing a modular purified or unpurified water tank from the neonatal incubator, adding purified or unpurified water to the modular purified or unpurified water tank, and reattaching the modular purified water tank to the neonatal incubator. In some embodiments, the neonatal incubator can comprise a built-in water purification system. In other embodiments, an external water purification system can be attached and/or used in conjunction with the neonatal incubator. In certain embodiments, the waste water is removed from the amniotic bath by collecting waste water from the amniotic bath in a modular waste water tank of the neonatal incubator, removing the modular waste water tank, emptying the waste water from the modular waste water tank, and reattaching the modular waste water tank to the neonatal incubator.

In some embodiments, the method further comprises dissolving albumin in the synthetic amniotic fluid. In certain embodiments, the method further comprises providing one or more nutrients to the infant by dissolving contents of a second cartridge in the purified water, wherein the contents of the second cartridge comprise glucose and one or more amino acids. In some embodiments, the cartridge can further comprise glucose and/or the one or more amino acids, which can be dissolved in the synthetic amniotic fluid together with other components, such as electrolytes and/or minerals. In some embodiments, the method further comprises administering one or more medicines to the infant by dissolving contents of a second cartridge in the purified water, wherein the contents of the second cartridge comprise the one or more medicines. In some embodiments, the same cartridge can further comprise the one or more medicines, which can be dissolved in the synthetic amniotic fluid together with other components, such as electrolytes and/or minerals.

In certain embodiments, the method further comprises attaching a necklace around a neck of the infant, wherein the necklace comprises a fluid sensor, wherein the fluid sensor is configured to detect presence of fluid in contact with the fluid sensor. The sensor need not necessarily be a necklace, but can be otherwise operably attached to the head or neck, such as via an adhesive bandage for example. In some embodiments, the method further comprises automatically removing at least a portion of the synthetic amniotic fluid from the amniotic bath when the fluid sensor detects presence of fluid in contact with the fluid sensor. In certain embodiments, the method further comprises attaching a first end of a feeding tube to the infant and attaching a second end of the feeding tube to the bridge.

For purposes of summarizing the invention and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the invention may be embodied or carried out in a manner that can achieve or optimize one advantage or a group of advantages without necessarily achieving other objects or advantages.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

FIGS. 26A-B are block diagrams depicting one or more embodiments of replacing and/or filling a fresh water tank of an amniotic bath incubator system for premature infants.

DETAILED DESCRIPTION

Figure 1:
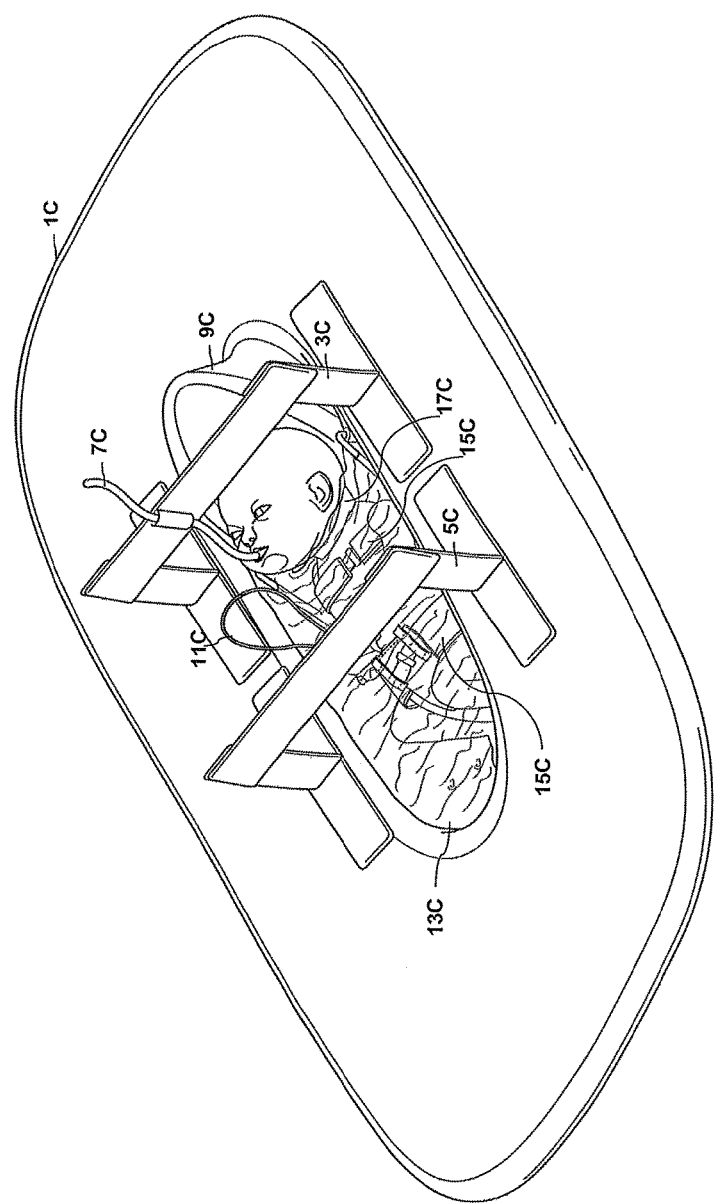
FIG. 1 illustrates a perspective view of an infant placed inside an embodiment of an amniotic bath incubator.

The devices, systems, and methods described herein relate in some aspects to neonatal incubators, and more specifically to amniotic bath incubators for mammals, such as infants including premature infants, preterm infants, and/or low birth weight term infants, including veterinary applications. In some embodiments, the incubators could be utilized for non-neonates, such as, for example, hypothermic or otherwise ill children or adults in some cases. Some embodiments of the devices, systems, and methods described herein can have several significant benefits for such infants compared to the currently existing technologies of convection and radiant-based incubators. Not to be limited by theory, some of such benefits can include, for example, one or more of the following: (1) improved thermoregulation, (2) improved hydration through reconstitution of the in-utero intramembranous pathway of fluid absorption, (3) provision of a fluid environment for exercise and movement of appendages of the infant, and (4) providing of a more natural environment for skin development. Some advantages of the devices, systems, and methods described herein are discussed in more detail below.

Improved Thermal Regulation

Immediately upon birth, fetal reliance on the maternal heat reservoir ceases and a wet infant is born into a relatively cold and hostile environment. Preterm infants, among others, have several significant disadvantages compared to term infants for heat regulation and improved thermoregulation is a significant challenge in NICUs. Preterm infants have little insulating subcutaneous fat compared to term infants making them far more susceptible to heat loss. In addition, preterm infants have very thin skin leading to significant transepidermal water loss and evaporative heat loss. The thin keratinized layer can be completely absent in infants until the 26th week making their skin permeable to water. Evaporative heat exchange can reach 50 W/m$^2$ in preterm infants compared to 5 W/m$^2$ in term infants. In infants born very prematurely, such as at 25-27 weeks, evaporative heat loss can be, in some cases, the most important mode of heat loss for more than 10 days after birth. In addition, preterm infants can have blood vessels close to skin, leading to an increased rate of heat loss.

In addition, preterm infants can have excessive amounts of evaporative heat loss due to a greater surface area to volume ratio which compared to adults can be up to three times the ratio for infants of 1500 g and up to six times the ratio for extreme preterm infants of 500 g. Because of the lack of significant insulating subcutaneous fat, heat can be more easily lost from internal organs to skin leading to more rapid decrease in internal temperature. Overall, the rate of heat loss in newborns immediately after birth can be estimated at 33 to 47 kcal/kg/min and preterm infants are at the highest risk for heat loss.

In addition to their increased risk for heat loss, preterm infants can also have very poor mechanisms for body temperature regulation and can be far more limited than term infants in generating heat. Preterm infants can lack the shivering mechanism used to maintain body temperature. In addition, a term infant's reaction to rapid temperature fluctuations upon birth can include increased voluntary muscular activity which can be mostly absent in very preterm infants. Brown fat used for non-shivering thermogenesis can be significantly more limited in preterm infants, and thus more calories intended for natural growth are diverted to heat generation.

Thus protecting infants from heat loss and providing appropriate thermoregulation can be one of the most important goals in the NICU. Improved thermoregulation can increase preterm infants' chances of survival, reduce infants' need to perform heat producing metabolic work using energy intended for growth and development, and eliminate problems and complications associated with rewarming of cold infants.

In intrauterine life, a fetus can be thermoregulated within the amniotic fluid with a fetal temperature of approximately 0.5° C. higher than the maternal temperature due to the natural fetal heat production. However upon premature birth, a preterm infant can be exposed to air in the nursery which can be very cold compared to the environment previously experienced in-utero. In addition, skin can be initially covered with amniotic fluid causing rapid heat loss due to evaporation. This can be followed by thermogenic responses by the infant to increase basal heat production.

Temperature loss in a preterm infant can be related to the temperature and humidity of the environment air (delivery room/NICU), the flow velocity of surrounding air from nursing and examination, temperature of surfaces facing the infant (incubator walls/bedding material), and the temperature of surfaces in contact with the infant.

Not to be limited by theory, thermal response in infants prematurely exposed to a cold nursery environment is generally mediated primarily through the sympathetic nervous system and release of norepinepherine. Preterm infants often lack the shivering mechanism of term infants. The earliest response to the sympathetic nervous system can be vasoconstriction in deep dermal layers, thus reducing blood flow to the skin creating insulation between the core and the environment. However, the reduced subcutaneous fat in preterm infants can diminish this effective insulating property. Glycolysis (breakdown of sugar) stimulated from epinephrine release can also be a source of heat generation for preterm infants. This response can not only have deleterious effects in breakdown of calories otherwise intended for growth, but also may result in periods of transient hyperglycemias. Brown fat can provide a source of non-shivering thermogenesis in newborns. Abundance of mitochondria in these cells can break down triglycerides into metabolic acids producing heat and increasing metabolic activity by two to three folds. However, preterm infants can have little to no brown fat and may not be capable of any more than a 25% increase in metabolic rate despite the most severe cold stress. Control of voluntary muscle tone, flexion, posture, and increased motor activity may serve to augment heat production in skeletal muscle, but this mechanism can be limited in preterm infants because of underdeveloped musculature. Overall, a preterm infant's thermoregulatory reaction and maintenance of core temperature in response to extra-uterine exposure to cold environment can mainly be at the expense of metabolically generated heat. In addition, an infant's reaction to cold stress can have significant repercussions for normal development, not only in terms of caloric loss which otherwise would be intended for growth and development but insults to normal development associated with infant's response to cold stress such as periods of high epinephrine release and periods of transient hyperglycemia.

Studies have shown deleterious differences in preterm infants nurtured in dry, ambient air environments in minimally different temperatures of 35° C. and 36.5° C. in the first week of life. Rectal temperatures were shown to be the same, but significant difference in weight gain was seen with warmer infants concluding that thermogenic response in slightly cooler infants was sufficient to consume considerable enough calories otherwise used for growth.

Current practice upon birth generally includes drying of the infant in the delivery room to decrease evaporative heat loss and bundling or swaddling of infants to decrease exposure to cold air followed by placing newborn on mother's arms and chest (kangaroo care). These steps, however, are inadequate in preterm infants. Preterm infants instead are generally placed initially on radiant warmers to allow examination and intervention by medical staff. Once the preterm infant is stable, they are placed in a convectively warmed incubator enclosure with an air temperature of 36-37° C. with variety of swaddling heat shields. There are significant shortcomings, however, in preterm infant thermoregulation.

Current convection warmed incubators generally comprise a plastic hood over the infant with access ports or hand holes to minimize air flow. Abdominal skin surface temperature detectors can be used to regulate incubator heating in nurseries. Artificial humidification inside the incubator hood can be used to decrease evaporative heat loss. However, there are significant disadvantages with convection incubators. Humidification levels of greater than about 50% can be associated with risks of bacterial colonization, pseudomonas infections in preterm infants, sepsis and death. Incubator ports and doors can be opened and closed once an hour in some nursery situations, which makes it very difficult to maintain homeothermy in critically ill patients due to a constant need to access the patient for management. Temperature regulation for the smallest infants in a convection incubator in the first few days can also be very difficult because of the rapid drops in temperature as the incubator doors are opened to care for the infant. In addition, the entry of cool air followed by overdamping of the servo-control system on infant skin can lead to overshoot and undershoot of mid-hood incubator air temperature for up to one hour after the door has been closed. These temperature insults for over or under thermal neutral temperature may become part of infant's routine experience during intensive care. In addition, incubator designs may not warm adequately a very low birth weight infant of, e.g., less than 1 kg particularly early in life when evaporative losses are extremely high.

Current convection incubators generally attempt to minimize air flow velocity, increase air temperature, increase water vapor pressure and humidity, and maintain adequate wall temperature on the incubators. Studies of environment and climate control however have shown that airflow velocities, capacity for humidification and wall temperatures on incubators can vary considerably between different incubators.

Use of radiant warmers which is an alternative current technology also has significant shortcomings in thermoregulation. Radiant heaters placed over an open bed provide good accessibility and visibility for care but can lead to extensive heat losses through evaporation and convection.

Radiant warmers generally comprise an electrically heated metal alloy wire coiled within a quartz tube. Metal alloys can emit wavelengths in middle portion of infrared spectrum (1000 nm to 3000 nm). Surrounding quartz enveloping the coils can absorb the infrared energy and re-emit electromagnetic radiation in longer wavelengths (>3000 nm). At full power, some of infrared irradiance can be less than 100 mW/cm$^3$ and near infrared irradiance at or near 10 mW/cm$^3$. Under a radiant warmer, an infant can have significant convective and evaporative heat loss which can be replaced in a non-homogeneous fashion by the radiant warming element located above the infant. Thus, some body parts can be heated out of proportion to others. In addition, evaporative heat loss can be significantly higher in moderately preterm and very preterm under radiant heater compared to convection incubators. Insensible evaporative water loss can be up to 3.5 ml/kg/hr in incubators and up to 7 ml/kg/hr under radiant warmers for infants less than 1 kg. Insensible evaporative water loss can become similar to convection incubators for infants greater than 1 kg. The limitation of radiant warmers for thermoregulation is evident in detection of, e.g., up to 8.8% increased metabolic rate secondary to increased oxygen consumption seen in infants under radiant warmers compared to convective incubators, indicating additional burden on normal growth and development.

Other methods for thermoregulation in infants can include kangaroo care using skin to skin contact with the mother or father. However, this technique can be inadequate in preterm infants. Rigid plastic body hoods as heat shields, hybrid incubator/radiant warmer design, occlusive plastic blankets and bags, use of water filled mattress, semiocclusive artificial skin made of polyurethane dressings and petroleum emollient have also been tried but can be inadequate in very preterm and extremely preterm infants.

Despite all the efforts which currently consist of quickly drying the infant, placing infant under radiant warmer in the delivery room, convective incubation during transport, use of plastic bags over the infant and other measures taken, extremely low birth weight infants of less than 750 g can routinely become hypothermic and can be prone to excessive transepidermal evaporative and convective heat loss. Further, the rate of rewarming the infant can also have complications and risks for developing infants.

In contrast, some embodiments of the devices, systems, and methods relating to neonatal and/or amniotic bath incubators as described herein can provide significantly improved thermoregulation for infants by providing a fluid environment with constant and uniform temperatures.

Improved Hydration

Not to be limited by theory, in addition to thermoregulation, another benefit of some of the embodiments described herein can relate to improved hydration of the infant through the intramembranous pathway. In near term sheep, an average of 200-250 ml/day of water is generally absorbed from the amniotic sac directly into fetal blood. Similarly in humans, a significant pathway for absorption of amniotic fluid by the fetus through diffusion of fluid across the fetal skin back into fetal circulation has been observed and can be calculated at 200-500 ml/day near term. This pathway of absorption of water is generally referred to as the Intramembranous Pathway. Fluid constantly absorbed by the fetus can be mostly urinated and circulated back into the amniotic sac. Upon preterm birth, this pathway of circulation of water can immediately cease and the underdeveloped skin can be exposed to a harsh and dry environment of a nursery, where not only the intramembranous pathway of absorption of fluid is halted, but can be reversed through tremendous evaporative loss.

In utero, there can be a free flow of fluid across the skin and into the fetal plasma until the 26th week of gestation due to lack of development of the keratinized layer (intramembranous pathway). Fetal skin and the umbilical cord can be freely permeable to water and solutes, allowing rapid bidirectional diffusion across the non-keratinized layer. Keratinization of skin can begin at the 20th week and can be completed by the 26th week. Prior to this, an amniotic fluid can serve both as a physiologic buffer and an extension of the fetal extracellular compartment. Stratum corneum, which is responsible for epidermal barrier function does not become functionally mature in the fetus until 32 weeks gestation. However, acceleration of the skin maturing process can occur after birth and exposure to air and most extremely premature infant can develop an epidermal barrier by approximately 2 weeks of postnatal age. Overall, however, the skin of infants born 23 to 26 weeks' gestation is generally extremely immature and can be ineffective as an epidermal water barrier. This can lead to disturbances in temperature regulation, water balance and breakdowns in skin integrity.

Premature infants who are less than about 30 weeks gestational age can exhibit water loss of as much as 15 times greater than that of full-term infants because of their immature stratum corneum. Losses ranging from 40 to 129 ml/kg/day or more have been reported. Some have estimated premature infant water loss at 26 weeks gestation or less in the first 48 hours after birth at 60 g of water/m$^2$/hr or greater than 180 ml/day.

This fluid loss can also leads to additional calorie burden of approximately 0.6 kcal/ml lost through latent heat evaporation. Thus, an extremely premature infant may lose 100 kcal/kg/day simply through evaporation from the skin. Premature newborns 23-24 weeks gestational age may lose as much as 13% of body weight as transepidermal water loss during the 1st day of life, even at an ambient humidity of 50%.

Current medical practice generally does not provide for reconstitution of the intramembranous pathway, but rather aims to reduce trans-epidermal evaporative water loss (TEWL). Currently in nurseries this approach is generally done through increasing the relative humidity surrounding the infant. TEWL generally depends on the ambient water vapor pressure, irrespective of whether the infant is under a radiant warmer or in an incubator. Raising the ambient humidity can increase water vapor pressure and decrease fluid and heat loss through evaporation. Because of high trans-epidermal fluid losses in these infants, intravenous solution containing 5% to 10% dextrose is generally started as quickly as possible after birth. Other strategies to reduce TEWL and prevent extreme heat and fluid losses in premature infants younger than 30 weeks gestational age can include transparent adhesive dressings and coating the skin with emollients. Transparent adhesive dressings can be used to prevent excessive skin water losses in premature. TEWL can be reduced by as much as 50% by the creation of this second skin. However significant amount of skin trauma can occur upon their removal. Smaller epidermal water loss can also be shown with emollient ointments.

The intramembranous pathway of circulation of water in humans is generally driven by osmotic differences between the amniotic fluid and the fetal serum. A low amniotic fluid osmolality can provide a large potential osmotic force: for example about 19.3 mm Hg for each mOsm/kg gradient in osmolality across fetal skin. Artificial alteration of the osmolality and oncotic pressures of amniotic fluid has revealed that intramembranous flow can be highly correlated to osmotic differences. In animal studies, direct infusion of saline into amniotic fluid on long term basis in pregnant sheep has shown to increase fetal hydration. Injection of 1.5 L of warm distilled water into pregnant sheep amniotic fluid has shown significant absorption of fluid into fetal circulation leading to decrease in fetal osmolality, plasma electrolytes, fetal heart rate and increase in arterial pressure and fetal hemolysis showing intramembranous pathway (across the skin) as a major route of water absorption as a result of sudden change of amniotic fluid to a hypotonic solution.

Some embodiments of the devices, systems, and methods of an amniotic bath incubator as described herein can provide for improved hydration to preterm infants or term infants by reconstituting the intramembranous pathway. To do so, in certain embodiments, a synthetic or simulated amniotic bath in which an infant is placed in can comprise a low osmolality to facilitate absorption thereof by the infant through the skin.

Supporting Musculoskeletal Development

Not to be limited by theory, in addition to thermoregulation and improved hydration, another benefit of some of the embodiments described herein relates to providing a better physiologic environment for musculoskeletal movement and development. In-utero, a fetus floats in an environment of amniotic fluid with near-zero gravity, which can provide room for active movement and musculoskeletal exercise leading to normal muscle tone at term. Muscle tone can be a major factor in how a preterm baby's motor skills develop. A full-term infant with normal muscle tone can keep itself in a nicely flexed position with arms and legs tucked into the body. A preterm infant, on the other hand, often has less muscle bulk and is usually hypotonic, making it difficult for the infant to achieve flexed positions. The infant can have difficulty resisting gravitational force, which is physiologically absent in the in-utero fluid environment for a fetus at this stage of development. Often, a preterm infant, unable to flex properly, may end up in frog-like posture or other postures for prolonged periods of time. These prolonged exposures to gravity can deprive the preterm infant of normal movement and exercise and thus can interrupt the infant's normal musculoskeletal growth and development.

When preterm infants are weak and hypotonic, especially through the trunk, they can still attempt to gain some control by flexing or stiffening their muscles. They may arch their head, neck and trunk. They may lift their shoulders, make fists with their hands, and/or stiffen their legs and point their toes. Only as they grow stronger and get more control through the trunk, these other areas will start to relax. Preterm infants have been shown to exhibit motor delay when compared with their full-term peers, and also have also been shown to have some atypical postures, e.g. hyperextension of the neck and the trunk and reduced active flexion power when compared with their full-term counterparts. These atypical postures are commonly believed to be caused due to the loss of physiological flexion from premature birth and reinforcement of extended postures as a result of medical procedures in the intensive care unit.

Not to be limited by theory, physiologically, while the primary development of muscle tissue can occur prior to term, differentiation of muscle fibers is considered incomplete until 40 weeks post-conception. Infants entering neonatal intensive care settings at 24 weeks' postconceptional age (PCA) can have incomplete development in muscle tissue, extremity flexor tone, articular structures, skulls, and spinal curvatures. These immature structures can contribute to vulnerability for postural and skeletal malalignment. Early preterm infants born in less than 32 weeks are more likely to have delays in fine and gross motor functioning. Flexor tone in the extremities of preterm neonates can begin in the legs at 30 to 32 weeks' PCA and in the arms at 36 weeks' PCA.

Studies of young adults examined at 14 and 23 years of age, who were born at very low birth weights (VLBW) of less than 1500 g, have shown diminished manual dexterity, reduced balance and reduced speed in gross motor skills. Overall, VLBW young adults showed poorer fine and gross motor skills compared to a control group. Longitudinal findings indicate that many VLBW children do not outgrow their motor problems even after entering adulthood. At the preschool age, prevalence of developmental delay in moderate preterm infants born between 32-35 weeks gestation was about twofold compared to full-term infants and about one-half compared to early preterm infants.

Some of the embodiments described herein can prevent such results by providing an infant with a more physiologic and natural environment for development and movement of the arms and legs. In certain embodiments, unlike convection incubators or radiant warmers, appendicular skeleton is no longer exposed to 1 G gravity or bundled/swaddled in blankets, thereby removing such obstacles to musculoskeletal development. The low gravitational fluid environment of less than 1 G in some embodiments can allow a pre-term infant to continuously move and exercise its appendicular skeleton similar to the in-utero environment, thereby providing better support for musculoskeletal development and growth for the infant.

Supporting Skin Development

Not to be limited by theory, another benefit of some of the amniotic bath incubator systems, devices, and methods described herein can relate to improved skin care and related protective advantages of fluid submersion.

Skin breakdown of premature infants can generally occur due to a variety of causes, including trauma from adhesive removal, infection, friction, pressure sores from prolonged bedrest, and diaper dermatitis. The degree of skin breakdown can range from surface excoriations to full thickness wounds involving the dermis. Further, cutaneous manifestations often may precede systemic bacterial or fungal disease. Invasive fungal dermatitis is generally recognized as an early form of fungal disease in extremely low-birth-weight infants.

Existing methods of care can involve use of various emollients to improve skin integrity. Further, use of soft bedding and water mattresses has become one method of attempting to prevent pressure points on the skin. Moreover, periodic moistening of wounded tissue every 4-6 hours can aid the healing process, whereas drying can impede the migration of cells. However, such methods all have their shortcomings.

Further, diaper dermatitis can be a significant risk, especially in pre-term infants. Diaper dermatitis can have a number of causes in infants and can affect the perineum, groin, thighs, buttocks, and anal regions. As the pH of the skin rises when exposed to urine or stool, the skin can become more vulnerable to injury and penetration by microorganisms. An alkaline pH can activate fecal enzymes, such as protease and lipase, which can break down protein and fat, building blocks of the stratum corneum, and also activate bile salts that can cause injury. This can be a primary mechanism for direct contact dermatitis from exposure to stool.

Skin breakdowns and injuries can be a significant cause of morbidity in neonatal intensive care setting. Skin injuries can lead to discomfort and pain, infections, sepsis and death. A dry environment in which a preterm infant is exposed to is suboptimal in maintaining a hydrated and healthy skin developing rapidly to prepare itself for the dry environment. As such, some of the embodiments herein provide a fluid environment to provide improved hydration to the skin as well as prevent pressure injuries to the skin of preterm infants.

Overview

As discussed, devices, systems, and methods described herein can provide a simulated fluid environment similar to the mother's womb to recreate a more familiar environment for infants, including infants born before their ideal due date, low birth weight term infants, and/or normal birth weight term infants during the first 24 or 48 hours. The devices, systems, and methods described herein can provide for improved thermoregulation, comfort, and hydration for pre-term, term, and/or older infants. One or more such advantages, such as thermoregulation, can be particularly important before, during, and/or after surgical procedures. In some embodiments, an amniotic bath incubator can comprise an incubating tank with synthetic or simulated amniotic fluid, a heating element(s), a temperature sensor(s), and/or thermostat(s) for temperature regulation. An infant or premature infant can be placed in the incubating tank to provide a thermo-regulated fluid environment to the infant, in which the fluid can be made similar to physiologic amniotic fluid. For example, the osmolality, electrolyte and mineral content of the synthetic or simulated amniotic fluid in which the infant is placed can be similar to those of physiologic amniotic fluid.

The physiologic amniotic fluid in the mother's womb is the protective liquid bathing the fetus during pregnancy and serves as a heat reservoir for thermoregulation and a reservoir for absorption of water by the fetus through the intramembranous pathway. It also provides an environment for fetal movement and comfort while maintaining a steady temperature of 37 C for the developing infant. Amniotic fluid contains electrolytes, minerals, proteins, peptides, lipids, lactate, pyruvate, enzymes, hormones and amniotic stem cells.

As such, in some embodiments, the temperature of the synthetic or simulated amniotic bath is regulated by use of one or more temperature sensors and/or heaters to maintain a temperature of about 37° C. for the infant. The synthetic or simulated amniotic fluid can also comprise one or more electrolytes, minerals, proteins, peptides, lipids, lactate, pyruvate, enzymes, hormones and amniotic stem cells.

FIG. 1 illustrates a perspective view of an infant placed inside an embodiment of an amniotic bath incubator. In some embodiments, an infant or preterm infant sits in the simulated or synthetic amniotic fluid 13C. For example, the infant or preterm infant can be placed in the synthetic amniotic fluid 13C up to its sternal notch, or neck in some embodiments.

System/Device Components

Figure 2:
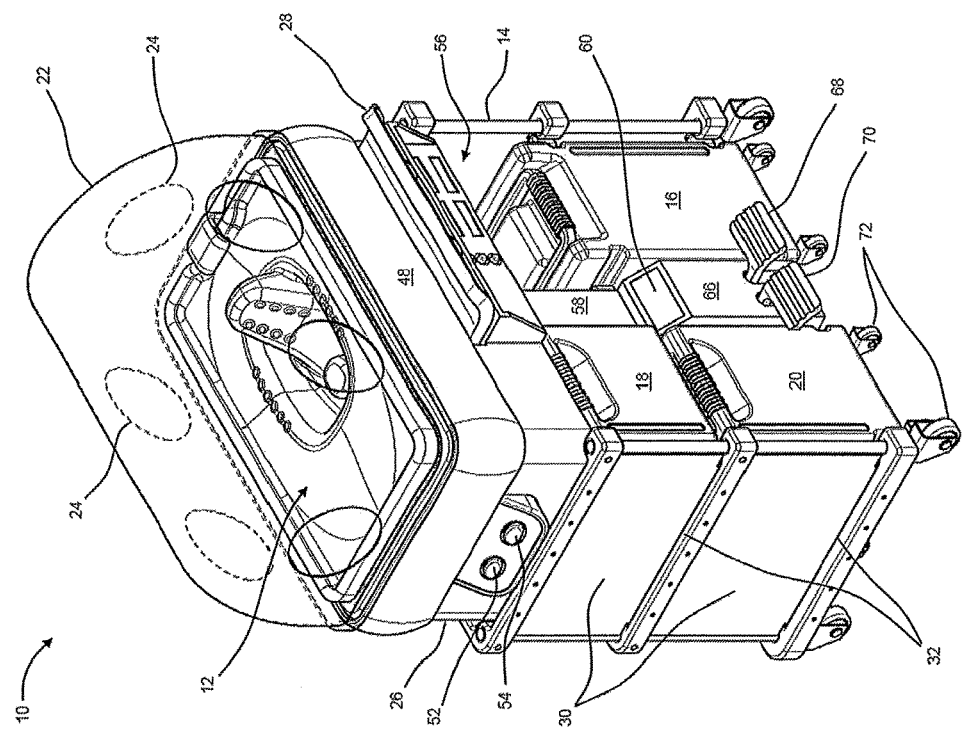
FIG. 2 illustrates a perspective view of an embodiment of an amniotic bath incubator for premature infants.

FIG. 2 illustrates a perspective view of an embodiment of an amniotic bath incubator for premature infants. Referring to FIG. 2, in some embodiments, a neonatal incubator 10 for term and preterm infants accommodates the infant's body and extremities submerged in synthetic amniotic fluid 94, thereby creating a womb-like condition for the infant. The incubator 10 can comprise a bath 12 for holding the infant and the synthetic amniotic fluid 94.

In some embodiments, the bath 12 can be supported on a frame 14, which can also house a fresh fluid reservoir 16, a waste fluid primary tank 18, and/or a waste fluid secondary tank 20. In certain embodiments, to conserve heat and preserve the synthetic amniotic fluid 94 when the infant is placed in the bath 12, a dome 22, preferably made of a clear material such as acrylic glass, covers the bath 12. One or more sleeve ports 24 may be incorporated into the dome 22 for accessing and manipulating the infant from a variety of positions while maintaining the dome 12 over the infant.

In some embodiments, the frame 14 can comprise a support 26, incorporating functions for dispensing water and synthetic amniotic fluid 94, and/or a sliding shelf 28. The frame can also comprise panels 30 to protect the reservoir 16, the primary tank 18 and secondary tank 20, and guides 32 that interface with the reservoir 16 and the primary and secondary tanks 18, 20 to preserve their orientation relative to the frame 14.

Figure 3:
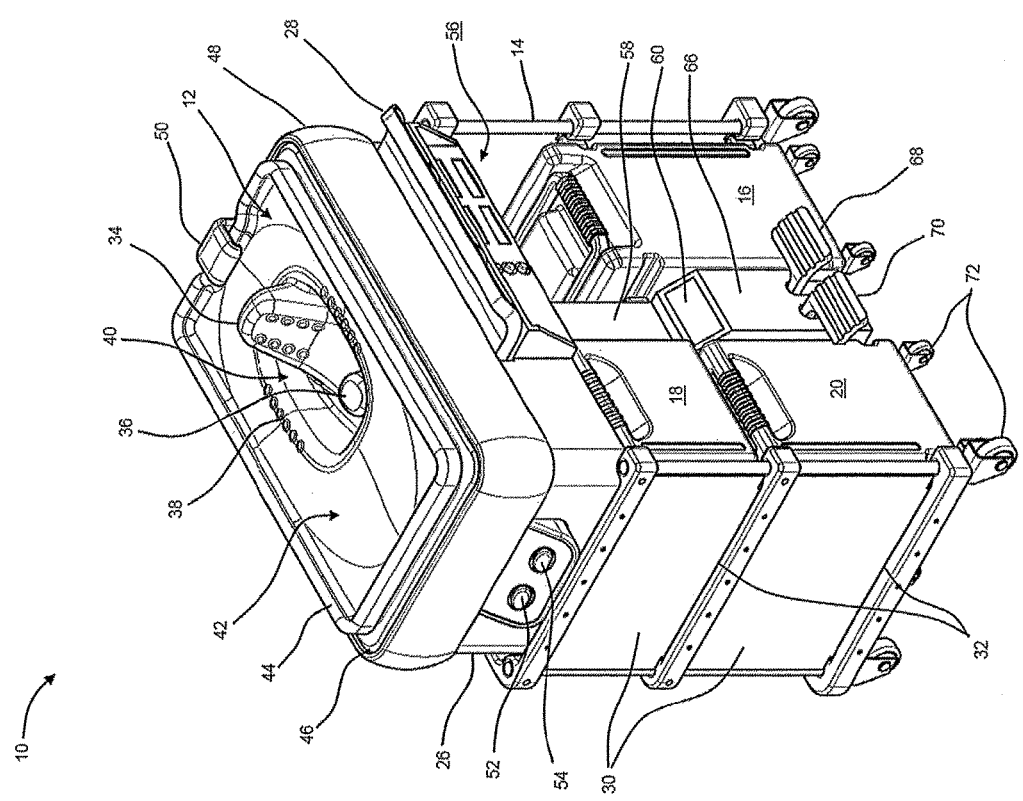
FIG. 3 illustrates a perspective view of an embodiment of an amniotic bath incubator for premature infants with the dome removed.

FIG. 3 illustrates a perspective view of an embodiment of an amniotic bath incubator for premature infants with the dome removed. Referring to FIG. 3, the incubator 10 of an embodiment is shown with the dome 22 removed. In some embodiments, the bath 12 comprises a seatback 34 and/or a post 36 for holding the infant in a comfortable position. The seatback 34 and/or post 36 can be located in a sump portion 40 of the bath 12, which can be surrounded by a shallow portion 42. The shallow portion 42 can be bordered by a raised rim 44.

In certain embodiments, a gutter 46 catches any synthetic amniotic fluid 94 escaping over the raised rim 44. A bumper 48 can surround the bath 12 to suppress jarring vibrations if the incubator 10 inadvertently strikes a surface when moved. The bath 12 can be filled via a spout 50 extending over the raised rim 44, and temperature can be maintained using a heating element within the bath 12. The bath can also incorporate a drain in the sump portion 40 for draining the bath 12. In some embodiments, some or all internal pipes and/or tubes or a portion thereof of the amniotic bath incubator system comprise only negative angles to facilitate natural draining of residual fluid to the wastewater tank to reduce risk of colonization with bacteria.

In some embodiments, the spout 50 is operated using a water control 52 and/or an amniotic fluid control 54. The water and amniotic fluid controls 50, 52 can be located on the support 26, although they may be repositioned according to preference and design. Additional controls 56 can be included for other purposes, such as draining the bath 12, heating, maintain temperature, cooling/heating the bath, adding purified water, dissolving one or more cartridges, etc. In certain embodiments, one or more controls, including the water and/or amniotic fluid controls 50, 52 can be located on a device separate from the amniotic bath, in which the one or more controls can be configured to electronically communicate with one or more components of the amniotic bath. For example, the one or more controls can be part of a single device that is configured to control one or more functions of a plurality of amniotic bath incubators. As such, an operator may be able to control one or more functions of a plurality of amniotic bath incubators at once from a single location. The one or more functions can include, for example, changing or rinsing the bath fluid, preparing the bath fluid, disinfection, discharging wastewater, replacing fresh water, or any other feature described herein. In addition to the guides on the frame 14, an upper central panel 58 may be located between the reservoir 16, and the primary and secondary tanks 18, 20, to help orient them and preserve their position relative to the frame 14. A sensor readout 60 positioned under the upper central panel 58 can include data about the condition of the incubator 10 and synthetic amniotic fluid 94.

Figure 4:
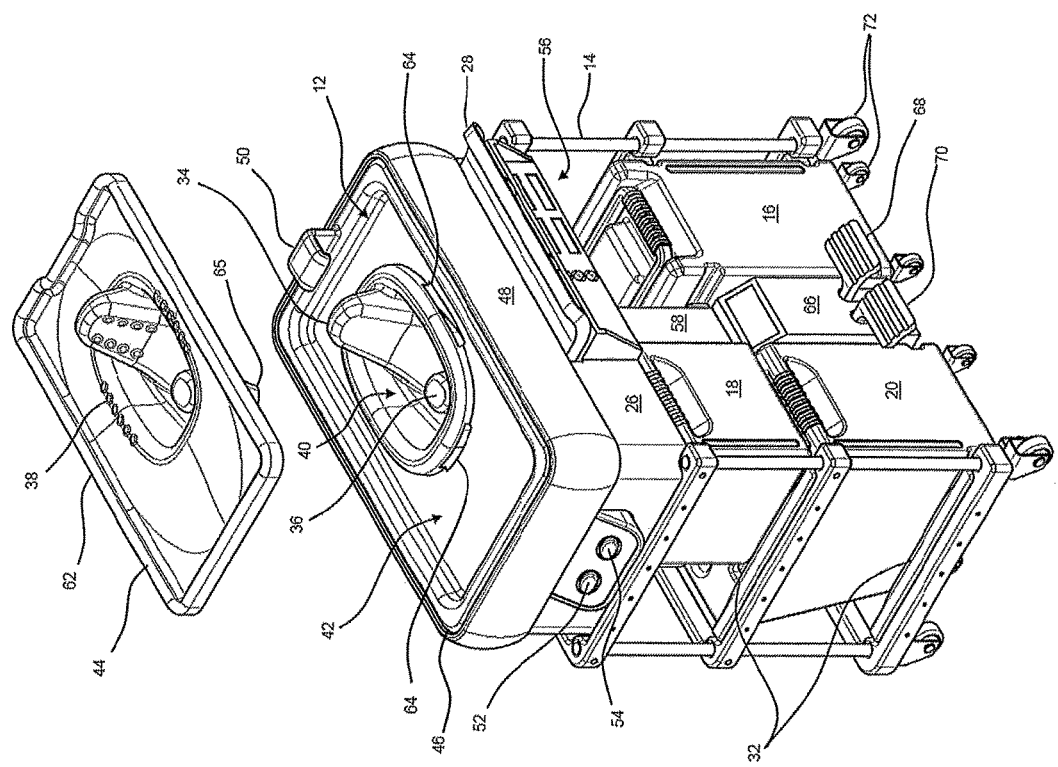
FIG. 4 illustrates a perspective view of an embodiment of an amniotic bath incubator for premature infants with a dome and cover removed.

FIG. 4 illustrates a perspective view of an embodiment of an amniotic bath incubator for premature infants with the dome removed. Referring to FIG. 4, the bath 12 may incorporate a removable cover 62. In some embodiments, the cover 62 can conform to the shape of the bath 12, its sump portion 40, seatback 34 and/or post 36, as well as the shallow portion 42 comprising the raised rim 44, and be pre-formed in the aforementioned shape in some cases. In certain embodiments, the cover 62 may constitute the raised rim 44, and/or surface features 38 for stimulation. In order to prevent any synthetic amniotic fluid 94 from becoming trapped under the cover 62, the bath 12 may include one or more drain ports 64 leading to the primary waste tank 18. The cover 62 can primarily drain through a conforming drain aperture 65, which can conform to the drain at the bottom of the sump portion 40 of the bath 12.

With the seatback 34 and/or post 36, the bath 12 can be formed similar to an infant seat and may be made in different sizes for different sized infants to allow comfortable positioning of the infant in a near seated position, allowing the infant's head to be comfortably positioned above the fluid level to allow oral nutrition and airway oxygenation. The sizes can correspond to differences in height and weight of preterm and term infants. In some embodiments, the system can comprise a plurality of covers 62 of varying sizes. The plurality of covers 62 of varying sizes can each comprise configurations of a seatback 34 and/or post 36 of varying sizes to accommodate infants of different sizes. As such, an operator may be able to select a particular cover 62 comprising a seatback 34 and/or post 36 of particular size(s) to fit a particular infant. Likewise, different covers 62 of varying sizes may be used replaced and used for the same infant as the infant grows.

The cover 62, like the bath 12 can be sterile and also made in different seat sizes fit for the tank and infant seat. Specifically, the cover 62 can be made of a medically inert material that may include antibacterial and antifungal properties, and a safety strap to prevent accidental submersion. A conforming drainage aperture 65 that aligns with the outflow channel of the sump portion 40 can be opened and closed using a stopcock or another similar mechanism to refill the cover 62 with synthetic amniotic fluid 94 when reusing the cover 62 as clinically indicated. The sterile synthetic amniotic fluid 94 with or without additional medications or nutrients can enter the reservoir through the spout 50. Alternatively, separately from the incubator 10, it may be poured into the cover 62 using piping or a shower attached to inflow piping.

In some embodiments, the sensor readout panel 60 can be located on a lower central panel 66. The sensor readout panel 60 can be located on any other portion of the amniotic bath incubator. In certain embodiments, the sensor readout panel 60 can be located on another device separate from the amniotic bath incubator, in which the separate device is configured to electronically communicate with one or more components of the amniotic bath incubator. For example, a user interface, such as a smartphone, tablet, laptop, or other computer display, may be configured to display one or more sensor readouts. The lower central panel 66 can include a reservoir release pedal 68 and/or a wastewater release pedal 70, keeping the reservoir 16, the primary tank 18, and the secondary tank 20 in position when the incubator 10 is moved. In some embodiments in which the reservoir 16 and the secondary tank 20 are on casters 72, they can roll out from under the frame 14 for disposal and/or refilling operations.

Figure 5:
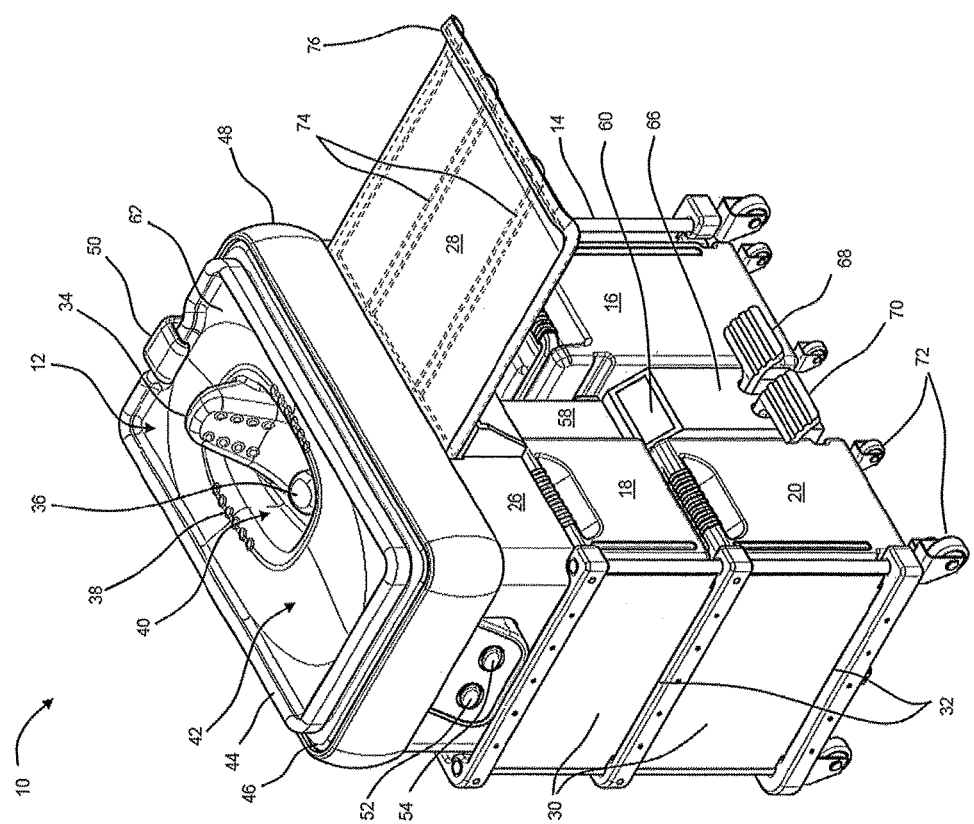
FIG. 5 illustrates a perspective view of an embodiment of an amniotic bath incubator for premature infants with a changing panel extended.

FIG. 5 illustrates a perspective view of an embodiment of an amniotic bath incubator for premature infants with a changing panel extended. Referring to FIG. 5, the incubator is shown with the sliding shelf 28 extended. The sliding shelf 28 can comprise one or more support ribs 74 allowing it to hold substantial weight. A raised lip 76 can help prevent objects from rolling or sliding off the sliding shelf 28.

Figure 6:
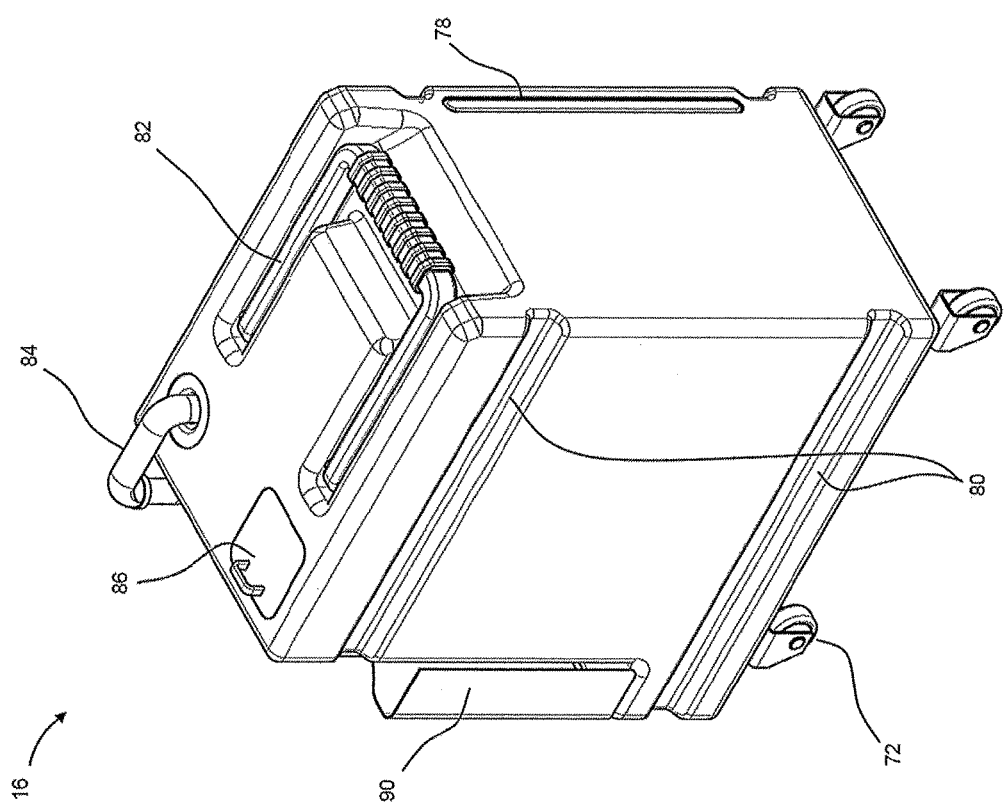
FIG. 6 illustrates a front perspective view of an embodiment of a fresh fluid reservoir of an amniotic bath incubator for premature infants.

Referring to FIG. 6, the amniotic bath incubator can comprise a reservoir 16, which can be a high volume container on casters 72 for mobility. A liquid level indicator 78 can be provided to alert users when the reservoir 16 needs refilling. In some embodiments, the reservoir 16 can comprise one or more level sensors configured to detect the level of fluid in the reservoir 16. For example, the reservoir 16 can comprise a top level detector and/or a low level detector. A top level detector can be configured to determine when the fluid level of the reservoir 16 is at or above a predetermined level, and a low level detector can be configured to determine when the fluid level of the reservoir 16 is at or below a predetermined level. When a fluid level of the reservoir 16 is detected to be below a predetermined level, the system can be configured to sound an alarm and/or electronically transmit and cause an alarm, whether visual or acoustic, to prompt an operator to fill the reservoir 16. In certain embodiments, the reservoir 16 can be directly connected to a water supply. When a fluid level of the reservoir 16 is detected to be below a predetermined level, the system can be configured to automatically refill the reservoir 16 from a water supply.

A series of slots 80 can be incorporated into the reservoir 16 for engaging the guides 32 on the frame 14. At the top of the reservoir 16, a recessed articulating reservoir handle 82 can allow lifting or directing the reservoir 16 on the casters 72 in and out of the incubator 10. A filling tube 84 can be incorporated into the reservoir 16 to allow users to replenish it with fresh or sterile fluid, and an amniotic container port 86 can be provided for introducing an amniotic fluid supply 88. Opposite the liquid level indicator 78, a hose bin 90 can be sized to hold the filling tube 84 when not in use. In certain embodiments, the reservoir 16 can be directly 6 connected to a fresh water line, for example in a hospital, and can include an automated or non-automated on/off valve to hold a constant predetermined amount of water in the reservoir 16.

Figure 7:
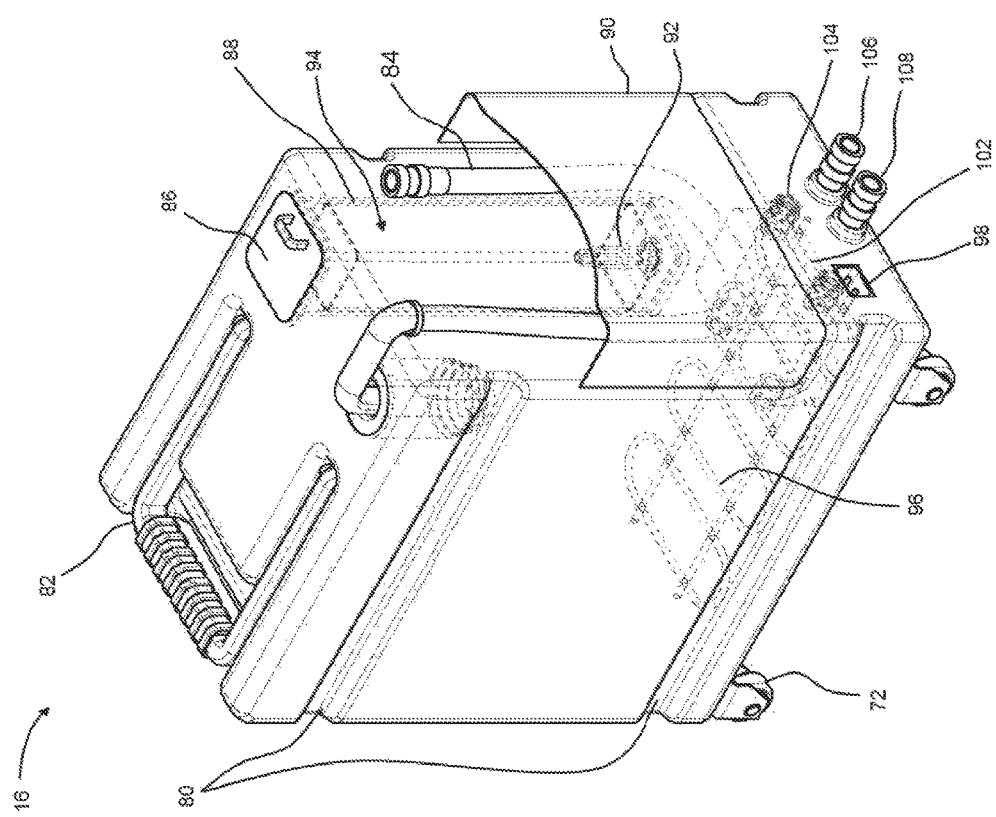
FIG. 7 illustrates a rear perspective view of an embodiment of a fresh fluid reservoir of an amniotic bath incubator for premature infants.

Referring to FIG. 7, the internal components of the reservoir 16 are shown. A filling tube 84 can be adapted for coupling to a water supply. The water supply can be configured to supply and/or comprise purified water, such as sterile and/or de-ionized water for example. In certain embodiments, the water supply can be configured to supply and/or comprise reserve-osmotic treated water. A synthetic amniotic fluid supply 88 can fit through an amniotic container port 86, and engage a valve 92 allowing a concentrated synthetic amniotic fluid 94 to mix with fluid in the reservoir 16 at predetermined rate. Mixing can be calibrated to create a fluid having component concentrations (osmolality, mineral, vitamin, electrolyte, amino-acid, protein, hormone, phospholipids, lipids, oxygen or other gas content, etc.) similar to natural amniotic fluid produced by the mother. In other embodiments, the synthetic amniotic fluid 94 may include nutrients and pharmaceutical compounds not found in natural amniotic fluid but which medically beneficial or necessary for care of the infant.

In order to preserve the temperature of fluid in the reservoir 16, a heating element 96, connected to a power supply 98 may be provided. In order to maintain sterility or near sterility, the synthetic amniotic fluid 94 may be continuously pumped through a filter 100, comprising a UV or similar system to clear it from debris, contaminants, bacteria, viruses and fungi. A pump 102 can urge fluid from the reservoir 16 up to the bath 12. In some embodiments, a valve system 104 can also contemplated for continuously mixing synthetic amniotic fluid 94. In such embodiments, the reservoir 16 can include a water bib 106 that pumps pure water and/or an amniotic fluid bib 108 that pumps a predetermined mixture of water and synthetic amniotic fluid 94.

Figure 8:
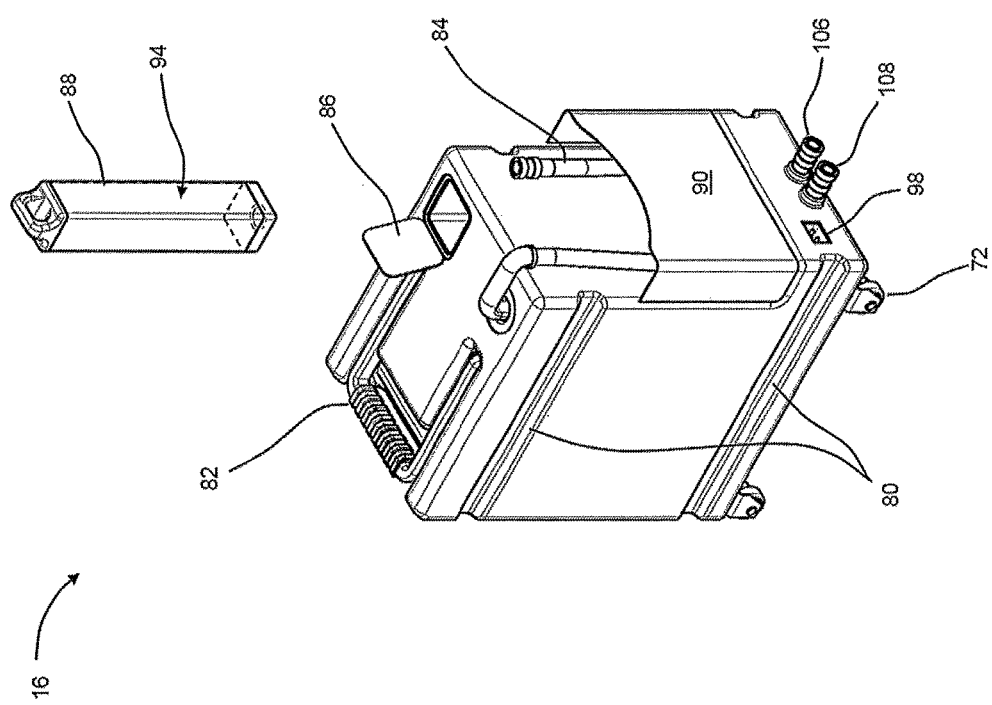
FIG. 8 illustrates an exploded view of an embodiment of a fresh fluid reservoir and a synthetic amniotic fluid cartridge of an amniotic bath incubator for premature infants.

Referring to FIG. 8, an amniotic fluid supply 88 can be removed through the amniotic container port 86 when empty and/or be replaced with a new amniotic fluid supply 88 filled 7 with concentrated synthetic amniotic fluid 94. The synthetic amniotic fluid 94 may have a predetermined osmolality, mineral content, vitamin content, electrolyte content, amino-acid content, protein content, hormone content, phospholipid content, including lipids, and an oxygen or gas content similar to natural amniotic fluid. It may also be adjusted according to medical needs of the infant. Additional fluid, nutrients and pharmaceuticals can be added to the synthetic amniotic fluid 94 for transdermal administration of fluids, nutrients and pharmaceuticals in a preterm infant through submerging of body in fluid. The non-keratinized thin dermal and epidermal layer in preterm infant skin can allow passage of fluid and molecules unlike keratinized and thicker skin of term and adult humans which can allow for application of nutrients and pharmaceuticals.

Figure 9:
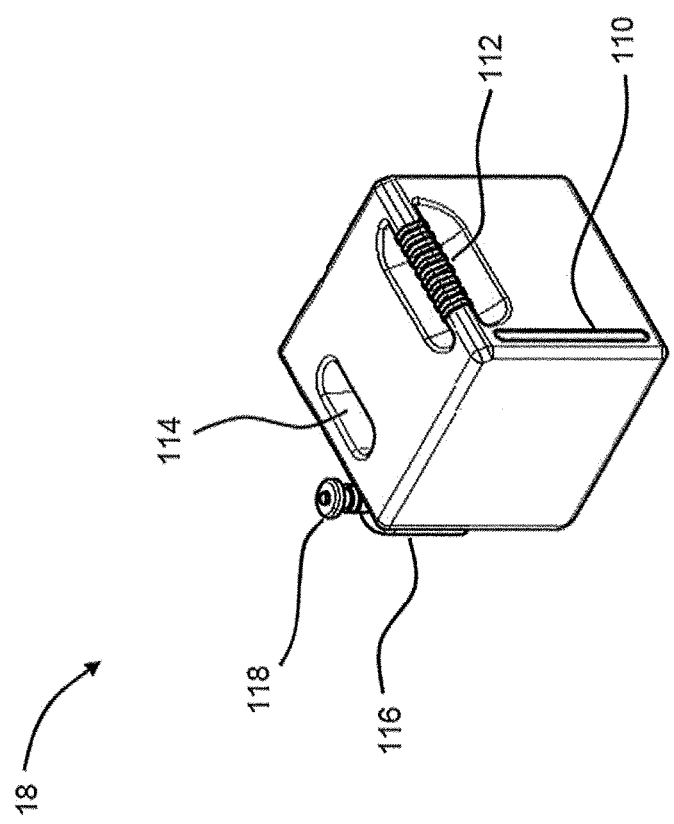
FIG. 9 illustrates a front perspective view of an embodiment of a waste fluid primary tank of an amniotic bath incubator for premature infants.

Referring to FIG. 9, a wastewater primary tank 18 is shown. A primary tank 18 can comprise a second liquid level indicator 78, a primary tank handle 112, and/or a wastewater inlet 114 in communication with the bath 12. A wastewater spout 116 having a wastewater valve 118 can be in communication with a secondary tank 20. When the secondary tank 20 is removed, the wastewater valve 118 may be closed allowing wastewater to collect in the primary tank 18, thereby avoiding interruption of amniotic incubation. The second level indicator can be monitored to make sure the wastewater valve 118 is reopened to the secondary tank 20 before the primary tank 18 overflows. Regardless of the presence or absence of the secondary tank 20, the primary tank 18 can also be removed from the frame 14 using the primary tank handle 112 for independent disposal of wastewater and cleaning.

In some embodiments, the wastewater tank, wastewater primary tank 18, and/or wastewater secondary tank 20 can comprise one or more level sensors configured to detect the level of fluid in the wastewater tank, wastewater primary tank 18, and/or wastewater secondary tank 20. For example, the wastewater tank, wastewater primary tank 18, and/or wastewater secondary tank 20 can comprise a top level detector and/or a low level detector. A top level detector can be configured to determine when the fluid level of the wastewater tank, wastewater primary tank 18, and/or wastewater secondary tank 20 is at or above a predetermined level, and a low level detector can be configured to determine when the fluid level of the wastewater tank, wastewater primary tank 18, and/or wastewater secondary tank 20 is at or below a predetermined level. When a fluid level of the wastewater tank, wastewater primary tank 18, and/or wastewater secondary tank 20 is detected to be above a predetermined level, the system can be configured to sound an alarm and/or electronically transmit and cause an alarm, whether visual or acoustic, to prompt an operator to empty the wastewater tank, wastewater primary tank 18, and/or wastewater secondary tank 20. In certain embodiments, the wastewater tank, wastewater primary tank 18, and/or wastewater secondary tank 20 can be directly connected to a sewage or disposal line. When a fluid level of the wastewater tank, wastewater primary tank 18, and/or wastewater secondary tank 20 is detected to be above a predetermined level, the system can be configured to automatically dispose contents of the wastewater tank, wastewater primary tank 18, and/or wastewater secondary tank 20 to the sewage or disposal line or other tank.

Figure 10:
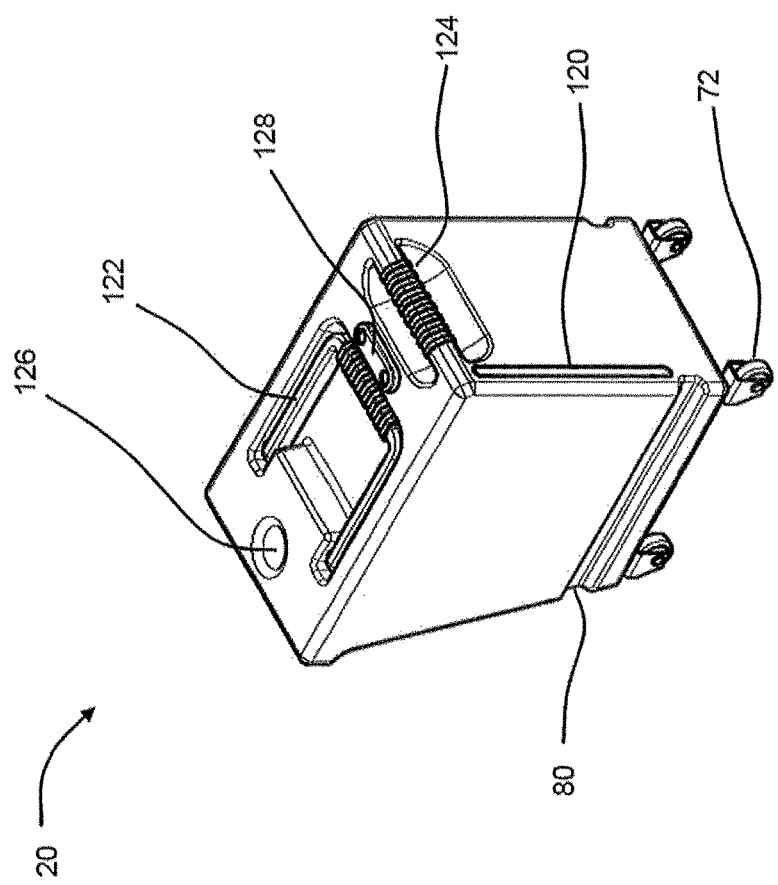
FIG. 10 illustrates a front perspective view of an embodiment of a waste fluid secondary tank of an amniotic bath incubator for premature infants.

Referring to FIG. 10, a wastewater secondary tank 20 is shown. Similar to the reservoir 16, the secondary tank 20 can comprise casters 72 for independent rolling and slots 80 for engaging the frame 14 and preserving the secondary tank 20 in alignment with the primary tank 18. Although the secondary tank 20 can be larger than the primary tank 18, it can comprise a third level indicator 120 to alert users when the secondary tank 20 is nearly full. The secondary tank 20 can comprise a recessed first secondary tank handle 122 and/or a second secondary tank handle 124. The first secondary tank handle 122 can articulate like the reservoir handle 82. The second secondary tank handle 124 can be stationary like the primary tank handle 112. Together, they can allow a user to conveniently and easily empty the secondary tank 20 when full. In some embodiments, the wastewater primary tank 18 and/or secondary tank 20 can comprise one or more rechargeable batteries or other power supply and/or one or more pumps for disposal of the wastewater content. In certain embodiments, the system comprises a single wastewater tank that comprises one or more rechargeable batteries or other power supply and/or one or more pumps for disposal of the wastewater content. The rechargeable battery or other power supply can be built into the wastewater primary tank 18, secondary tank 20, and/or single wastewater tank and/or can be selectively attached onto the wastewater primary tank 18, secondary tank 20, and/or single wastewater tank for use.

A secondary wastewater inlet 126 can accept wastewater from the wastewater spout 116 of the primary tank 18, once the secondary tank 20 is full, as measured by a third level indicator 120. In certain embodiments, the secondary tank 20 can be removed from the frame 14, emptied, cleaned, and replaced for further use. The secondary tank 20 can also include a registration point 128 for aligning it with the primary tank 18.

Figure 11:
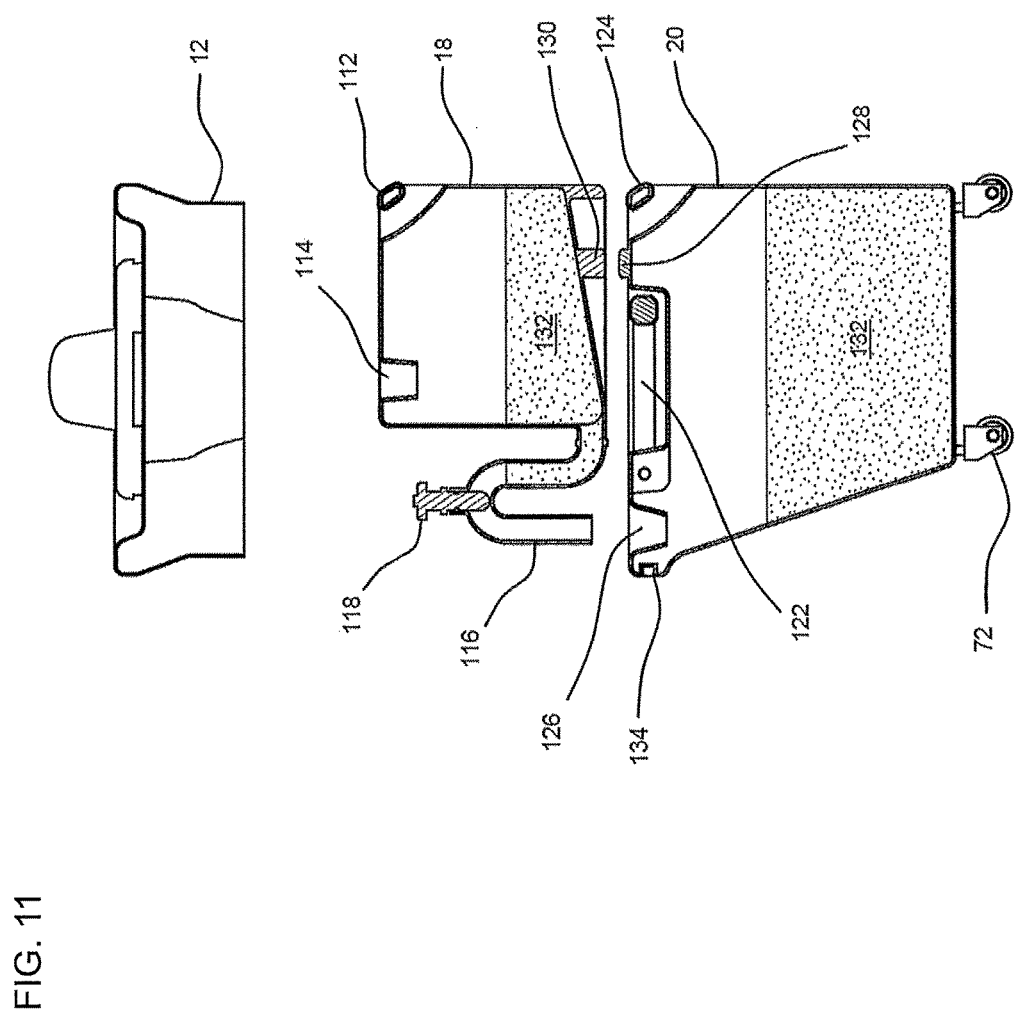
FIG. 11 illustrates a section view of an embodiment of a bath portion, a first tank, and a second tank of an amniotic bath incubator for premature infants.

Referring to FIG. 11, a bath 12, primary tank 18, and secondary tank 20 are shown in section view. In some embodiments, in this view, a complimentary registration point 130 is shown on the primary tank 18 for aligning with the registration point 128 on the secondary tank 20. When the secondary tank 20 is full of contaminated amniotic fluid 132, it can be dispensed through an emptying spout 134 near the secondary wastewater inlet 126.

In order to employ the incubator 10 when caring and maintaining a premature infant, a user can supply power to the incubator 10 and fill the reservoir 16 with fluid, such as water, which may be sterile, de-ionized, and/or otherwise purified. In some embodiments, the reservoir 16 can be released using the fresh water release pedal 68, which can allow a user to roll the reservoir 16 out from the frame 14 along the guides 32. The reservoir 16 can be rolled to a desired location for filling remotely from the incubator 10. While filling the reservoir 16, the liquid level indicator 78 may be monitored to ensure a proper volume of fluid and prevent overfilling. The filling tube 84 may be used to conveniently fill the reservoir 16 from a sink, or other difficult to reach location. In certain embodiments, the reservoir 16 can be configured to automatically fill fresh water as necessary from a water supply. For example, when one or more sensors of the reservoir 16 detect that the water level of the reservoir 16 is below a predetermined level, the system can be configured to automatically open one or more valves to refill the reservoir from a water supply.

Cover/Liner

Referring back to FIG. 1, in some embodiments, the amniotic bath incubator can comprise a cover or liner 1C. The cover 1C can be sterile and/or made replaceable. The cover 1C can be made of plastic. A nurse or health care provider can replace the cover periodically, for example about, at least about, or no more than about once every about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours, about 2 days, about 3 days, about 4 days, about 5 days, about 6 days, about 1 week, about 2 weeks, about 3 weeks, about 4 weeks, and/or within a range defined by two of the aforementioned values. In certain embodiments, the cover can be replaced as necessary.

In some embodiments, the cover or liner 1C can comprise or be configured to be used in conjunction with one or more safety straps or harnesses 15C for substantially maintaining the position of the infant. For example, the one or more safety straps or harnesses 15C can be configured to prevent accidental submersion of the infant in the fluid.

In certain embodiments, the cover or liner can comprise a general shape or configuration for providing sufficient support to an infant to sit up in the bath without being submerged. For example, the cover or liner 1C can comprise a depression of a general shape that allows for the infant to sit. As discussed above, the cover 1C can comprise a seatback and/or a post. A plurality of covers 1C of the same size may be provided for periodic replacement. In certain embodiments, a plurality of covers 1C of a generally same shape but different sizes may be provided for replacement as the infant grows. In some embodiments, a plurality of covers 1C can comprise different sizes and/or configurations to substantially match and/or accommodate adapters of different sizes and/or configurations.

Amniotic Fluid Disposal Unit

Figure 11A:
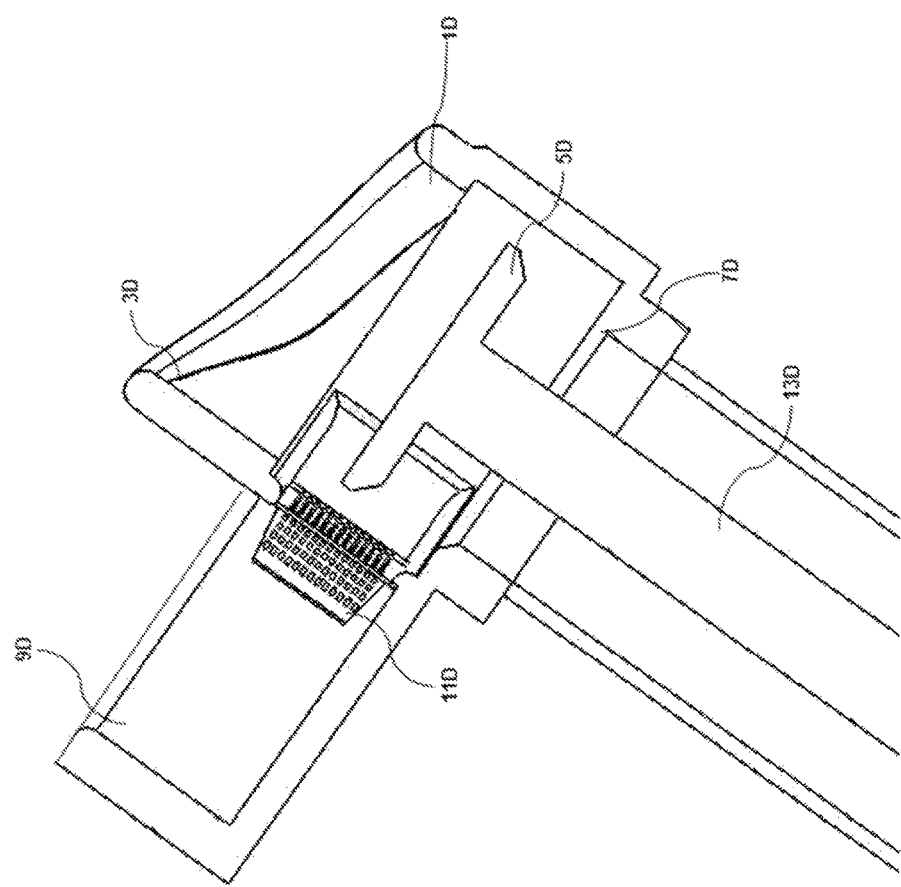
FIG. 11A illustrates a cross section view of an amniotic fluid disposal unit of an amniotic bath incubator.

In some embodiments, the cover or liner 1C can comprise and/or be configured to be used in conjunction with an amniotic fluid disposal unit. FIG. 11A illustrates an embodiment of an amniotic fluid disposal unit. The amniotic fluid disposal unit can be configured to perform the amniotic bath fluid change or a portion thereof. More specifically, the amniotic fluid disposal unit can be configured to collect and/or remove stool, urine, and/or contaminated synthetic amniotic fluid from the amniotic bath. The collected stool and/or contaminated synthetic amniotic fluid can be configured to be disposed into the wastewater tank. In some embodiments, the amniotic fluid disposal unit can be an integral part of the disposable cover or liner 1C.

The amniotic fluid disposal unit can comprise one or more stool collectors 1D, bath fluid inflow portions 9D, filters 11D, protective nets 3D, contamination sensors, and/or plug units 5D for the drain valve. The stool collector 1D can be donut-shaped in some embodiments. The stool collector 1D can be configured to be loosely positioned on or around the skin of the patient or infant in a manner such that it substantially surrounds the buttocks, anus, and/or external urethral orifice. The stool collector 1D may reduce the ability of fluid to flow between the amniotic fluid disposal unit and bath in the area of contact of the stool collector 1D and the skin of the patient or infant. Stool or urine from the infant or patient can be collected by the stool collector 1D. More specifically, in some embodiments, stool, urine, and/or amniotic fluid to be disposed can be collected by the stool collector 1D and flow through one or more filters to a drain valve. Amniotic fluid to be disposed can flow through the bath fluid inflow portion 9D and through one or more filters to a drain valve.

The bath fluid inflow portion 9D can comprise an opening configured to allow used and/or contaminated synthetic amniotic fluid to flow out of the bath. The bath fluid inflow portion 9D can further comprise one or more filters 11D. The one or more filters 11D can be positioned after the inflow opening and can be configured to prevent backflow of stool and/or fluid to be disposed back into the bath as stool is collected downstream of the one or more filters 11D.

In some embodiments, the stool collector 1D can comprise and/or be configured to be used in conjunction with one or more protective nets 3D. A protective net 3D can be configured to be positioned in the stool collector 1D. The protective net 3D can be configured to prevent suction of one or more portions of the body of the infant or patient, while allowing stool to pass through the protective net 3D.

In certain embodiments, one or more contamination sensors of the amniotic fluid disposal unit can be configured to detect, directly or indirectly, a contamination level of the synthetic amniotic fluid. In some embodiments, a bath fluid change process can be initiated when the detected contamination level is at or above a predetermined contamination level.

In some embodiments, the drain valve can be configured to open and/or close a drain line towards a wastewater tank of the system. In certain embodiments, the disposable bath cover or liner 1C can comprise a drain valve plug unit 5D and/or seat or ring 7D. The drain valve plug unit 5D and/or seat or ring 7D can be an integral part of the disposable bath cover 1C. The drain valve can also comprise a stem portion 13D, one or more seals, and/or actuators. The stem 13D, seal and/or actuator can be permanently attached to the amniotic bath incubator system. The plug unit 5D of the drain valve can be attached by a push/pull connector-fitting to the stem portion 13D of the valve during installation of the disposable bath cover 1C. When one or more sensors detect that the contamination level of the bath fluid is at or above a predetermined level that requires partial or complete change of the amniotic bath fluid, the control unit of the system can power the actuator of the valve. The plug unit 5D can then open, allowing the amniotic fluid along with stool to flow out of the amniotic bath through the amniotic fluid disposal unit.

Adapter Seat

Figure 11B:
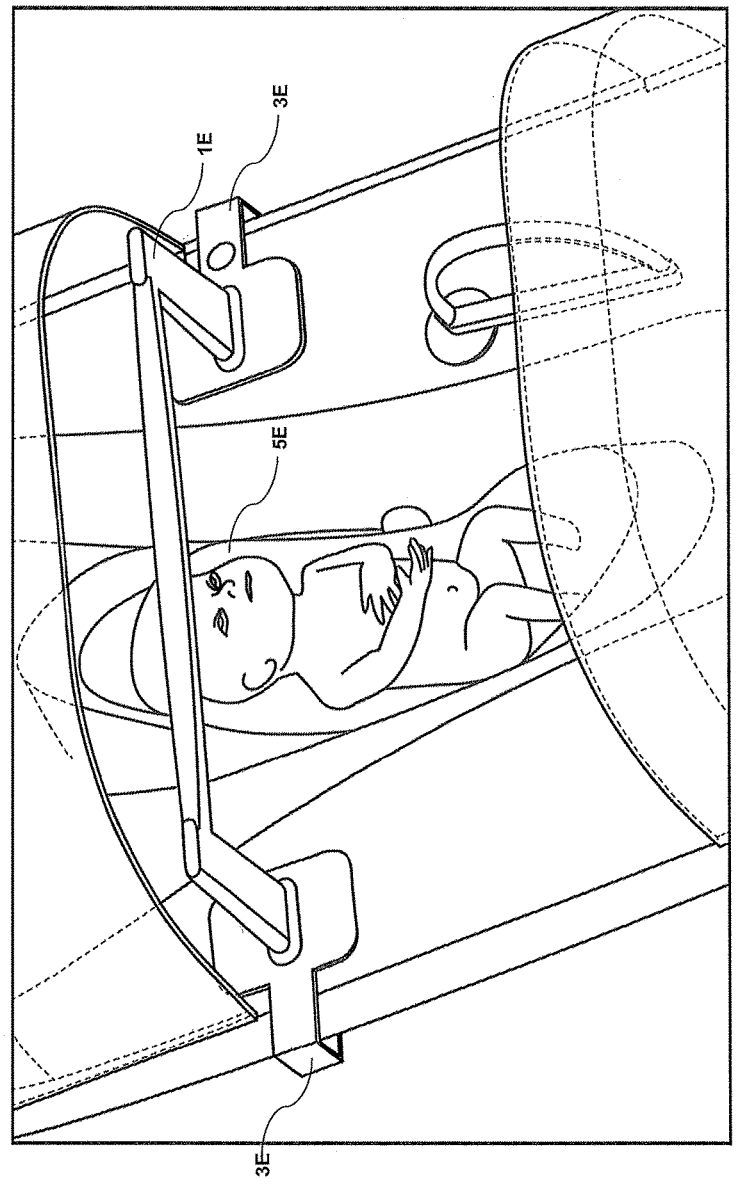
FIG. 11B illustrates a perspective view of an adapter of an amniotic bath incubator.

In some embodiments, the amniotic bath incubator system can comprise an adapter seat. FIG. 11B illustrates an embodiment of an adapter seat attached to an amniotic bath incubator system. The adapter seat 5E can be configured to be placed beneath the cover or liner 1C. In some embodiments, the system can comprise a plurality of adapter seats 5E. The plurality of adapter seats 5E can comprise different configurations and/or sizes, for example to accommodate infants of different sizes. By providing a plurality of adapter seats 5E of different sizes, in some embodiments, a single amniotic bath incubator system can be adapted for use with infants of different sizes by replacing and/or attaching an adapter seat 5E that substantially matches the size of the infant to be seated in the bath. Accordingly, a single size bath mold may be used to produce an amniotic bath incubator in certain embodiments with a plurality of replaceable adapter seats 5E of varying sizes. In some embodiments, the adapter seat 5E can comprise a soft and/or comfortable material. For example, the adapter seats can comprise a jell-like material.

The surface of the adapter 5E that faces towards the patient or infant can be configured to be in contact with the infant or patient. The overall design of the surface of the adapter 5E that faces towards the patient or infant can assure substantially equal level of comfort and safety to a smaller patient as a larger patient would feel without the adapter 5E. Other surfaces of the adapter 5E not facing and/or not in contact with the patient or infant can be designed to assure full functionality of the bath and can comprise one or more locking mechanisms for attaching and detaching the adapter 5E from the bath.

In some embodiments, the amniotic bath incubator can be configured to be used without attachment of an adapter seat 5E for infants of a certain size. For example, in certain embodiments, the amniotic bath incubator can be configured to be used without attachment of an adapter seat 5E for infants at or above a certain size, such as about 60 cm or 65 cm in height. For infants below a certain size, such as about 60 cm or 65 cm in height, the amniotic bath incubator can be configured to be used with attachment of an adapter seat 5E to accommodate for the size of the smaller infant. In certain embodiments, one or more adapters 5E can be configured to be used with infants of sizes between about 25 cm and about 65 cm in height. In certain embodiments, an operator or caregiver can place an adapter seat 5E of an appropriate size before placing an infant in the amniotic bath incubator.

The cover or liner 1C can be configured to substantially match the configuration and/or size of the adapter seat 5E. In certain embodiments, the system can further comprise a plurality of covers or liners 1C of different configurations and/or sizes to substantially match the plurality of adapter seats 5E.

Fluid Sensor

In certain embodiments, the amniotic bath incubator system can comprise a fluid sensor 17C configured to detect presence of fluid. For example, the fluid sensor 17C can be configured to be worn around the neck of the infant inside the bath. The fluid sensor 17C can be configured to sense accidental submersion of the infant (e.g., the infant's head) in the fluid, which can result in automatic lowering of fluid level. In some embodiments, one or more fluid sensors can be worn or placed on other parts of the infant's body that is desired not to be submerged in the fluid, such as the face of the infant.

Bridges/Mounts

Referring again to FIGS. 1 and 11B, in some embodiments, the cover 1C comprises one or more bridges or mounts 3C, 5C, 1E and/or is configured to be used in conjunction with one or more bridges or mounts 3C, 5C, 1E. The one or more bridges or mounts 3C, 5C, 1E can be configured to be located above the bath. In certain embodiments, the height of the one or more bridges or mounts 3C, 5C, 1E can be changed. For instance, the one or more bridges or mounts 3C, 5C, 1E can comprise and/or be connected to one or more motors or actuators for increasing and/or decreasing the height of the one or more bridges or mounts 3C, 5C, 1E. The height of the one or more bridges or mounts 3C, 5C, 1E as measured from a top surface of the cover 1C and/or as measured the fluid level, can be, for example, about, at least about, or no more than about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 25 cm, about 30 cm, about 35 cm, about 40 cm, about 45 cm, about 50 cm, and/or within a range defined by two of the aforementioned values.

The one or more mounts 3C, 5C, 1E can be configured to maintain one end of one or more tubes above the fluid. In certain embodiments, the height of the one or more bridges or mounts 3C, 5C, 1E can be changed according to a desired height based on the attached one or more tubes. For example, the one or more tubes can be one or more of an umbilical tube, a feeding tube, an oxygen tube, intravenous (IV) tube, or the like. More specifically, in some embodiments, the umbilical cord of a preterm infant can be cut relatively long compared to that of term infants and/or compared to current practice. One end of one or more umbilical tubes can then be configured to be connected to the umbilical cord of the preterm infant sitting inside the amniotic fluid bath to provide nutrients, oxygenation, medicine or the like and/or for sampling of blood or the like of the infant, for example for laboratory testing purposes. The umbilical cord can be attached to a bridge above the fluid level such that catheters and/or tubes inserted into the umbilical cord are not in contact with the fluid. In another embodiment, a clear, sterile, and/or plastic cover, which can be similar to a sterile ultrasound probe cover for example, can be placed on the catheter and/or other lines. In certain embodiments, such cover can be fastened and/or anchored to the umbilical cord to prevent contamination of the catheter and/or other line with amniotic fluid in case of accidental submersion of the umbilical catheter within fluid. Similarly, an IV tube can be connected to a vein of the infant sitting inside the amniotic fluid. Likewise, a feeding and/or oxygen tube can be connected to the mouth of the preterm infant. In any case, it can be advantageous to ensure that the other end of the tube(s) that is not connected to the infant is not submerged in the fluid and/or comprises a sterile and/or plastic covering in case of accidental submersion to prevent the synthetic fluid from entering the tube(s) and/or contamination or infection. As such, in certain embodiments, the other end of the tube(s) not connecting to the infant is anchored or otherwise set in place above the synthetic amniotic fluid by attaching to a bridge or mount 3C, 5C, 1E to ensure the one or more tube(s) do not become infected and keep them sterile.

In some embodiments, the amniotic bath incubator system comprises a single bridge or mount 1E. In certain embodiments, the amniotic bath incubator system comprises a first bridge or mount 3C for maintaining the position of one or tubes configured to be connected to the mouth of the infant, such as a feeding tube and/or oxygen tube, and a second bridge or mount 5C for maintaining the position of one or more tubes configured to be connected to the umbilical cord of the infant. In certain embodiments, the amniotic bath incubator system comprises three or more bridges or mounts 3C, 5C, 1E.

In certain embodiments, the bridge or mount can comprise a first side segment, a second side segment, and a top segment. The first side segment and/or the second side segment can extend upward from one or more edges of the amniotic bath in a vertical direction perpendicular to a top surface of the bath and/or bath fluid. The top segment or beam can be parallel to the top surface of the bath and/or bath fluid and can traverse a longitudinal or latitudinal axis of the incubator. The first side segment, second side segment, and/or top segment or beam can be substantially straight, curved, and/or angular. The first side segment, second side segment, and/or top segment or beam can be configured to connect only two of four outer sides of the periphery of a rectangular top surface of the bath. The first side segment, second side segment, top segment or beam, and the top surface of the bath can comprise an open space, as opposed to a closed space formed by a dome placed over the bath.

In some embodiments, the one or more bridges or mounts 3C, 5C, 1E can be an umbilical catheter bridge. An umbilical catheter bridge can be specifically designed to hold and/or guide an umbilical catheter line. The umbilical catheter bridge or one or more bridges or mounts 3C, 5C, 1E can be configured to be easily attached and/or detached form the amniotic bath incubator system. For example, in some embodiments, the umbilical catheter bridge or one or more bridges or mounts 3C, 5C, 1E can comprise one or more attachment mechanisms 3E for attaching and/or releasing from the amniotic bath incubator.

Modular Configuration

In some embodiments, the amniotic bath incubator system and/or device can comprise a modular configuration. In other words, one or more components of the system can be a module, allowing for easy replacement and attachment. For example, in certain embodiments, the system can comprise one or more fluid tanks, freshwater or purified water tanks, amniotic fluid tanks or bath, wastewater tanks, covers, domes, or the like that are modular or comprise one or more modules.

In certain embodiments, the one or more wastewater tanks, freshwater or purified water tanks, and/or amniotic bath fluid tanks can be configured to be connected to a water line and/or sewage line. In such embodiments, fresh or purified water can be continuously and/or periodically be provided to the freshwater or purified water tank directly. In some embodiments, the fresh or purified water tank can comprise one or more sensors for detecting a fluid level within the tank. In certain embodiments, the fresh or purified water tank can be configured to automatically refill the tank with fresh and/or purified water when the fluid level within the tank is at or below a predetermined level, such as at or below 10%. Similarly, wastewater can be continuously and/or periodically be removed from the wastewater tank directly into a sewage line or other waste tank. In some embodiments, a wastewater tank can comprise one or more sensors for detecting a fluid level within the tank. In certain embodiments, the wastewater tank can be configured to automatically dispose its contents when the fluid level within the tank is at or above a predetermined level, such as at or above 90%.

In certain embodiments, the one or more wastewater tanks and/or freshwater or purified water tanks are not connected to a water line and/or sewage line. In such embodiments, the one or more wastewater tanks and/or freshwater or purified water tanks can be configured to be removed from the system for refilling and/or disposal. After removing, the one or more wastewater tanks and/or freshwater or purified water tanks can be moved to a location that allows for addition or purified or fresh water and/or removal of wastewater. For example, in some embodiments, the one or more waste water tanks and/or freshwater or purified water tanks can comprise one or more rollers or wheels. A user may be able to utilize the one or more rollers or wheels to easily move the one or more freshwater or purified water tanks to a water supply source to add water. Similarly, a user may be able to utilize the one or more rollers or wheels to easily and conveniently move the one or more wastewater tanks to a location for wastewater removal, such as a sewage line, to remove the wastewater. In some embodiments, the fresh or purified water tank can be configured to automatically alert an operator, for example through visual and/or audio alerts, when the fluid level within the tank is at or below a predetermined level, such as at or below 10%, to prompt the operator to refill the tank. In certain embodiments, the wastewater tank can be configured to automatically alert an operator, for example through visual and/or audio alerts, when the fluid level within the tank is at or above a predetermined level, such as at or above 90%, to prompt the operator to empty the tank.

In some embodiments, the system can comprise a plurality of wastewater tanks and/or fresh water or purified water tanks. For example, an amniotic bath incubator can comprise two or more wastewater tanks and/or fresh or purified water tanks. As such, in certain embodiments, while one of the two or more wastewater tanks and/or fresh or purified water tanks are being refilled or emptied, the amniotic bath incubator may continue to comprise at least one wastewater tank and/or fresh or purified water tank.

In certain embodiments, an operator may switch out or replace one or more wastewater tanks and/or fresh or purified water tanks with pre-filled or pre-emptied wastewater tank and/or fresh or purified water tank. For example, after removing an emptied or nearly emptied fresh water or purified water tank, the operator may immediately replace the amniotic bath incubator with another fresh or purified water tank that has already been filled. As such, the amniotic bath incubator can continue to comprise at least one functioning fresh or purified water tank while the original emptied tank is being filled. Similarly, after removing a full or nearly full wastewater tank, the operator may immediately replace the amniotic bath incubator with another wastewater tank that is not full or is empty. As such, the amniotic bath incubator can continue to comprise at least one functioning wastewater tank while the original wastewater tank is being emptied.

In some embodiments, the one or more fresh or purified water tanks can comprise one or more handles and/or wheels for easy transport to nearby bathwater sink. The one or more fresh water tanks can comprise a disposable hose to allow easy filling of the tank from the sink faucet. The water can be purified of impurities, electrolytes, minerals and bacteria through a deionization and/or reverse osmosis filtration system. The deionization filtration system can be built into the amniotic bath system or device in some embodiments. In other embodiments, the amniotic bath system or device can be configured to be used in conjunction with a separate deionization and/or reverse osmosis filtration system.

The freshwater tank can comprise a sterile cover. The sterile cover can be made of plastic or metal and can be disposable. For example, the sterile cover of the freshwater tank can be configured to be replaced about, at least about, or no more than about once every about 3 hours, about 3 hours, about 6 hours, about 9 hours, about 12 hours, about 15 hours, about 18 hours, about 21 hours, about 24 hours, about 36 hours, about 48 hours, and/or within a time range defined by two of the aforementioned values. The sterile cover can also be configured to be replaced with every refill of the tank.

The waste fluid tank can comprise a filter to collect the stool and solids from the waste. The filter can be replaceable and/or disposable. In some embodiments, the waste fluid can sit on a disposable plastic cover. In certain embodiments, the wastewater tank can comprise one or more pumps and/or hoses for easy disposal of the wastewater fluid into a sink or sewage. The one or more pumps can be powered by a power source, such as a rechargeable battery.

In some embodiments, the system can comprise one or more latches or locks that allow for removal of the one or more modular components. For example, a user may release the one or more latches or locks to allow removal of the one or more modular components, such as one or more fresh or purified water tanks and/or wastewater tanks. After reattachment, the user may again lock the one or more latches or locks to keep the one or more modular components in place within the system or device.

In certain embodiments, the amniotic bath incubator system and/or device itself can comprise one or more wheels or rollers. For example, a user may be able to easily or conveniently move the amniotic bath incubator system and/or device itself by using the one or more wheels or rollers.

Synthetic/Simulated Amniotic Fluid

Biological amniotic fluid is the protective liquid bathing the fetus during pregnancy and serves several functions such as heat reservoir for thermoregulation, a reservoir for absorption of water by the fetus through the intramembranous pathway and an environment for fetal movement and comfort. Source of amniotic fluid is through combination of excretions from fetal kidneys, respiratory system, gastrointestinal system and surface of the placenta. Amniotic fluid can be said to be unique amongst all physiologic fluids in terms of its osmolality, pH and mineral content.

In some embodiments, a synthetic or simulated amniotic fluid can be produced to be used in conjunction with the amniotic bath incubator systems, devices, and methods. For example, an infant, preterm or otherwise, can be placed in a synthetic or simulated amniotic fluid. The synthetic or simulated amniotic fluid can comprise one or more characteristics that are similar to those of biological amniotic fluid. For example, the composition of the synthetic or simulated amniotic fluid can comprise one or more electrolytes, minerals, proteins, albumin, amino acids, glucose, enzymes, phospholipids, hormones, lipids, carbohydrates, lactate, and/or pyruvate. In certain embodiments, the synthetic or simulated amniotic fluid can comprise one or more nutrients and/or drugs.

In some embodiments, the simulated or synthetic fluid can comprise a crystalloid solution of electrolytes and minerals especially designed to match or mimic the osmolality, pH, electrolyte and mineral content of physiologic amniotic fluid in the womb. The osmolality, pH, electrolyte and/or mineral content of physiologic amniotic fluid can change from the 22nd week to term at 40th week of pregnancy. As such, in certain embodiments, various concentrations of concentrated crystalloid solutions can be placed into one or more cartridges and/or the amount of fluid to be mixed with contents of a cartridge can be adjusted by an operator through one or more dosing pumps. The simulated amniotic fluid can be produced in some embodiments through mixing of fluid from a concentrated electrolyte and mineral cartridge with deionized purified water. The cartridge can be replaced by the nurses every about 6 hours, about 12 hours, about 18 hours, about 24 hours, about 36 hours, about 48 hours, and/or within a range defined by two of the aforementioned values. In certain embodiments, the cartridge can be replaced after a particular number of refills of the simulated amniotic fluid, for example after about 1 refill, about 2 refills, about 3 refills, about 4 refills, about 5 refills, about 6 refills, about 7 refills, about 8 refills, about 9 refills, about 10 refills, and/or within a range defined by two of the aforementioned values.

The synthetic or simulated amniotic fluid can comprise one or more amino acids and/or glucose. The one or more amino acids and/or glucose can be absorbed by an infant from the synthetic or simulated amniotic fluid through the skin. The potential uptake of such substances can enhance organ weights and fetal growth. In some embodiments, the concentration of one or more amino acids and/or glucose in the synthetic or simulated amniotic fluid can be higher than the concentration of the one or more amino acids and/or glucose in physiologic amniotic fluid, for example to provide a sufficient source of nutrition for the infant.

More specifically, in some embodiments, the synthetic or simulated amniotic fluid can comprise Na. The concentration of Na in the synthetic or simulated amniotic fluid can be, for example, between about 120 mEQ/l and about 150 mEQ/l or between about 130 mEQ/l and about 140 mEQ/l. In certain embodiments, the Na concentration of the synthetic or simulated amniotic fluid can be about 136.10 mEQ/l and/or between about 131.95 mEQ/l and about 140.25 mEQ/l.

In certain embodiments, the synthetic or simulated amniotic fluid can comprise K. The concentration of K in the synthetic or simulated amniotic fluid can be, for example, between about 2 mEQ/l and about 5 mEQ/l or between about 3 mEQ/l and about 4.5 mEQ/l. In certain embodiments, the K concentration of the synthetic or simulated amniotic fluid can be about 3.89 mEQ/l and/or between about 3.71 mEQ/l and about 4.07 mEQ/l.

In some embodiments, the synthetic or simulated amniotic fluid can comprise Cl. The concentration of Cl in the synthetic or simulated amniotic fluid can be, e.g., between about 100 mEQ/l and about 120 mEQ/l or between about 105 mEQ/l and about 115 mEQ/l. In certain embodiments, the Cl concentration of the synthetic or simulated amniotic fluid can be about 110.30 mEQ/l and/or between about 114.1 mEQ/l and about 106.5 mEQ/l.

In certain embodiments, the synthetic or simulated amniotic fluid can comprise Ca. The concentration of Ca in the synthetic or simulated amniotic fluid can be, e.g., between about 2.5 mEQ/l and about 4.5 mEQ/l or between about 3 mEQ/l and about 4 mEQ/l. In certain embodiments, the Ca concentration of the synthetic or simulated amniotic fluid can be about 3.39 mEQ/l and/or between about 2.97 mEQ/l and about 3.81 mEQ/l.

In some embodiments, the synthetic or simulated amniotic fluid can comprise glucose. The concentration of glucose in the synthetic or simulated amniotic fluid can be, e.g., between about 20 mg/dl and about 35 mg/dl or between about 25 mg/dl and about 30 mg/dl. In certain embodiments, the glucose concentration of the synthetic or simulated amniotic fluid can be about 27.67 mg/dl and/or between about 15.72 mg/dl and about 39.62 mg/dl. In certain embodiments, the synthetic or simulated amniotic fluid can comprise a higher concentration of glucose than found in physiologic amniotic fluid. For example, the concentration glucose in the synthetic or simulated amniotic fluid can be above about 30.00 mg/dl, about 40.00 mg/dl, about 50 mg/dl, about 60 mg/dl, about 70 mg/dl, about 80 mg/dl, and/or between a range defined by two of the aforementioned values.

In certain embodiments, the synthetic or simulated amniotic fluid can comprise $HCO_3$. The concentration of $HCO_3$ in the synthetic or simulated amniotic fluid can be, e.g., between about 5 mEQ/l and about 25 mEQ/l or between about 10 mEQ/l and about 20 mEQ/l. In certain embodiments, the $HCO_3$ concentration of the synthetic or simulated amniotic fluid can be about 14.50 mEQ/l and/or between about 12.33 mEQ/l and about 16.67 mEQ/l.

In some embodiments, the synthetic or simulated amniotic fluid can comprise protein. The total concentration of protein in the synthetic or simulated amniotic fluid can be, e.g., between about 0.1 g/dl and about 1.0 g/dl or between about 0.2 g/dl and about 0.8 g/dl. In certain embodiments, the total protein concentration of the synthetic or simulated amniotic fluid can be about 0.55 g/dl and/or between about 0.36 g/dl and about 0.74 g/dl. In certain embodiments, the total concentration of protein in the synthetic or simulated amniotic fluid can be above about 0.1 g/dl, about 0.2 g/dl, about 0.3 g/dl, about 0.4 g/dl, about 0.5 g/dl, about 0.6 g/dl, about 0.7 g/dl, about 0.8 g/dl, about 0.9 g/dl, about 1.0 g/dl, about 1.1 g/dl, about 1.2 g/dl, about 1.3 g/dl, about 1.4 g/dl, about 1.5 g/dl, about 1.6 g/dl, about 1.7 g/dl, about 1.8 g/dl, about 1.9 g/dl, and/or about 2.0 g/dl. In some embodiments, the total concentration of protein in the synthetic or simulated amniotic fluid can be higher than the total concentration of protein in physiologic amniotic fluid.

In certain embodiments, the synthetic or simulated amniotic fluid can comprise albumin. The concentration of albumin in the synthetic or simulated amniotic fluid can be, e.g., between about 0.1 g/dl and about 1.0 g/dl or between about 0.2 g/dl and about 0.7 g/dl. In certain embodiments, the albumin concentration of the synthetic or simulated amniotic fluid can be about 0.42 g/dl and/or between about 0.31 g/dl and about 0.53 g/dl. In some embodiments, the albumin concentration of the synthetic or simulated amniotic fluid can be above about 0.1 g/dl, about 0.2 g/dl, about 0.3 g/dl, about 0.4 g/dl, about 0.5 g/dl, about 0.6 g/dl, about 0.7 g/dl, about 0.8 g/dl, about 0.9 g/dl, and/or about 1.0 g/dl. In certain embodiments, the albumin concentration of the synthetic or simulated amniotic fluid can be higher than the albumin concentration of physiologic amniotic fluid.

In some embodiments, the osmolality of the synthetic or simulated amniotic fluid can be, e.g., between about 200 mosm/kg and about 350 mosm/kg or between about 250 mosm/kg and about 300 mosm/kg. In certain embodiments, the osmolality of the synthetic or simulated amniotic fluid can be about 272.50 mosm/kg and/or between about 264.52 mosm/kg and about 280.48 mosm/kg.

In certain embodiments, the pH of the synthetic or simulated amniotic fluid can be between about 7 and about 10 or between about 8 and about 9. In certain embodiments, the pH of the synthetic or simulated amniotic fluid can be about 8.4 and/or between about 8.01 and about 8.79.

Synthetic/Simulated Amniotic Fluid Production

To produce the synthetic or simulated amniotic fluid, in some embodiments, one or more components of the synthetic or simulated amniotic fluid can be dissolved in purified or fresh water. For example, one or more cartridges comprising one or more components of the synthetic or simulated amniotic fluid in concentrated doses can be dissolved in purified or fresh water to produce the synthetic or simulated amniotic fluid for use in the bath. In some embodiments, the system can comprise a single cartridge that comprises all of the desired components of the synthetic or simulated amniotic fluid. In other embodiments, the system can comprise a plurality of cartridges that each comprises some subset of the desired components of the synthetic or simulated amniotic fluid. For example, in some embodiments, a first cartridge can comprise a crystalloid solution of one or more electrolytes and/or minerals. The first cartridge can also comprise albumin. In certain embodiments, the system can comprise a second cartridge that comprises one or more amino acids and/or glucose. The contents of the second cartridge can be dissolved after, before, and/or simultaneously with the contents of the first cartridge. In certain embodiments, the system can comprise three, four, five, six, seven, eight, nine, and/or ten cartridges, each comprising different compositions. For example, each of the plurality of cartridges can comprise different components of the synthetic amniotic fluid and/or different concentrations thereof and/or different compositions thereof.

In some embodiments, the system can comprise a plurality of cartridges for use with infants in different stages of development, age, size, or the like. For instance, a particular cartridge may be optimized for producing an amniotic bath for infants at a particular stage of growth. In some embodiments, the plurality of cartridges may all comprise the same or similar components but at different concentrations. In certain embodiments, the plurality of cartridges may each comprise different compositions of components and/or different concentrations. The plurality of cartridges and their compositions and concentrations can be designed to match or mimic the composition of biological amniotic fluid depending on the development of pregnancy. As such, the concentration and/or dose of each component of the simulated and/or synthetic amniotic fluid can be changed as the infant develops. In some embodiments, the concentration of one or more electrolytes, minerals, amino acids, albumin, vitamins, glucose, and/or medicines or other therapeutic agents in the synthetic amniotic fluid can be controlled automatically, semi-automatically, or manually through a control unit. The control unit can be configured to adjust the injection rate of a dosing pump configured to pump purified water and/or contents of a cartridge for mixing to control the concentration of one or more components. The concentration of one or more components of the synthetic amniotic fluid can be controlled according to gestation age of the infant, size of the infant, and/or other medical indications.

In some embodiments, one or more desired components are dissolved in fresh or purified water directly in the amniotic bath incubator system or device. In other embodiments, the one or more desired components are dissolved in fresh or purified water outside of the amniotic bath incubator system or device and are added to the device or system afterwards. In certain embodiments, one or more desired components are dissolved in fresh or purified water to produce the synthetic or simulated amniotic fluid in a batch process. In other embodiments, one or more desired components are dissolved in fresh or purified water to produce the synthetic or simulated amniotic fluid via continuous mixing. For example, the amniotic bath incubator system or device can comprise one or more metered or dosing pumps that are configured to pump a particular amount of purified or fresh water and/or concentrated synthetic amniotic fluid or components thereof to continuously mix and obtain the synthetic or simulated amniotic fluid.

More specifically, in certain embodiments, one or more dosing or metered pumps of the system can be configured to precisely mix a desired amount of concentrated amniotic fluid with filtered or purified fresh water to create the right balance of pH and osmolality required by the clinician for each particular gestational age. The simulated amniotic fluid can then be pumped into the bath. In some embodiments, the simulated amniotic fluid is pumped into the bath after a disinfection process, for example through a UV bacterial filter.

The simulated or synthetic amniotic fluid of the bath can be drained or flushed and replaced periodically and/or continuously to reduce risks of colonization with bacteria. For example, the bath fluid can be drained and replaced continuously, every about 3 hours, about 6 hours, about 9 hours, about 12 hours, about 15 hours, about 18 hours, about 21 hours, about 24 hours, about 36 hours, about 48 hours, and/or within a range defined by two of the aforementioned values. In some embodiments, the bath fluid can be drained and replaced with every infant stool. In some embodiments, the system can comprise a rinser on the unit configured to allow rinsing of the skin of the infant from solids and for hydration of head and neck area by the parents and staff.

In some embodiments, the amniotic bath incubator can comprise one or more sensor to measure or estimate the volume of synthetic or simulated amniotic fluid present in the bath. For example, the amniotic bath can comprise one or more weight sensors configured to weigh and monitor a weight of the bath. Similarly, the amniotic bath can comprise one or more fluid level sensors configured to detect the fluid level within the bath. In certain embodiments, the amniotic bath incubator can comprise one or more sensors for determining a volume of amniotic fluid fed to the bath and a volume of fluid exiting the bath, for example from overflowing and/or through a disposal line.

In certain embodiments, the system can be configured to produced and/or provide additional volume of synthetic or simulated amniotic bath fluid to the bath based on the measured or estimated volume of synthetic or simulated amniotic fluid present in the bath. For example, the system can be configured to newly produce additional synthetic or simulated amniotic bath fluid or provide pre-produced synthetic or simulated amniotic bath fluid to the bath of an amount or volume necessary to maintain a steady or full level of fluid within the bath.

Disinfection

In some embodiments, the synthetic or simulated amniotic fluid can be disinfected before placing an infant in the synthetic or simulated amniotic fluid. For example, in certain embodiments, a disinfection cartridge comprising one or more disinfecting agents, chemical or otherwise, can be configured to be dissolved in purified water and/or synthetic or simulated amniotic fluid. In other embodiments, the purified water and/or synthetic or simulated amniotic fluid can be pumped through a disinfection process within or outside of the amniotic bath incubator system or device.

In some embodiments, the purified or fresh water can be disinfected before dissolving one or more components for producing the synthetic or simulated amniotic fluid. In other embodiments, synthetic or simulated amniotic fluid that has already been produced is subsequently disinfected. In certain embodiments, disinfection and dissolution of components for producing the synthetic or simulated amniotic fluid are performed simultaneously in purified or fresh water.

In certain embodiments, a disinfection procedure of the whole or part of the amniotic bath incubator system or device can be performed. For example, disinfection fluid can be passed through one or more tubes, tanks, or the like of an amniotic bath incubator to disinfect the system. A disinfection procedure can be performed manually and/or automatically. The disinfection procedure can be performed periodically. For example, the disinfection procedure can be performed about or at least about once every about 12 hours, about 24 hours, about 36 hours, about 48 hours, about 60 hours, about 72 hours, about 4 days, about 5 days, about 6 days, about 7 days, about 2 weeks, about 3 weeks, about 4 weeks, and/or within a range defined by two of the aforementioned values.

Method of Use Overview

Referring to FIGS. 2-11, in some embodiments, with the reservoir 16 filled, the filling tube 84 may be placed in the hose bin 90 for future use. The user may then open the amniotic container port 86 and insert a fresh amniotic fluid supply 88. An expended amniotic fluid supply 88 may be removed as necessary. The amniotic fluid supply 88 can be pressed down on the valve 92. The reservoir 16 can be then reinserted into the frame 14, thereby reconnecting the power supply 98, water bib 106 and amniotic fluid bib 108.

With the reservoir 16 reconnected, the power supply 98 can cause the valve 92 to open, causing concentrated synthetic amniotic fluid 94 to enter the filter 100, pump 102, and valve system 104, thereby mixing a predetermined amount of concentrated synthetic amniotic fluid 94 with fluid in the reservoir 16. While the reservoir 16 is connected to the power supply 98, the heating element 96 can pre-heat the fluid and amniotic fluid supply 88 to a preferred predetermined temperature, thereby easing the amount of heating required at the bath 12. With the reservoir 16 filled and at the proper temperature, the incubator 10 can be ready to receive an infant.

The user can remove the dome 22 and insert a cover 62 in the bath 12. The bath 12 can be then filled with a desired amount of synthetic amniotic fluid 12 using the amniotic fluid control 54. Optionally, water may be added using the water control 52, if only water is desired, or if a weaker concentration of synthetic amniotic fluid 94 is needed. The additional controls 56 can be used to control temperature, and other characteristics of the bath 12. The temperature, liquid composition, and other data can be optionally visible on a sensor readout 60 located on the lower sensor panel 66. The temperature of fluid in the bath 12 can be maintained by heating elements proximal to the bath 12. If necessary, the sliding shelf 28 may be extended for holding the infant or other materials.

The infant can be placed in a semi-seated position in the sump portion 40 of the bath 12, supported against the seatback 34 with the infant's legs against the post 36. The infant may also be fastened with safety straps. The surface features 38 can help stimulate the infant's skin and prevent undesired adhesion to the cover 62. Once the infant is located in the bath 12, and surrounded by synthetic amniotic fluid 94 at a preferred temperature, the dome 22 may be replaced to help maintain temperature and sterility. To access the infant without removing the dome 22, a user can reach through one or more sleeve ports 24 in some embodiments. In another embodiment, the infant can be completely submerged if adequate nutrition and oxygenation is maintained through umbilical vessels by medical staff and strict sterile environment of the fluid maintained in medical setting to allow swallowing action of amniotic fluid and diaphragm exercise of fluid filled lungs similar to fetal action in mother's womb.

In certain embodiments, for a more sterile embodiment, one or more sleeves may be provided in the one or more sleeve ports 24. In some embodiments, a radiant heating lamp can be provided on the device to provide necessary heat during examinations and procedures performed by the physicians or nursing staff, when the synthetic amniotic fluid 94 level is decreased or drained from the bath 12, when the cover 62 is changed, and/or when refreshing the fluid with the infant still in place in the bath 12. As discussed, sterile and fluid resistant leads, catheters, tubing and other elements may be included which attach to the infant's body while submerged in synthetic amniotic fluid, or attached to the infant's face or head above the fluid. These may be coupled to various medical and monitoring devices in the ICU.

Any synthetic amniotic fluid 94 splashing out of the sump portion 40 can remain on the shallow portion 42 of the bath 12, confined by the raised rim 44. In the event the shallow portion 42 is overfilled, excess fluid traveling over the raised rim 44 can drain into the gutter 46 and also drain down into the primary tank 18. A conforming drain region 64 surrounding the sump portion 40 can also drain down into the primary tank 18.

The infant may remain in the bath 12 for a predetermined period of time, and/or until the synthetic amniotic fluid 94 becomes contaminated. In particular, the cover 62 can be exchanged routinely in a scheduled manner to prevent bacterial or fungal growth. When the fluid requires changing, the infant can be removed, and the contaminated amniotic fluid 132 can be drained from the bath 12 using a central drain at the base of the sump portion 40. Contaminated amniotic fluid 132 leaving the bath 12 can enter the wastewater inlet 114 of the primary tank 18, which can begin to fill and move into the wastewater spout 116. Once the contaminated amniotic fluid 132 reaches the top of the wastewater spout 116, it can drain into the secondary tank 20. The primary tank 18 and secondary tank 20 can be of sufficient volume, such that a large quantity of contaminated amniotic fluid 132 can be washed through the bath 12 before they need to be emptied.

Eventually, the secondary tank 20 may fill enough to warrant emptying. To remove the secondary tank 20, the user may first seal the wastewater valve 118 on the primary tank 18, preventing contaminated amniotic fluid 132 from escaping when the secondary tank 20 is removed. The user can then depresses the wastewater release pedal 70, and rolls out the secondary tank 20 along the guides 32, and rolls it to a desired drainage site, such as a utility sink or similar cleaning location. By lifting the first secondary tank handle 122, the secondary tank 20 can be balanced for raising it into a pouring position. The second secondary tank handle 124 can then be lifted to pour contaminated amniotic fluid 132 out of the emptying spout 134. Cleaning water or solution may be introduced into the secondary tank 20 for sterilization.

While the secondary tank 20 is being emptied, the primary tank 18 can be left in place to accept contaminated amniotic fluid 132 from the bath 12. When the secondary tank 20 is placed back in position, the wastewater valve 118 can be opened allowing excess contaminated amniotic fluid 132 to flow from the primary tank 18 into the secondary tank 20. In some embodiments, the primary tank 18 can be removed for emptying and cleaning while leaving the secondary tank 20 in position. After the primary tank 18 is cleaned, it can be placed back atop the secondary tank 20. A registration point 128 on the secondary tank 20 can match a complimentary registration point 130 on the primary tank 18 to make sure they are in proper alignment, and that the wastewater inlet 114 is aligned with the bath 12 before contaminated amniotic fluid 132 is drained into them.

System Overview

Figure 12:
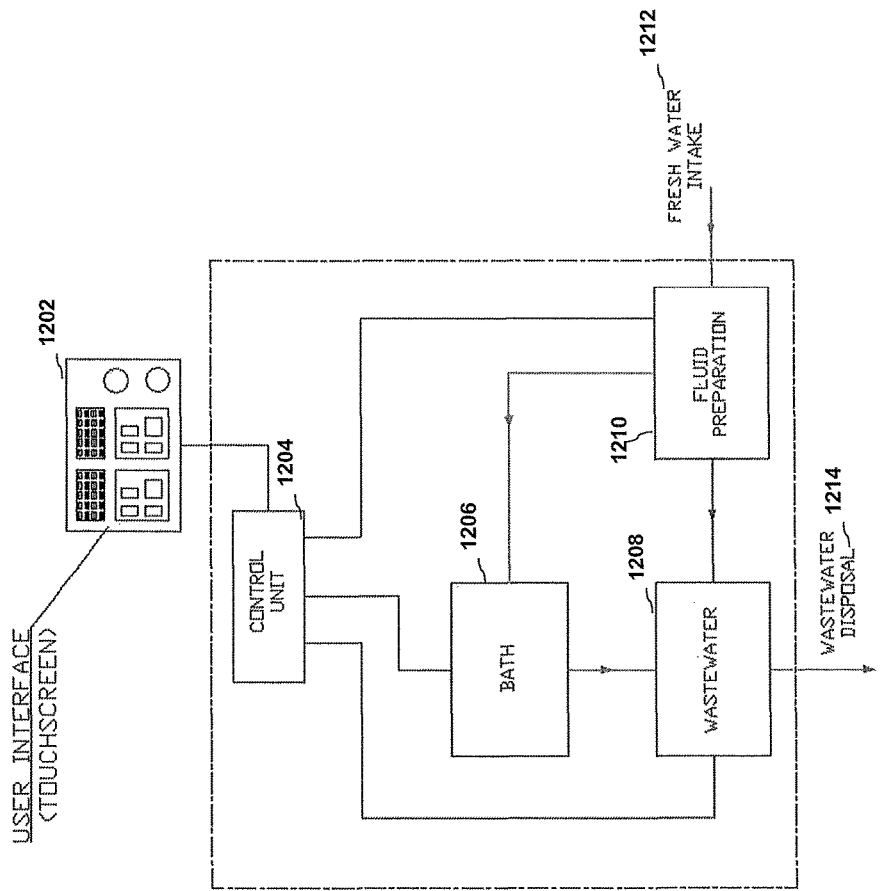
FIG. 12 is a block diagram depicting an overview of an embodiment of an amniotic bath incubator system for premature infants.

FIG. 12 is a block diagram depicting an overview of an embodiment of an amniotic bath incubator system for premature infants. As depicted in FIG. 12, in some embodiments, an amniotic bath incubator system comprises a user interface 1202, a control unit 1204, a bath 1206, a waste water system 1208, and/or an amniotic fluid preparation system 1210.

The fluid preparation system 1210 can be configured to intake fresh and/or purified water from a fresh water intake 1212. In some embodiments, a water tank, which itself can be disposable, is configured to hold the fresh water. The water tank can be manually and/or automatically filled when determined to be completely or partially empty. In certain embodiments, the filling of the water tank can be controlled via one or more sensors, values, control units, power sources such as a battery source and/or a simple HMI interface.

In some embodiments, the water provided to the fluid preparation system is purified and/or heated. The purification and/or heating of the water can be performed within the fluid preparation system 1210 and/or before being provided to the fluid preparation system 1210. For example, the water can be heated to about 36.7° C. or about 37° C. In certain embodiments, the water can be re-circulated through a heating system depending on the initial water temperature to reach a target temperature. The purified and/or heated water can be mixed with a premixed concentrated fluid comprising one or more components of the synthetic or simulated amniotic fluid. For example, in some embodiments, the premixed concentrated fluid can be provided in the form of one or more cartridges. The contents of the premixed concentrated fluid can mixed in the purified and/or heated water via a metering pump to form an amniotic bath fluid.

The amniotic bath 1206 can be configured to be filled with synthetic or simulated amniotic fluid. The level and/or temperature of the bath fluid can be monitored during and/or after a filling process of the bath. In certain embodiments, after filling, a heater located adjacent to the bath can be configured to maintain a desired fluid temperature. For example, in certain embodiments, the bath can comprise and/or be configured to be used in conjunction with one or more temperature sensors and/or a thermostat feedback mechanism. The bath can be maintained at a temperature of about 37° C. In certain embodiments, the operator can adjust the temperature of the bath lower than about 37° C., for example in case of hyperthermia and/or risk of hyperthermia. As an example, the temperature of the bath can be set at about 36.5° C., about 36° C., about 35.5° C., about 35.0° C. and/or even lower levels, such as about 30° C., about 25° C., and/or about 20° C. if induced hypothermia is desired medically. In contrast, the operator can adjust the temperature of the bath above about 37° C., for example in case of hypothermia and/or risk of hypothermia. As an example, the temperature of the bath can be set at about 37.5° C., about 38° C., about 38.5° C., about 39.0° C. and/or even higher levels, such as about 40° C., about 41° C., and/or about 42° C. if induced hyperthermia is desired medically.

In certain embodiments, a temperature sensor can also be placed on the infant, for example on the scalp to monitor human body temperature. The monitored human body temperature can be utilized in a feedback mechanism and be transmitted to the main unit for alarms in case of body temperature fluctuations.

Further, in certain embodiments, the water level of the bath can be continuously, constantly, and/or periodically monitored to ensure that the infant is not completely submerged in the bath. In certain embodiments, the system comprises one or more safety harness mechanisms built into the cover to protect infant from accidental submersion. Also, in some embodiments, one or more fluid sensors can be configured to be placed near the infant's head to determine and alarm a user if fluid is detected. For example, in certain embodiments, the one or more fluid sensors can be worn around the infant's neck in the form of a necklace.

In certain embodiments, when the system determines that the water level is above a predetermined level and/or the infant is submerged in the fluid or about to, for example from the one or more fluid sensors or detected failure of the harness system, the system can be configured to sound or display an alarm to a nurse and/or automatically drain the bath fluid completely or partially.

In some embodiments, excess and/or undesired fluid from the fluid preparation and/or bath can be drained with drain lines into a wastewater tank 1208. In certain embodiments, the wastewater tank 1208 can be directly or indirectly connected to a sewer line for wastewater disposal 1214, for example through a flushing mechanism. In some embodiments, the wastewater tank 1208 can be disconnected from the system and main assembly for content disposal. For example, the wastewater tank 1208 can be rolled to a nearby wastewater drain by the staff. For draining the wastewater, a pump and control unit with simple HMI interface can be used with power through a rechargeable battery in certain embodiments.

Fluid Preparation Subsystem

Figure 13:
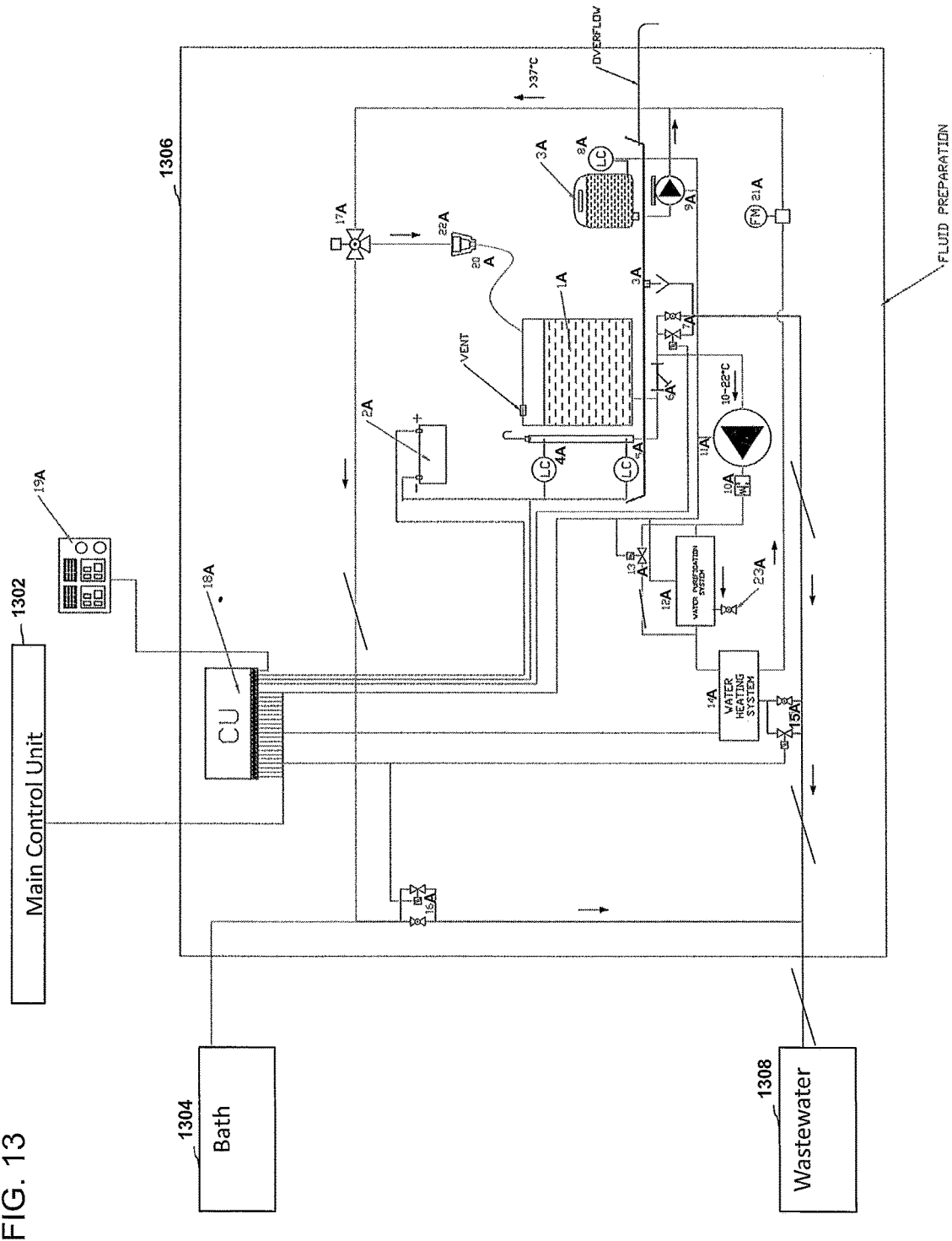
FIG. 13 is a block diagram depicting an embodiment of a fluid preparation sub-system of an amniotic bath incubator system for premature infants.

FIG. 13 is a block diagram depicting an embodiment of a fluid preparation sub-system of an amniotic bath incubator system for premature infants. In some embodiments, a fluid preparation subsystem 1306 comprises one or more fresh water tanks 1A. The fresh water tank 1A can comprise a disposable and/or replaceable cover. The cover can be sterile in some embodiments. In certain embodiments, the fresh water tank 1A is configured to be filled with a hose attached to faucet with slip-on fitting 9A. The fresh water tank 1A can be configured to be directly and/or indirectly connected to a water supply. In certain embodiments, the fresh water tank 1A can be non-disposable and/or non-replaceable. The fresh water tank 1A can be configured to be disinfected along with other non-disposable and/or non-replaceable components of the system that are in contact with water, synthetic amniotic fluid, cartridge fluid, and/or patient or infant.

In certain embodiments, one or more water level sensors 3A, 4A, and 5A can be provided in a fluid preparation subsystem 1306. The one or more water level sensors 3A, 4A, and 5A can be configured to measure the water level in the tank during a fill process.

In some embodiments, during a tank fill, the fluid preparation subsystem 1306 is detached from the main system. In certain embodiments, the fluid preparation subsystem 1306 does not need to be detached from the main system during a tank fill. The fluid preparation subsystem 1306 can comprise one or more power supplies, such as a rechargeable battery 2A.

In some embodiments, one or more level sensors 4A of the fluid preparation subsystem 1306 are configured to trigger an alarm that the faucet needs to be closed when the tank 1A is full or is near full. In certain embodiments, a water supply is automatically closed when one or more level sensors 4A of the fluid preparation subsystem 1306 detect that the tank 1A is full, near full, and/or at, above, and/or below a predetermined level.

In certain embodiments, if the water level continues to rise above the capacity of the fresh water tank 1A, for example either because an operator or nurse does not close the faucet valve or if the system fails to automatically close the faucet valve, overflow positioned on the top of fresh water tank 1A can discharge additional water from the tank through one or more drain openings 3A out of the system.

In some embodiments, a system disinfection process can be performed periodically and/or continuously. For example, in certain embodiments, system disinfection is performed continuously by allowing disinfection fluid to continuously pass through the system. In some embodiments, system disinfection is performed periodically by allowing disinfection fluid to pass through the system or portions thereof at certain periods, for example when the patient or infant is placed out of the amniotic incubator. Periodic system disinfection can be performed periodically according to a predetermined schedule and/or as needed or convenient, for example when the infant or patient is placed out of the amniotic incubator.

In some embodiments, system disinfection can be performed by inserting a cartridge with concentrated disinfection fluid. For example, a disinfection cartridge 3A may be placed instead of a concentrated amniotic bath fluid cartridge. The contents of the disinfection cartridge 3A can be dissolved in the water and allowed to pass through the system. For example, fresh water can be pumped by one or more pumps 11A via a bypass valve 13A and further into a water heating system 14A. In some embodiments, a disinfection cartridge 3A and one or more amniotic bath fluid cartridges can be color coded using different colors and/or other markings for differentiation between the two. As such, in some embodiments, an operator or nurse can visually notice and/or determine that a correct cartridge has been installed. In certain embodiments, the disinfection can be colored, for example red, orange, yellow, blue, purple, or the like. As such, in certain embodiments, an operator or nurse can easily and/or immediately determine visually if disinfection fluid, or a small amount of disinfection fluid, reaches the amniotic bath while the patient or infant is placed in the bath. In some embodiments, the disinfection cartridge can comprise a shape that is different from that of an amniotic bath fluid cartridge. For example, the disinfection cartridge can comprise a small bump-tab that can be configured to trigger an electro-mechanical sensor. The electro-mechanical sensor, once triggered, can be configured to transmit a signal to a control unit that a disinfection cartridge has been installed. In some embodiments, the control unit can be configured to prevent filling of the amniotic bath until all pre-requirements, such as disinfection, are fulfilled. In certain embodiments, after the disinfection procedure is completed, the system can be washed from remnants of disinfection fluid by being washed by fresh, heated, and/or unheated water through all or a portion of the components of the system that were in contact with the disinfection fluid.

In certain embodiments, the system comprises one or more metering or dosing pumps 9A to add a controlled amount of concentrated disinfection fluid to the water line to allow for controlled continuous mixing. In some embodiments, concentrated disinfection fluid can be dissolved via a batch process.

The mixed disinfection fluid can be returned to the fresh water tank 1A through one or more valves 17A to disinfect the water tank 1A. For example, the mixed disinfection fluid can pass through a return line through one or more connected slip on fittings 20A, 22A. Other portions of the system can be disinfected by pumping the mixed disinfection fluid from fresh water tank 1A making necessary loops to reach all or one or more tubes, fitting and equipment in contact with bath fluid and water. After the disinfection process, remaining fluid can be drained from the system through one or more valves 7A, 15A, 16A, 117A, 119A and 120A into the wastewater tank 203A and the fresh water tank 1A can be disposed. The one or more slip-on fittings 20A, 22A can be configured to be connected only during the disinfection process.

Amniotic Bath Subsystem

Figure 14:
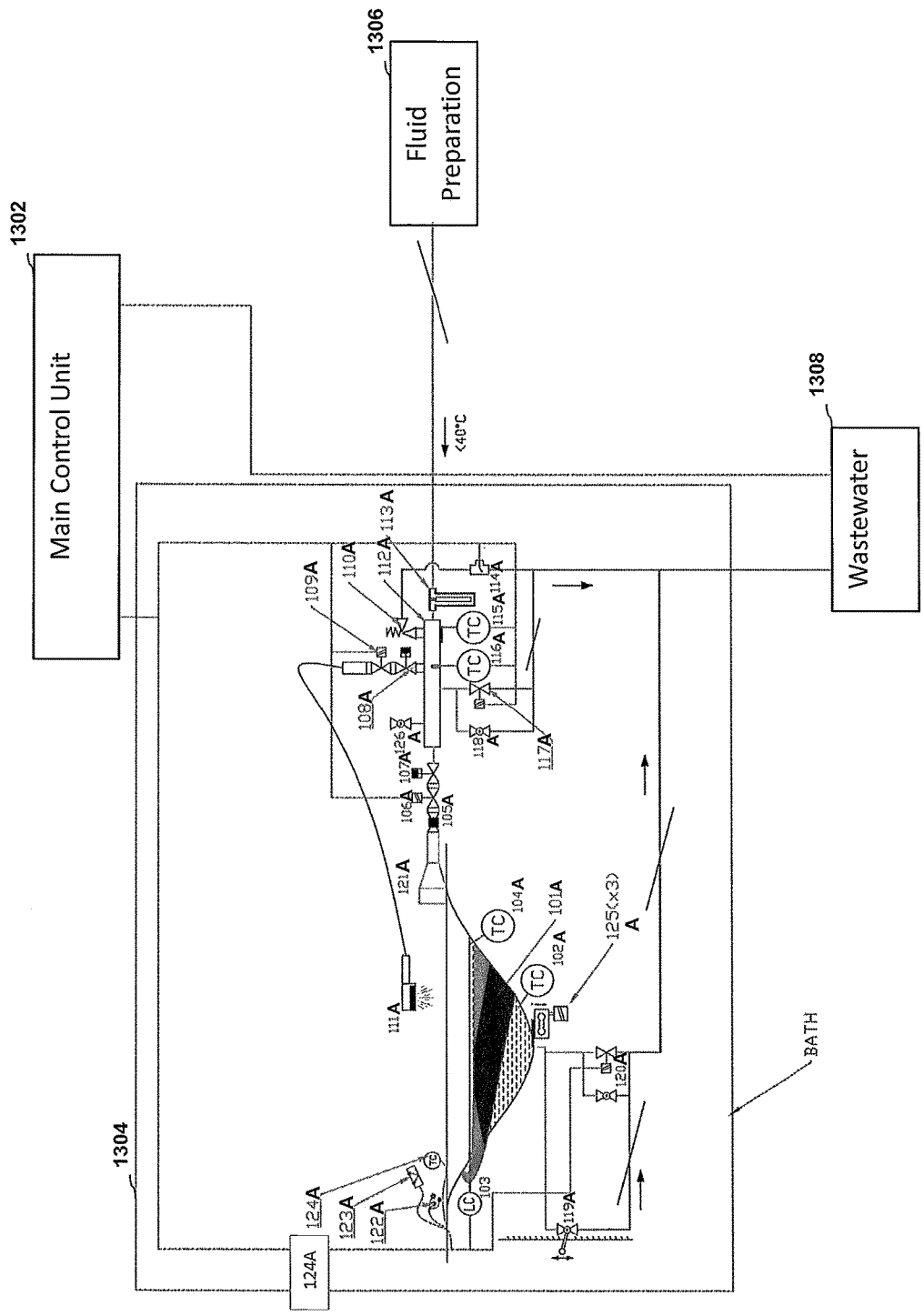
FIG. 14 is a block diagram depicting an embodiment of a bath sub-system of an amniotic bath incubator system for premature infants.

FIG. 14 is a block diagram depicting an embodiment of a bath sub-system of an amniotic bath incubator system for premature infants.

In some embodiments, the amniotic bath may be changed periodically or continuously. To do so, an operator may initiate bath fluid change using a user interface 1202. In some embodiments, water from a fresh water tank 1A can flow through a strainer 6A to remove large impurities. One or more pumps 10A of the fluid preparation subsystem can be configured to pump water through a water purification system 12A which can remove organic and nonorganic impurities. In some embodiments, the water purification system 12A can be external from the amniotic bath incubator system and/or serve as constant water supply. In such embodiments, a fresh water tank 1A may or may not be used. In some embodiments, a central water purification system may serve as constant water supply. Also, in such embodiments, the fresh water tank 1A may or may not be used.

After the water purification process, water can be pumped through a heating system 14A, which can be configured to heat the water to a required temperature, such as about 37 C. In some embodiments, a metering pump 9A can add pre-mixed fluid from one or more amniotic fluid cartridges 3A to water. The mixing can be performed in a batch process in some embodiments. In certain embodiments, in-pipe mixing occurs to form the amniotic bath fluid. In some embodiments internal, an external or central water purification system may supply preheated water. In such embodiments, a heating system 14A may or may not be used to heat water to a required or predetermined temperature, depending on the output temperature of the water purification system. In some embodiments, one or more temperature sensors can be provided to detect the temperature of the purified water. The heating system 14A can be automatically controlled to heat the water to a required or predetermined temperature based on the detected current temperature.

The pre-mixed fluid in the cartridge 3A can comprise one or more electrolytes, minerals, pharmaceuticals, proteins, peptides, lipids, lactate, pyruvate, enzymes, hormones, antibodies, amniotic stem cells and/or other cellular material. In certain embodiments, one or more pharmaceuticals or other desired compounds can also be added to the amniotic bath fluid, for example manually and/or through the same and/or additional cartridge comprising such components. More specifically, in some embodiments, a single cartridge can comprise one or more of any of the synthetic amniotic fluid components discussed herein, for example at concentrated levels. In other embodiments, a plurality of cartridges, for example 2, 3, 4, 5, 6, 7, 8, 9, or 10 cartridges, can comprise one or more of the synthetic amniotic fluid components discussed herein.

Mixing proportions for the amniotic bath fluid can be determined by a flow rate measurement of the fresh water by one or more flow meters 21A. The mixed amniotic bath fluid can reach a manifold 112, in some embodiments, after passing through one or more valves 17A and/or being sterilized by one or more UV sterilizing units 113A.

In some embodiments, the fluid temperature can be measured with one or more temperature sensors 116A. If temperature is not adequate, for example below 37° C., the manifold 112A can be drained via one or more valves 117A. In case of the failure of the temperature control system, an anti-scald valve 107 can be provided to prevent fluid from reaching the bath. In case of overpressure, for example if the temperature is too high and the one or more drain valves 117A fails to open, one or more safety valves 110A can be provided in the system. The one or more safety valves 110A may open to release the fluid into a drain line. In certain embodiments, a flow switch 114A can be configured to trigger an alarm indicating that the one or more safety valves have moved to an open position.

When the fluid temperature, as measured by the one or more temperature sensors 116A, is at required level, such as at 37° C., one or more valves 106A may open to allow the amniotic bath fluid to flow into the bath. In contrast, when fluid temperature, as detected by the one or more temperature sensors 116A, is outside of a certain predetermined range, such as outside of a range between about 35° C. to about 39° C. or outside of a range between about 36° C. to about 38° C., the one or more valves 106A can be configured to automatically close, thereby preventing the amniotic bath fluid from flowing into the bath. In certain embodiments, the fluid is configured to flow into the bath through one or more filters 115A and/or divergent nozzles 121A. Divergent nozzles can be used to prevent splashing and thereby allowing rapid filling of the bath with the synthetic or simulated amniotic fluid, for example at rates between about 0.1 liters/sec to about 0.2 liters/sec. In certain embodiments, one or more divergent nozzle check valves may be installed to prevent backflow from the bath into the tubing system. In some embodiments, the one or more divergent nozzles can be disposable. In certain embodiments, a hose attaching the one or more divergent nozzles to the tubing system or manifold can comprise a special fitting, configured to open a safety check valve attached to the system when the fitting is attached to the tubing system. The safety check valve can be configured to prevent outflow of the fluid from the tubing system in case a divergent nozzle is not installed and/or is not properly secured to the tubing system with the special fitting.

In certain embodiments, if the fresh water tank 1A does not have enough water to allow for an amniotic fluid bath change, the system can be configured to trigger an alarm to prevent the bath change until the fresh water tank 1A is refilled. If one or more sensors 8A detect that one or more cartridges are empty, the system can also be configured to trigger an alarm to prevent bath change until the one or more cartridges are replaced. Once the bath is refilled, one or more drain valves 7A, 15A, 16A, 120A can be configured to be opened to drain the tubing from any remaining bath fluid or water.

In some embodiments, the amniotic bath subsystem 1304 comprises a rinsing system for rinsing an infant. In certain embodiments, a rinsing system 111A is supplied with the bath fluid through a manifold 112A in a similar manner as the bath. If the user desires to use the rinsing system 111A, in some embodiments, the user can select a rinsing option from a user interface, such as an HID interface. In some embodiments, one or more temperature sensors 116A can be configured to detect the temperature of the fluid. In certain embodiments, if the temperature of the fluid is at a desired temperature, such as 37° C. for example, one or more valves 109 can be configured to open and a hose can supply the rinsing system 111A with the bath fluid. If the detected temperature is too high, such as above 37° C., an anti-scald valve 108A can be configured to close, thereby preventing the fluid from flowing to the rinsing system 111A. In some embodiments, a rinser can comprise a trigger device, which can be connected to a shut-off valve. For example, in certain embodiments, a user or operator may have to push the trigger in order to open a valve when holding the rinser handle to prevent accidental splashing of the patient/infant and/or equipment.

In some embodiments, the amniotic bath incubator system or device or amniotic bath subsystem thereof comprises a cover or liner configured to be placed over the bath when emptied. The cover or liner can be sterile and/or disposable for infection control. The cover or liner can also comprise a safety harness built onto the cover to prevent accidental submersion of the infant. The cover or liner is not disposable in certain embodiments. The cover or liner, whether disposable or non-disposable, can comprise a variety of shapes and/or sizes to fit a variety of infants and/or patients.

The amniotic bath can be ergonomically designed to allow anatomic fetal positioning of the infant with its neck and head above the water level. In some embodiments, slip-on and/or sterile plastic covers can be used to protect an umbilical catheter(s) and/or other peripheral or central lines from exposure to the bath water. Anchors can be provided and/or built above the water level to hold the umbilicus above the water level to prevent exposure of a catheter line(s) to fluid. Anchors and/or umbilical catheter bridges can also be built above the face of the infant to hold one or more catheters, leads, wires, and/or tubings in place and to prevent accidental kinking. Cardiac leads 122A, oximeter, and/or skin temperature sensors can be placed on the infant neck and/or scalp to prevent exposure to the bath fluid. In some embodiments a cap, hat, or helmet can be configured to be placed on the patient or infant's head. The cap, hat, or helmet can be configured to incorporate one or more or all instruments, sensors, and/or equipment into a single unit that can be secured on the head of the infant or patient.

In some embodiments, the system can comprise one or more valves 23A, 126A for water and/or bath fluid sampling. For example, one or more valves 23A, 126A can be used to sample the water and/or bath fluid periodically to check the contents and/or temperatures thereof.

In certain embodiments, sterile techniques, gloves and/or equipment can be used when infant manipulation or contact is necessary. Further, ear and/or eye safety devices can be placed on the infant to minimize exposure to loud noises and/or lights. In certain embodiments, an additional cover(s) for the bath may be used to create a dark and quiet environment for the infant. In some embodiments the cap, hat, or helmet can be configured to incorporate eye and/or ear protection elements into a single unit that can be secured on the head of the infant or patient.

In some embodiments, the temperature of the bath fluid in the bath can be measured by one or more temperature sensors 102A, 104A. Further, in certain embodiments, the temperature of the bath fluid in the bath can be maintained at a desired temperature, such as 37° C., by one or more heaters 101A. In normal operation, the level of the bath can be controlled by a manual, semi-automated, or automated level regulator 119A. In certain embodiments, one or more additional temperature sensors 124A can be placed on the infant skin to measure body temperature. In some embodiments, the cap, hat, or helmet can comprise one or more temperature sensors for measuring the body temperature of the infant or patient. Further, one or more alarms can be configured to be activated in case of hyperthermia or hypothermia of the infant based on the detected body temperature.

In some embodiments, it can be advantageous to determine the weight of the infant periodically, for example on-demand, and/or continuously. As such, in certain embodiments, weight of the infant can be measured using a load cells unit system 125A, for example with three or more support points. A weight measurement system can be configured to measure the infant's weight, for example by subtracting known weights of the incubator elements and fluids inside the bath from the total weight measured. In certain embodiments, one or more solenoid actuators can be configured to make very slight movements of about 1-2 mm or 0.04-0.08 inches in order to transfer the weight of the measured elements and infant from the incubator support to load cells. After the weight measurement process is completed, solenoid actuators can be configured to return to their initial position, transferring weight back to the incubator support. In some embodiments, the weight measurement procedure of the infant can comprise removing the infant from the incubator, resetting or zeroing the weight system, and returning the infant for measurement.

It can be critical to ensure that the infant is not submerged in the amniotic bath fluid. Accordingly, in some embodiments, a fluid detector is provided in the form of a necklace sensor 103A to be worn by the infant. In some embodiments, in case that a critical level in the bath is reached and the necklace sensor 103A is immersed, an alarm can be triggered and/or automatic draining of the bath can be conducted by opening one or more valves 120A. In case the temperature of the bath is above a desired temperature, such as 37° C., an alarm can also be triggered and/or automatic draining of the bath can be conducted by opening one or more valves 120A. In case the temperature of the bath drops below a desired temperature, such as 37° C., an alarm can also be triggered and/or automatic draining of the bath can be conducted by opening one or more valves 120A. In certain embodiments, in both cases of abnormal temperature, a bath fluid change procedure can be partly initiated automatically and can halt after heating the bath fluid to a desired temperature and/or wait for operator confirmation to continue through mixing and/or fluid delivery to the bath. In some embodiments, an adapter can be used to position an infant in a manner that its head and/or mouth/nose are always above the maximum level of the amniotic bath fluid. In such embodiments, the bath can be filled to its maximum level, while the position of the infant can be changed depending on a selected adapter. In certain embodiments, the adapter can be positioned in the bath and covered with the disposable cover, to provide adequate treatment of smaller sized infants.

Wastewater Tank Subsystem

Figure 15:
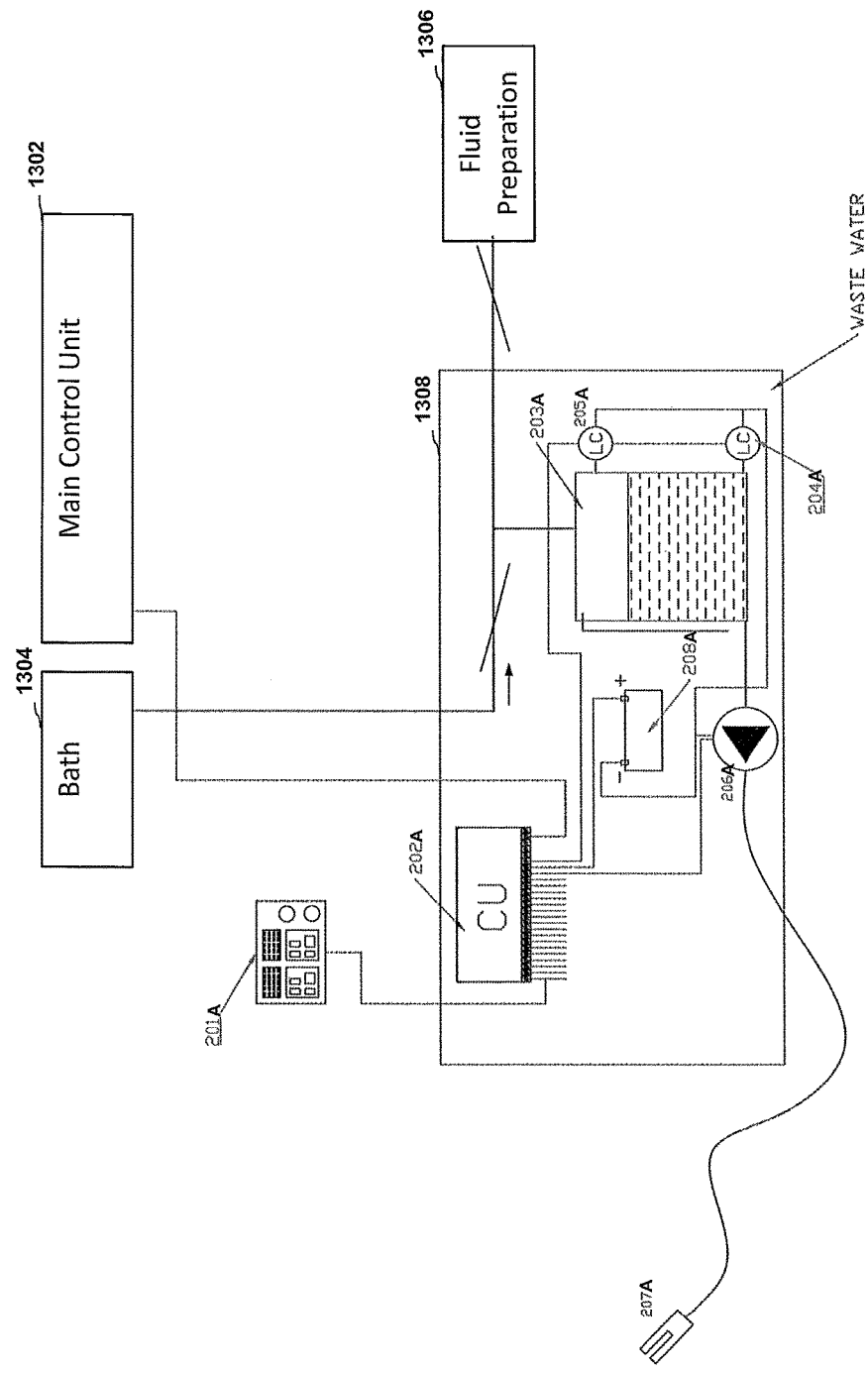
FIG. 15 is a block diagram depicting an embodiment of a wastewater sub-system of an amniotic bath incubator system for premature infants.

FIG. 15 is a block diagram depicting an embodiment of a wastewater sub-system of an amniotic bath incubator system for premature infants. All wastewater from the fluid preparation and/or bath subsystems can be collected in a wastewater tank 203A. A determined high and/or low level of fluid in the wastewater tank can be measured by one or more sensors 205A. In some embodiments, if the wastewater tank is full, an alarm can be triggered to prevent change of the bath fluid until the contents of the wastewater tank 203A are discharged. When discharging, the wastewater subsystem can be detached from the rest of the system in some embodiments. In certain embodiments, the wastewater tank 203A can be directly connected to a sewage line and it may not be necessary to detach the wastewater subsystem from the rest of the system for discharging. In such embodiments, a check valve may prevent backflow from the sewage line to the amniotic bath incubator system. The check valve can be configured to be opened by pressure produced by one or more wastewater pumps while discharging.

The wastewater subsystem can comprise a power supply, such as a rechargeable battery 208A. The wastewater can be discharged from the tank by one or more pumps 206A. In certain embodiments, one or more level sensors 204A can be configured to measure a lower level of the tank. When it is detected that the tank is empty, an alarm can be triggered and/or the control unit 202A can halt the pump. In certain embodiments, the wastewater tank 203 comprises an overflow line in case of failure of the control and/or measuring system. In some embodiments, a check valve can be configured to prevent backflow from the sewage line to the amniotic bath incubator system.

Heating Subsystem

Figure 16:
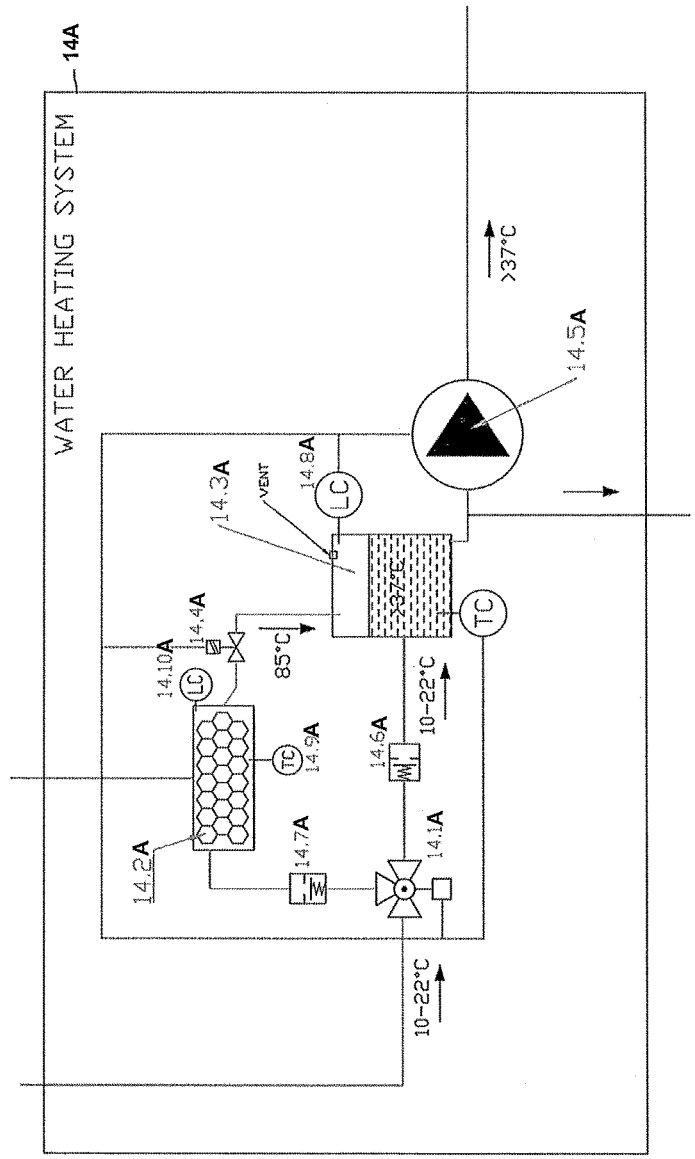
FIG. 16 is a block diagram depicting an embodiment of a water heating sub-system of an amniotic bath incubator system for premature infants.

In some embodiments, the amniotic bath incubator system can comprise one or more heating subsystems of one or more varieties. FIG. 16 is a block diagram depicting an embodiment of a water heating sub-system of an amniotic bath incubator system for premature infants. As shown in FIG. 16, in some embodiments, the system comprises one or more DC waters heaters and/or heated and unheated water can be mixed in the fresh water tank.

More specifically, one or more control valves 14.1 can be configured to open and supply a DC heater 14.2 and/or an AC heater, with fresh water. The water level in the heater can be controlled by one or more level sensors 14.10. In some embodiments, when a desired water level is reached, one or more valves 14.1 can be configured to close. In certain embodiments, when the water is heated to a desired temperature, one or more valves 14.4 can be configured to open and/or discharge water from the heater 14.2.

Figure 17:
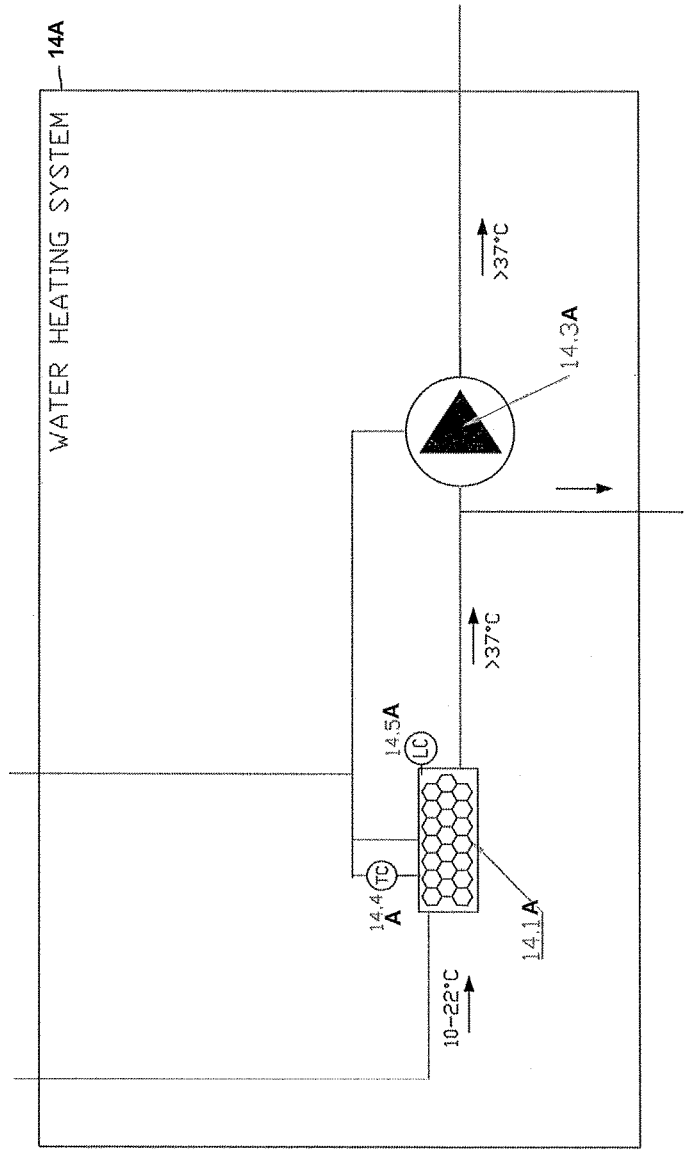
FIG. 17 is a block diagram depicting an embodiment of a water heating sub-system of an amniotic bath incubator system for premature infants.

In some embodiments, the heated water can be configured to partially fill the tank 14.3. The rest of the volume of the tank can be supplied from an unheated water supply, by opening one or more valves 14.1 and filling the tank 14.3 where mixing of the heated and unheated water can occur. The level and/or temperature of the water in the tank 14.3 can be measured by one or more sensors 14.9, 14.10. In certain embodiments, when a targeted temperature, such as 37° C., is reached, a control valve 14.1 can be configured to close and/or one or more pumps 14.5 can be configured to pump the heated water into the system FIG. 17 is a block diagram depicting an embodiment of a water heating sub-system of an amniotic bath incubator system for premature infants. As shown in FIG. 17, in some embodiments, the system comprises one or more AC or DC waters heaters but does not comprise mixing of heated and unheated water in the fresh water tank.

In some embodiments, one or more heaters 14.1 can be supplied with water from the system. The level and/or temperature of the water can be measured with one or more sensors 14.4, 14.5 and can be controlled by one or more system pumps and/or drainage valves. When a desired temperature is reached, one or more pumps 14.3 can be configured to pump the water into the system without further mixing.

Figure 18:
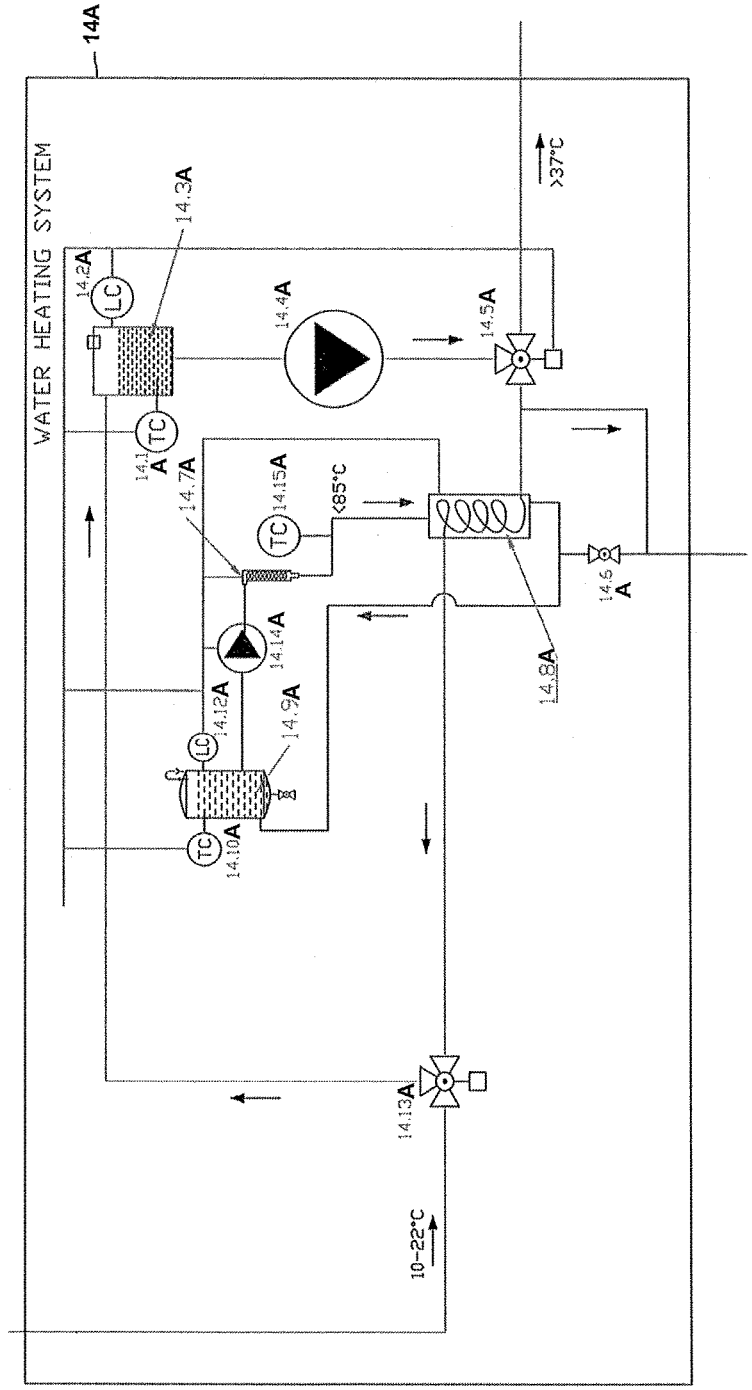
FIG. 18 is a block diagram depicting an embodiment of a water heating sub-system of an amniotic bath incubator system for premature infants.
Figure 18A:
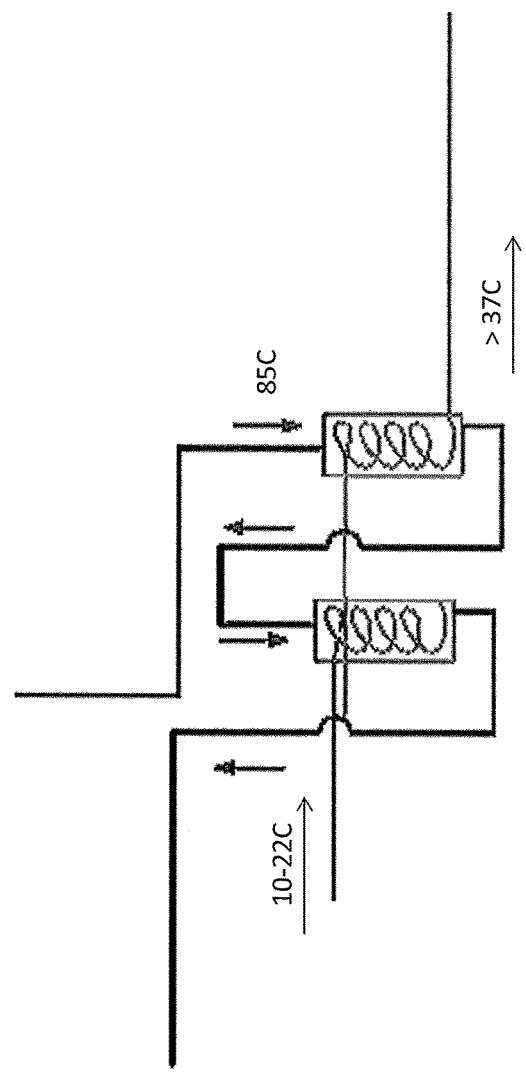
FIG. 18A is a block diagram depicting an embodiment of a water heating sub-system of an amniotic bath incubator system for premature infants.

FIG. 18 is a block diagram depicting an embodiment of a water heating sub-system of an amniotic bath incubator system for premature infants. As shown in FIG. 18, in some embodiments, the system comprises one or more AC or DC water heaters with one or more heat exchangers. In embodiments comprising more than one heat exchanger, the one or more heat exchangers can be connected in parallel or serial line. For example, in some embodiments, the system can comprise two heat exchangers in a serial connection as illustrated in FIG. 18A. In certain embodiments, the system can comprise more than two heat exchangers to shorten the heat-up time.

In some embodiments, one or more valves 14.13 can be configured to supply a fresh water tank 14.3 with water. The level and/or temperature of the water in the tank can be controlled by one or more sensors 14.1, 14.2. When the tank is filled to a required level, one or more pumps 14.4 can be configured to start circulating water through a heat exchanger 14.8 via one or more valves 14.5, 14.13. When the water temperature reaches a desired level, one or more valves 14.5 can be configured to break a loop and/or one or more pumps 14.4 can be configured to pump water into the system.

In certain embodiments, a heat exchanger primary circuit of the system can comprise one or more circulating pumps 14.14 configured to pump fluid through an AC or DC heater or electric heat exchanger 14.7, and back into a collection tank 14.9. The temperature of the water in the tank can be measured before reaching the heat exchanger by one or more temperature sensors 14.10, 14.15. Based on the detected temperature of the water in the tank 14.3 and/or the heat exchanger primary circuit fluid temperature, the heater 14.7 can be configured to be switched on or off.

Computer System

Figure 19:
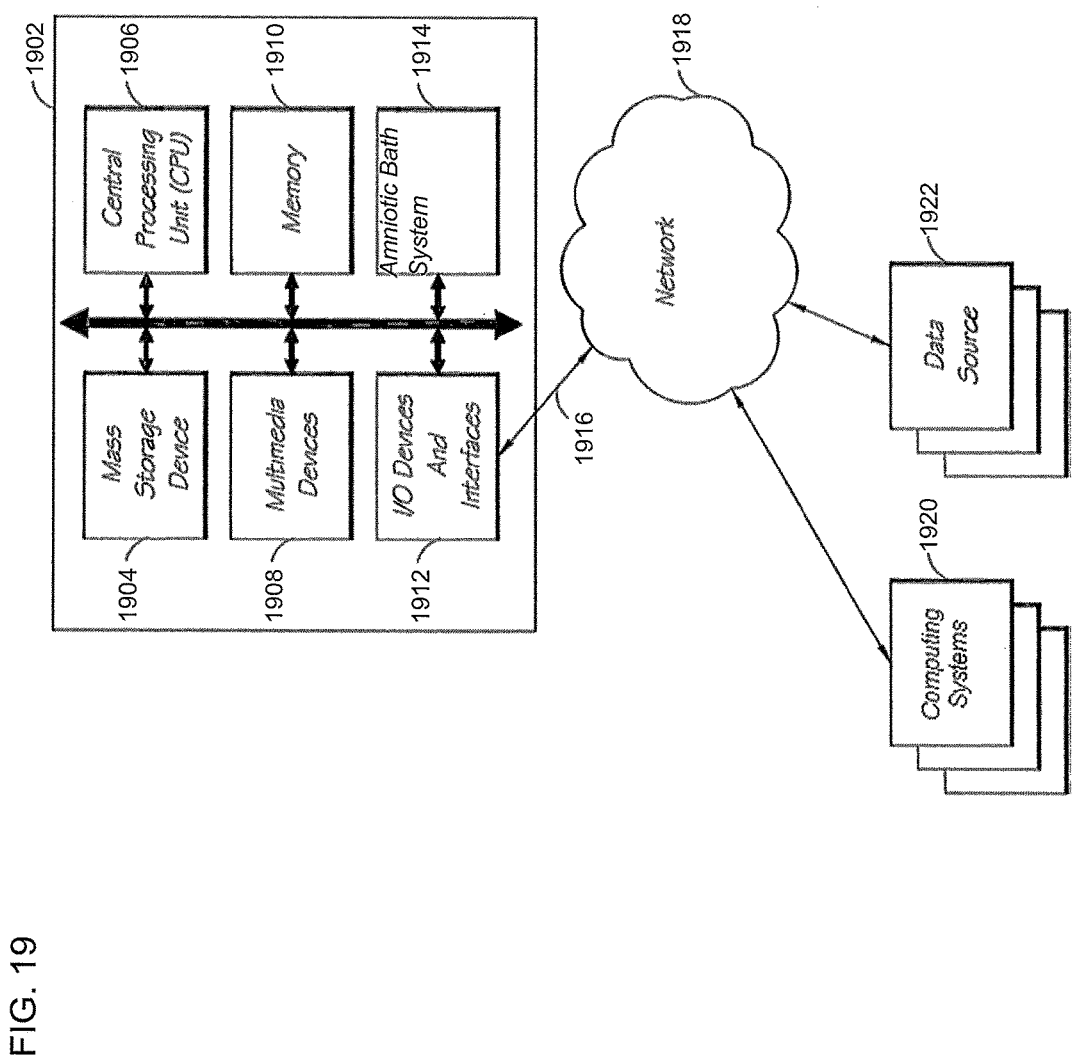
FIG. 19, 19A-B are block diagrams depicting an embodiment of a computer hardware system configured to run software for one or more embodiments of the amniotic bath incubator systems, devices, and methods.
Figure 19A:
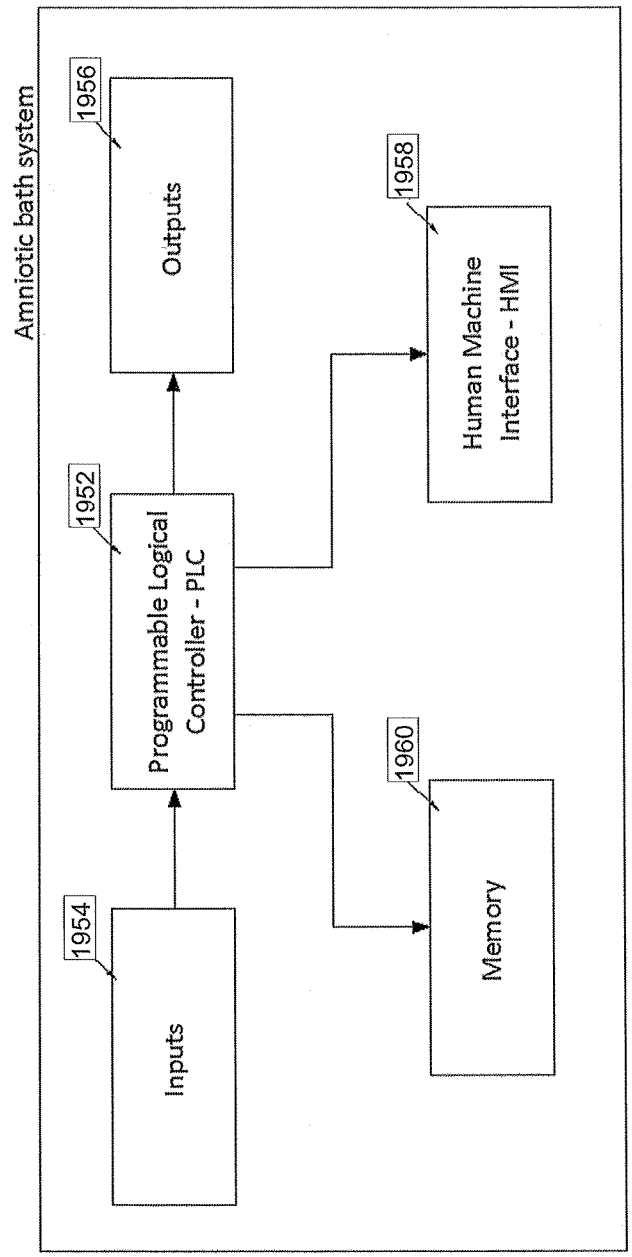
Figure 19B:
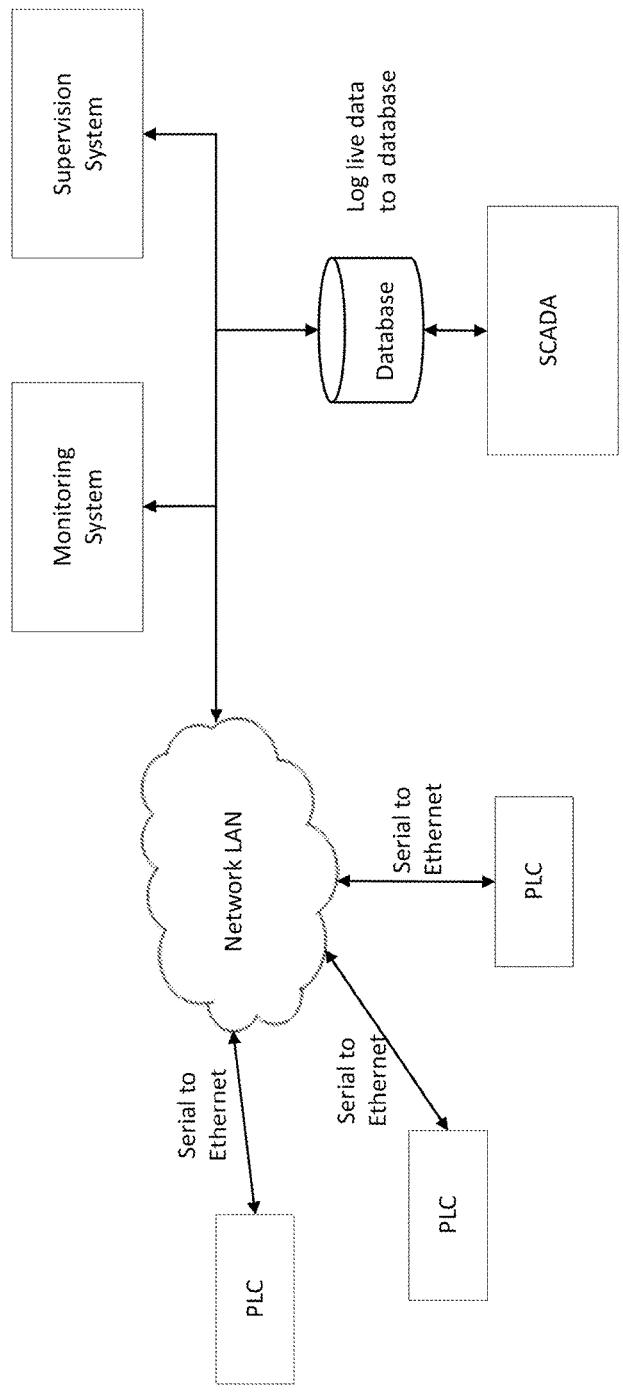

In some embodiments, the systems, processes, and methods described herein are implemented using a computing system, such as the one illustrated in FIG. 19, FIG. 19A, and/or FIG. 19B. The example computer system 1902 is in communication with one or more computing systems 1920 and/or one or more data sources 1922 via one or more networks 1918. While FIG. 19 illustrates an embodiment of a computing system 1902, it is recognized that the functionality provided for in the components and modules of computer system 1902 may be combined into fewer components and modules, or further separated into additional components and modules.

Amniotic Bath System Module

The computer system 1902 can include an Amniotic Bath Incubator System 1914 that carries out the functions, methods, acts, and/or processes described herein. The Amniotic Bath Incubator System 1914 can be executed on the computer system 1902 by a central processing unit 1910 discussed further below.

In certain embodiments, as illustrated in FIGS. 19A and 19B, a Programmable Logical Controller PLC 1952 can be an integral part of the Amniotic Bath Incubator System 1914 that carries out the functions, methods, acts, and/or processes described herein. The Amniotic Bath Incubator System 1914 can be executed as a PLC program. The PLC can be configured to control all input and output devices as shown in FIG. 19A. The input devices 1954 shown in FIG. 19A can comprise all sensors. The output devices 1956 shown in FIG. 19A can comprise valve actuators, solenoid valve actuators, solenoid actuators, heaters, and/or pumps. In some embodiments, the Human Machine Interface or HMI 1958 can comprise a touchscreen GUI device configured to be used by a nurse or operator of the amniotic bath incubator system. In certain embodiments, instead of and/or in combination with a touchscreen GUI device, one or more LED, LCD, or other displays may be used, as well as light and/or sound indicators. The memory module 1960 can be configured to store executable programs and process data.

In some embodiments, a plurality of amniotic bath incubators can be configured to be controlled by a single PLC device as shown in FIG. 19B. More specifically, a plurality of amniotic bath incubators can be controlled by a single PLC device through a Supervisory Control and Data Acquisition (SCADA) system. In certain embodiments, process data can be stored in a database. Monitoring and/or supervision can be conducted from a network, locally and/or from a remote position. For example, in certain embodiments, a nurse or operator can monitor multiple incubators on single display device positioned inside the NICU unit.

In general the word "module," as used herein, refers to logic embodied in hardware or firmware or to a collection of software instructions, having entry and exit points. Modules are written in a program language, such as JAVA, C or C++, Ladder diagram (LD), Sequential Function Charts (SFC), Function Block Diagram (FBD), Structured Text (ST), Instruction List (IL), or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

Computing System Components

The computer system 1902 includes one or more processing units (CPU) 1910, which may include a microprocessor. The computer system 1902 further includes a physical memory 1912, such as random access memory (RAM) for temporary storage of information, a read only memory (ROM) for permanent storage of information, and a mass storage device 1904, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1902 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1902 includes one or more input/output (I/O) devices and interfaces 1908, such as a keyboard, mouse, touch pad, and printer. The I/O devices and interfaces 1908 can include one or more display devices, such as a monitor, that allows the visual presentation of data to a user. More particularly, a display device provides for the presentation of GUIs as application software data, and multi-media presentations, for example. The I/O devices and interfaces 1908 can also provide a communications interface to various external devices. The computer system 1902 may include one or more multi-media devices 1906, such as speakers, video cards, graphics accelerators, and microphones, for example.

Computing System Device/Operating System

The computer system 1902 may run on a variety of computing devices, such as a server, a Windows server, a Structure Query Language server, a Unix Server, a personal computer, a laptop computer, and so forth. In other embodiments, the computer system 1902 may run on a cluster computer system, a mainframe computer system and/or other computing system suitable for controlling and/or communicating with large databases, performing high volume transaction processing, and generating reports from large databases. The computing system 1902 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 1902 illustrated in FIG. 19 is coupled to a network 1918, such as a LAN, WAN, or the Internet via a communication link 1916 (wired, wireless, or a combination thereof). Network 1918 communicates with various computing devices and/or other electronic devices. Network 1918 is communicating with one or more computing systems 1920 and one or more data sources 1922. The Amniotic Bath Incubator System 1914 may access or may be accessed by computing systems 1920 and/or data sources 1922 through a web-enabled user access point. Connections may be a direct physical connection, a virtual connection, and other connection type. The web-enabled user access point may include a browser module that uses text, graphics, audio, video, and other media to present data and to allow interaction with data via the network 1918.

The output module may be implemented as a combination of an all-points addressable display such as a cathode ray tube (CRT), a liquid crystal display (LCD), a plasma display, or other types and/or combinations of displays. The output module may be implemented to communicate with input devices 1908 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

Other Systems

The computing system 1902 may include one or more internal and/or external data sources (for example, data sources 1922). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1902 also accesses one or more databases 1922. The databases 1922 may be stored in a database or data repository. The computer system 1902 may access the one or more databases 1922 through a network 1918 or may directly access the database or data repository through I/O devices and interfaces 1908. The data repository storing the one or more databases 1922 may reside within the computer system 1902.

Bath Fluid Change and Rinsing

Figure 20A:
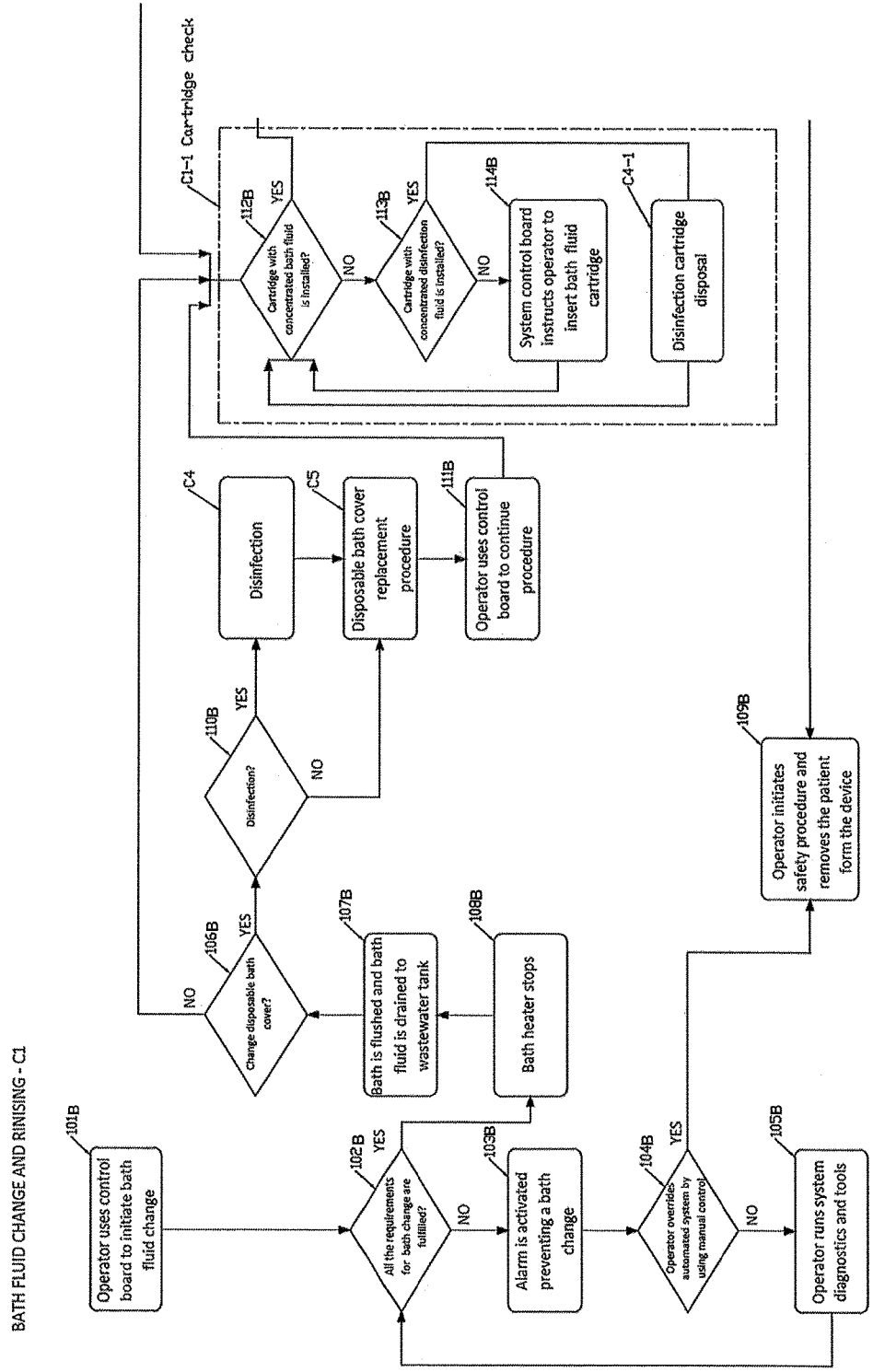
FIGS. 20A-B are block diagrams depicting one or more embodiments of changing and rinsing bath fluid of an amniotic bath incubator system for premature infants.
Figure 20B:
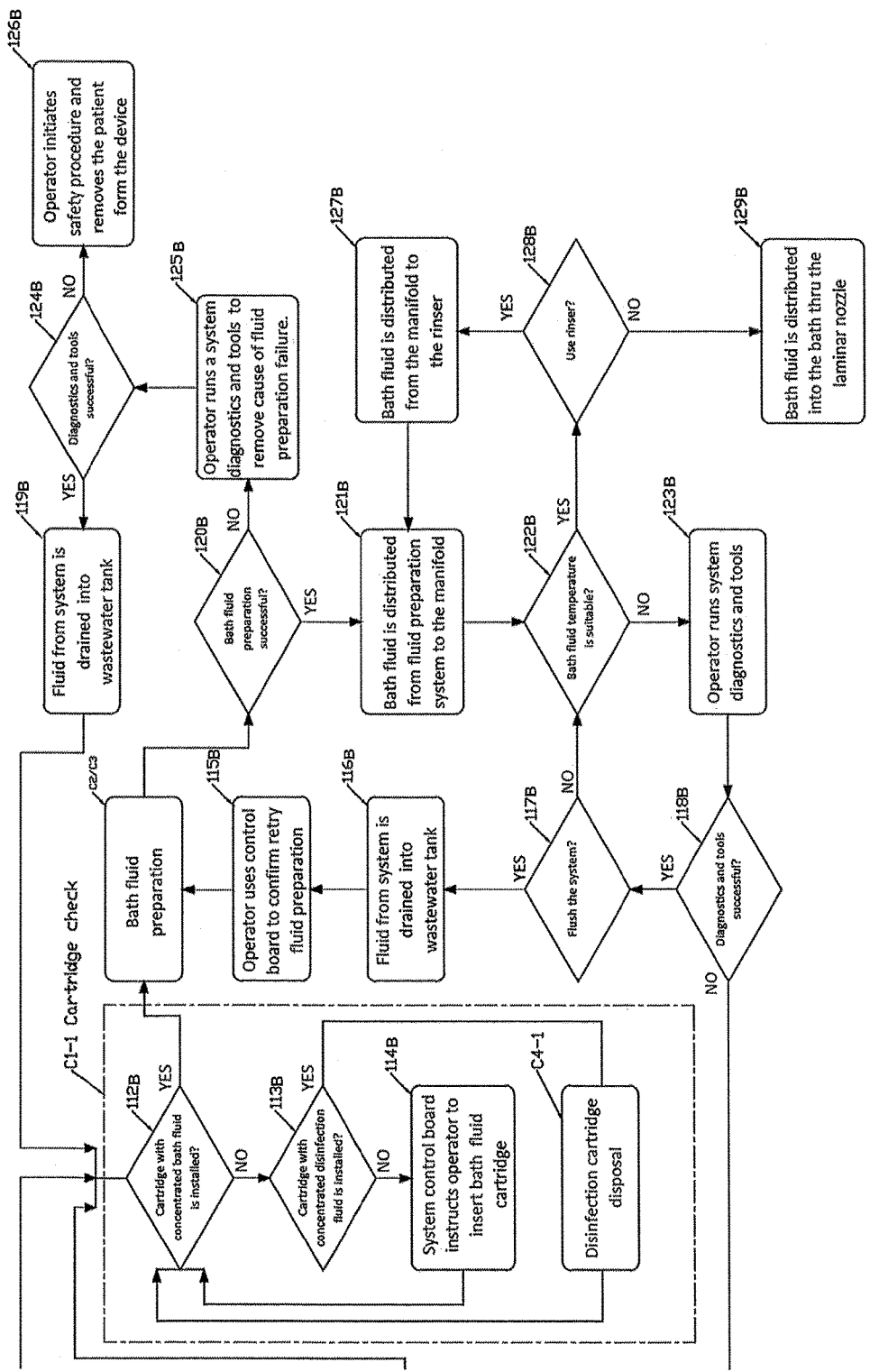

FIGS. 20A-B are portions of a single block diagram depicting one or more embodiments of changing and/or rinsing bath fluid of an amniotic bath incubator system for premature infants.

In some embodiments, at block 101B, an operator can use a control board to initiate a bath fluid change. For example the operator can be a nurse or other health provider. Once the operator initiates the bath fluid change, the system can be configured to determine if all the requirements for bath change are fulfilled at block 102B. Such requirements can comprise, for example determining whether concentrated bath fluid cartridge is present and/or whether the wastewater tank is full. If a concentrated bath fluid cartridge is not present, the system can be configured to determine that not all the requirements for a bath change are fulfilled. Similarly, if the wastewater tank is full, the system may determine that not all of the requirements for a bath change are fulfilled.

In embodiments where the system comprises an internal water treatment unit, the system can be configured to determine whether the fresh water tank is empty and/or whether the water temperature in the tank is at a required level. For example, if the system determines that the fresh water tank is empty and/or that the water temperature in the tank is not at the required level, the system can determine that not all the requirements for a bath change are fulfilled. In other embodiments where the system comprises an external water treatment unit, the system can be configured to determine whether the external water treatment unit is able to produce purified water and/or heating of the purified water. For example, if the external water treatment unit returns a positive signal that it is able to produce purified water and/or its heating units are functioning correctly to allow warming of the fluid to a desired temperature, the system can be configured to determine that all the requirements for a bath change are fulfilled. In certain embodiments, the system can be configured to determine that all the requirements for a bath change are fulfilled when no faults are detected by one or more system sensors. Conversely, if at least one or more system sensors detect and/or provide that one or more faults exists, the system can be configured to determine that not all the requirements for a bath change are fulfilled.

If the system determines that all the requirements for a bath change are fulfilled, the system can be configured to stop a heater for the bath at block 108B. Once the bath heater stops, the bath can be flushed and the bath fluid can be drained to a wastewater tank at block 107B. After the bath fluid is drained, the system can be configured to determine whether the disposable bath cover should be changed at block 106B. If the system determines that the bath cover does not need to be changed, the system can be configured to perform a cartridge check at block C1-1, which will be discussed in more detail below.

In contrast, if the system determines that the disposable bath cover should be changed, the system can be configured to determine whether disinfection should be performed at block 110B. If the system determines that disinfection should be performed, the system can be configured to perform a disinfection process at C4. Particulars of the disinfection process will be described in more detail below. However, if the system determines that disinfection is not necessary, the system can be configured to proceed to a disposable bath cover replacement procedure at C5. Additional details of the disposable bath cover replacement procedure will be discussed in more detail below. If the system determines that the disposable bath cover replacement procedure should be performed, an operator can use the control board to continue the procedure at block 111B, and thereafter perform a cartridge check at block C1-1.

If the system determines that not all the requirements for a bath change are fulfilled at block 102B, an alarm can be configured to be activated preventing a bath change at block 103B. Despite an alarm being activated, the system can comprise an override function. For example, an operator can decide whether to override the automated system by using a manual control at block 104B. If the operator determines not to override the automated system by using a manual control, the operator may decide to run a system diagnostics and tools at block 105B, after which is performed the system can then again determine whether all the requirements for a bath change are fulfilled. If the operator does decide to override the automated system by using a manual control, the operator may decide to initiate a safety procedure and remove the patient or infant from the device at block 109B.

In some embodiments, the system can be configured to perform a cartridge check as depicted in C1-1. If the system is to perform a cartridge check, the system can be configured to first determine whether a cartridge with concentrated bath fluid is installed in the system at block 112B. If the system determines that a cartridge with concentrated bath fluid is not installed, the system can be configured to determine whether a cartridge with concentrated disinfection fluid is installed at block 113B. If the system determines that a cartridge with concentrated disinfection fluid is not installed, the system control board can be configured to instruct an operator to insert a bath fluid cartridge and/or disinfection cartridge at block 114B.

Once an operator inserts a bath fluid cartridge, the system can then again determine whether the cartridge with concentrated bath fluid is installed properly at block 112B. If the system determines that a cartridge with concentrated disinfection fluid is installed, the system can then be configured to dispose the disinfection cartridge at block C4-1, details of which are to be described later. In such case, once the disinfection cartridge disposal is performed, the system can then be configured to again determine whether a cartridge with concentrated bath fluid is installed at block 112B.

If the system determines that a cartridge with concentrated bath fluid is installed, the system can be configured to perform a bath fluid preparation at block C2/C3, details of which are described below. The system can then be configured to determine whether the bath fluid preparation was successful at block 120B. If the system determines that the bath fluid preparation was not successful, the operator may run a system diagnostics and tools process to remove the cause of fluid preparation failure at block 125B. Based on such input from an operator, the system can be configured to perform diagnostics and determine whether the diagnostics and tools procedure was successful at block 124B. If the system determines that the diagnostics and tools procedure was not successful, the operator can be prompted to initiate a safety procedure and remove the patient or infant from the device at block 126B. If the system determines that the diagnostics and tools procedure was successful, the system can be configured to drain the fluid from the system into a wastewater tank at block 119B. Once the fluid is drained into the wastewater tank at block 119B the system can then be configured to perform a cartridge check at block C1-1 as described herein.

If the system determines that the bath fluid preparation was successful at block 120B, the system can be configured to distribute bath fluid from the fluid preparation system to a manifold at block 121B. Then, in some embodiments, the system can be configured to determine whether the bath fluid temperature is suitable at block 122B. If the system determines that the bath fluid temperature is suitable, for example at or near 37 C, the system can be configured to determine whether to use a rinser at block 128B. If the system determines to use a rinser, the system can then be configured to distribute bath fluid from the manifold to the rinser at block 127B. Once the bath fluid is distributed from the manifold to the rinser the bath fluid can then again be distributed from the fluid preparation system to the manifold at block 121B. If the system determines not to use a rinser at block 128B the system can be configured to distribute bath fluid into the bath without use of a rinser through a laminar nozzle at block 129B.

In certain embodiments, if the system determines that the bath fluid temperature is not suitable at block 122B, the system can be configured to prompt an operator to run a systems and diagnostics and tools procedure at block 123B. The system can be configured to determine whether the diagnostics and tools procedure was successful at block 118B. If the system determines that the diagnostics and tools procedure was not successful, the system can be configured to prompt the operator to initiate a safety procedure. In some embodiments, the operator can then initiate a safety procedure and remove the patient or infant from the device at block 109B.

If the system determines that the diagnostics and tools procedure was successful at block 118B, the system can be configured to determine whether to flush the system at 117B. If the system determines not to flush the system, the system can then be configured to determine once again if the bath fluid temperature is suitable at block 122B. If the system determines to flush the system at block 117B, fluid from the system is drained into a wastewater tank at block 116B. Once the fluid is drained, the operator may then use the control board to confirm whether to retry fluid preparation at block 115B. If the operator confirms to retry fluid preparation, the system can then again be configured to perform a bath fluid preparation procedure at block C2/C3.

Figure 21:
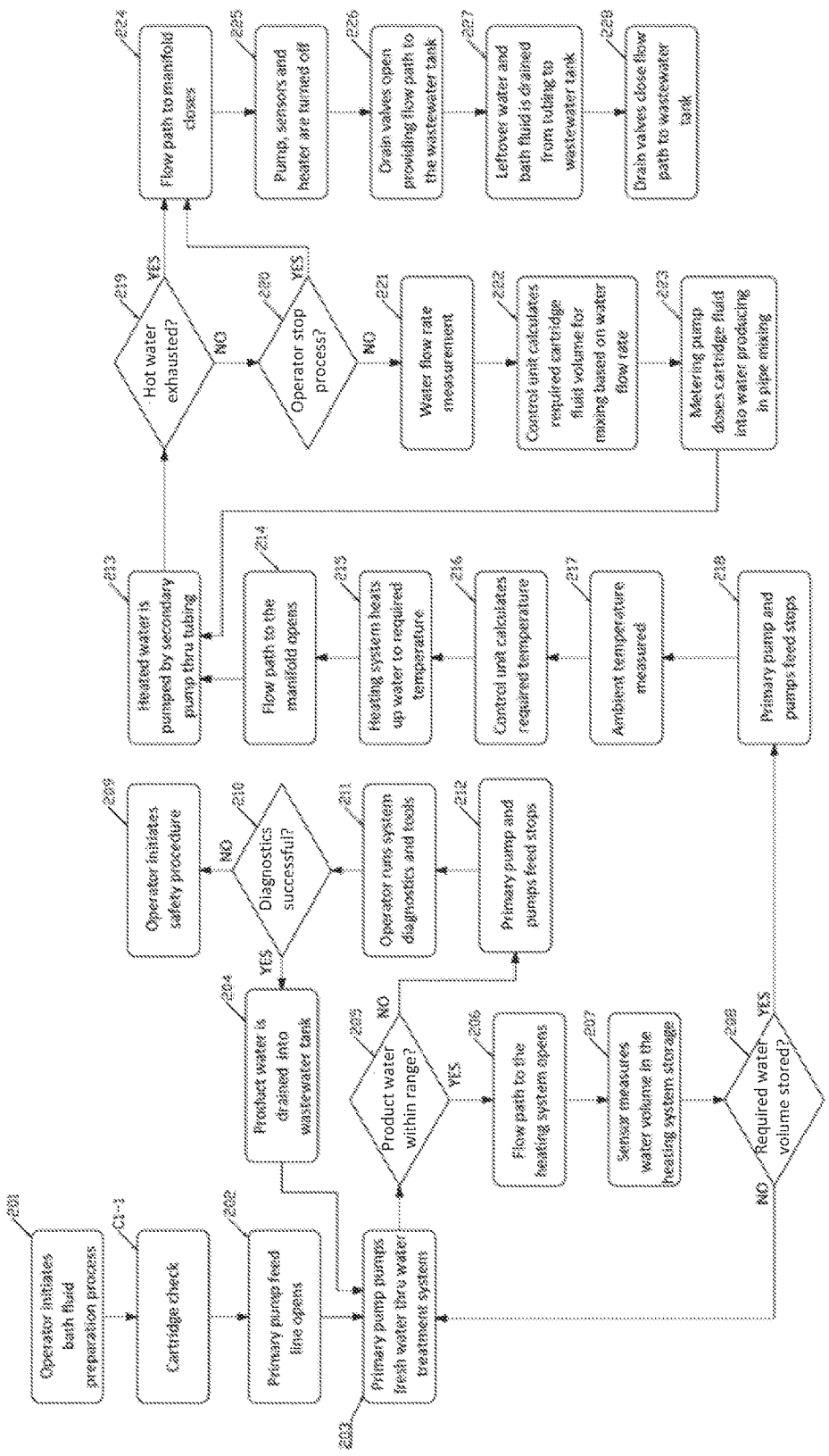
FIG. 21 is a block diagram depicting one or more embodiments of preparing bath fluid of an amniotic bath incubator system for premature infants.

Bath Fluid Preparation—Internal Water Treatment System, Internal Water Supply, and/or Internal Heater FIG. 21 is a block diagram depicting one or more embodiments of preparing bath fluid of an amniotic bath incubator system for premature infants. More specifically, FIG. 21 depicts an embodiment in which the amniotic bath incubator system comprises an internal water treatment system, an internal water supply, and/or an internal heater.

In some embodiments, an operator can initiate a bath fluid preparation process at block 201. Once the operator initiates a bath fluid preparation process, the system can be configured to perform a cartridge check at block C1-1. Additional details about the cartridge check are discussed above in relation to FIG. 20. Once the cartridge check is performed, the system can be configured to open a primary pump feedline at block 202. Once the primary pump feedline is opened, the system can be configured to instruct the primary pump to pump fresh water through the water treatment system at block 203.

The system can be configured to determine whether the product water comprises one or more acceptable characteristics. For example the system can be configured to determine whether the product water comprises an acceptable level of conductivity, resistivity, total dissolved solids (TDS) level, pH, or the like at block 205. If the system determines that all necessary characteristics of the product water are not within a permitted range, the system can be configured to stop the primary pump at block 212. In certain embodiments, the primary pump and the pump feed can then be configured to stop at block 212.

Once the primary pump and/or pump feed is stopped, the operator may run a system diagnostics and tools procedure at block 211. The system can then determine whether the diagnostics and tools procedure was successful at block 210. If the system determines that the diagnostics and tools procedure was not successful, the operator may initiate a safety procedure at 209. However, if the system determines that the diagnostics and tools procedure was successful at block 210, the system can be configured to drain the product water into the wastewater tank at 204. In some embodiments, the system can then again be configured to initiate pumping fresh water through the water treatment system by instructing the primary pump to pump fresh water.

If the system determines that the product water comprises characteristics within a permitted range at block 205, the system can be configured to open a flow path to the heating system at block 206. In certain embodiments, one or more sensors of the system can then measure the water volume in the heating system storage tank at block 207. Once the sensor measures the water volume in the heating system storage, the system can be configured to determine whether the required water volume is stored into the heating system at block 208. If the system determines that the required water volume is not stored into the heating system, the system can be configured to instruct the primary pump to pump fresh water through the water treatment system again at block 203.

If the system determines that the required water volume is stored in the heating system at block 208, the system can be configured to instruct the primary pump and/or pump feed to stop at block 218. In certain embodiments, one or more temperature sensors of the system can then be configured to measure the ambient temperature of the heated product water at block 217. A control unit of the system, in certain embodiments, can then be configured to determine a required temperature of the product water at block 216. Based on such calculation, the heating system can then be configured to heat the water to the required temperature at block 215. Once the water reaches the required temperature, the flow path to the manifold can be configured to open at block 214. Then, the heated water can be pumped by a secondary pump through a tubing at block 213.

The system can be configured to determine whether the hot water supply has been exhausted at block 219. Even if the system determines that the hot water supply has not been exhausted, the operator may decide to stop the fluid preparation process at block 220. If the operator does not stop the fluid preparation process, the system can be configured to measure the water flow rate at block 221. In some embodiments, a control unit of the system can then calculate the required cartridge fluid volume for mixing based on the water flow rate at block 222. In certain embodiments, a metering pump of the system can then be configured to dose the right amount of cartridge fluid into the water producing and pipe mixing at block 223. In certain embodiments, the water mixed with the correct amount of cartridge fluid is then mixed together with the heated water at 213.

If the operator decides to stop the fluid preparation process at block 220 and/or if the system determines that the hot water supply has been exhausted at block 219, the system can be configured to close the flow path of the product water to the manifold at block 224. In some embodiments, the pump sensors and/or heater of the system are then turned off at block 225. In certain embodiments, one or more drain valves of the system can then be opened at block 226, providing a flow path to the wastewater tank. In certain embodiments, the leftover water and bath fluid is then drained from the tubing to the wastewater tank at block 227. Once all the leftover water and bath fluid is drained, the system can be configured to close the drain valves to close flow path to the wastewater tank at block 228.

Bath Fluid Preparation—Central Water Treatment System with Heater

Figure 22:
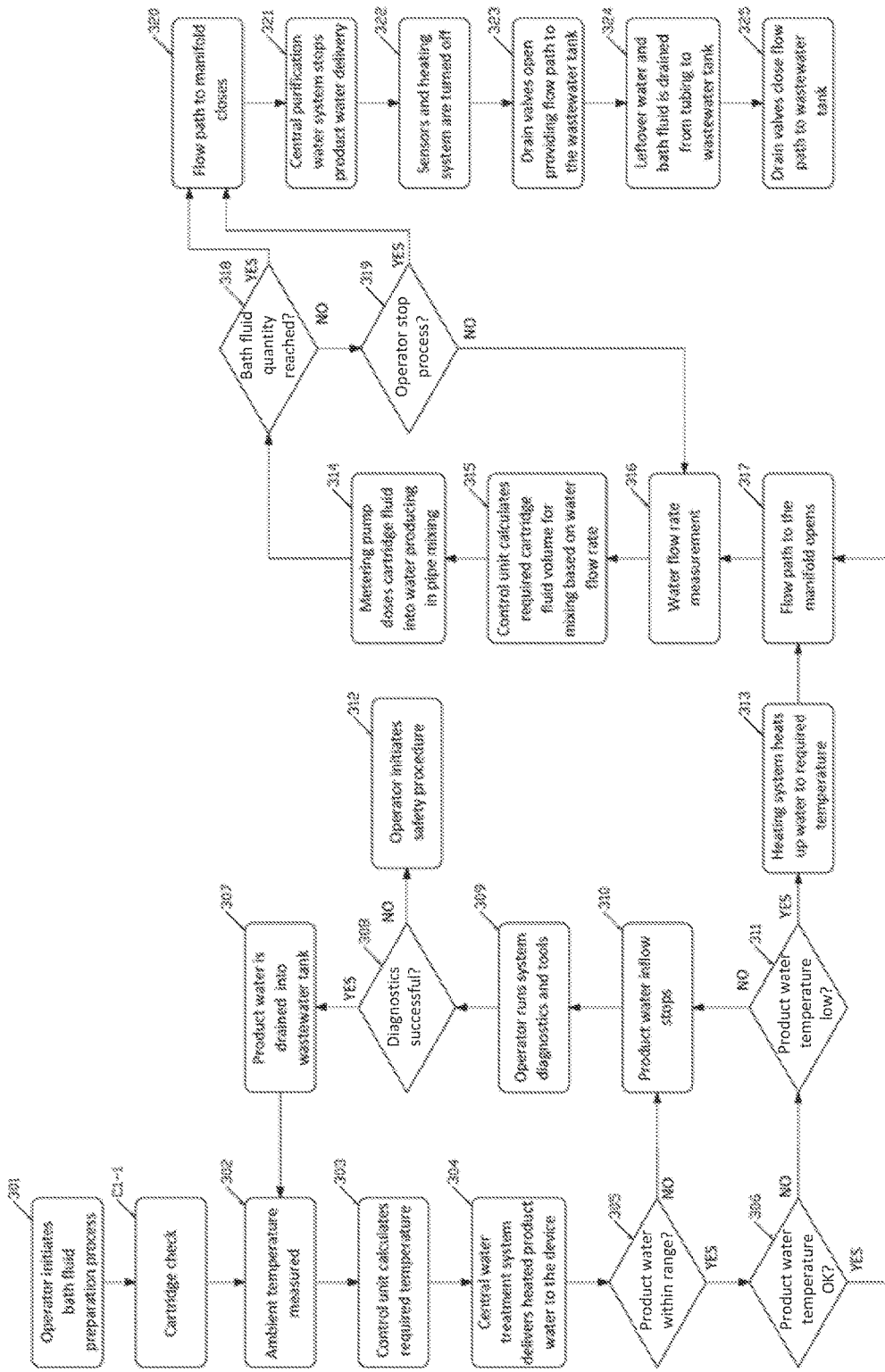
FIG. 22 is a block diagram depicting one or more embodiments of preparing bath fluid of an amniotic bath incubator system for premature infants.

FIG. 22 is a block diagram depicting one or more embodiments of preparing bath fluid of an amniotic bath incubator system for premature infants. More specifically, FIG. 22 depicts an embodiment of preparing bath fluid for an amniotic bath incubator in which the incubator comprises a central water treatment system with a heater.

In some embodiments, an operator may initiate a bath fluid preparation process at block 301. After receiving instructions from an operator to begin the bath fluid preparation process, the system can be configured to perform a cartridge check at block C1-1, details of which are discussed above. After performing the cartridge check, one or more temperature sensors of the system can be configured to detect or measure the ambient temperature of the bath fluid at block 302. In some embodiments, the control unit can be configured to calculate a required temperature at block 303. In certain embodiments, the central water treatment system can then be configured to deliver heated product water to the device at block 304.

The system can be configured to determine whether the product water comprises one or more acceptable characteristics at block 305. For example, the system can be configured to determine whether the product water's conductivity, resistivity, and/or TDS levels are within a permitted range at block 305. If one or more monitoring sensors of the system determine that the product water's conductivity, resistivity, and/or TDS levels are not within the permitted range, the system can be configured to stop the product water inflow at block 310.

Once the product water inflow is stopped, the operator may run a system diagnostics and tools procedure at block 309. After the system diagnostics and tools procedure is performed, the system can be configured to determine whether the diagnostics and tools procedure was successful at block 308. If the system determines that the diagnostics and tools procedure was not successful, the system can prompt the operator and the operator may perform a safety procedure at block 312. If the system determines that the diagnostics and tools procedure was successful, the system can be configured to drain the product water into a wastewater tank at block 307. Once the product water is drained, the system can be configured to return to block 302 to restart the process.

Returning to block 305, if the system determines that the product water conductivity, resistivity, and/or TDS levels are within a permitted range as detected by one or more monitoring sensors of the system, the system can be configured to determine whether the product water temperature is suitable at block 306. If the product water temperature is not suitable, the system can be configured to determine if the product water temperature is below a suitable range at block 311. If the product water temperature is above a suitable level, the system can be configured to stop the product water inflow at block 310. However if the product water temperature is below a suitable level, the heating system can be configured to heat the water to the required temperature at block 313. After heating to a required temperature, a flow path to the manifold can be configured to be opened at block 317.

Similarly, if the product water temperature was determined to be suitable at block 306 the system can be configured to automatically open a flow path to the manifold at block 317. In certain embodiments, once the flow path to the manifold is opened, the system can be configured to measure the water flow rate at block 316. In certain embodiments, a control unit is configured to calculate a required cartridge fluid volume for mixing based on the water flow rate at block 315.

In certain embodiments, a metering pump is configured to dose a necessary amount of cartridge fluid into the water producing and pipe mixing at block 314. After the pipe mixing is performed, the system can be configured to determine whether the required bath fluid quantity is reached at block 318. If the system determines that a required bath fluid quantity is not reached, the system can then prompt an operator whether the operator would like to stop the fluid preparation process at 319. If the operator decides not to stop the fluid preparation process, the system can continue to measure the water flow rate at 316 and continue with the fluid preparation process.

However, if the operator decides to stop the fluid preparation process at 319 and/or if the system determines that the required bath fluid quantity is reached at block 318, the system can be configured to close the flow path to the manifold at block 320. In some embodiments, once the flow path to the manifold is closed, a central purification water system can be configured to stop product water delivery at block 321. Once the product water delivery is stopped, one or more sensors and/or heating systems can be configured to be turned off at block 322. In some embodiments, the drain valves can be configured to be opened, providing a flow path to the wastewater tank at block 323. In certain embodiments, the leftover water and bath fluid is then drained from the tubing to the wastewater tank at block 324. Once all the leftover water and bath fluid is drained, the system can be configured to close the drain valves and flow path to the wastewater tank at block 325.

Disinfection

Figure 23:
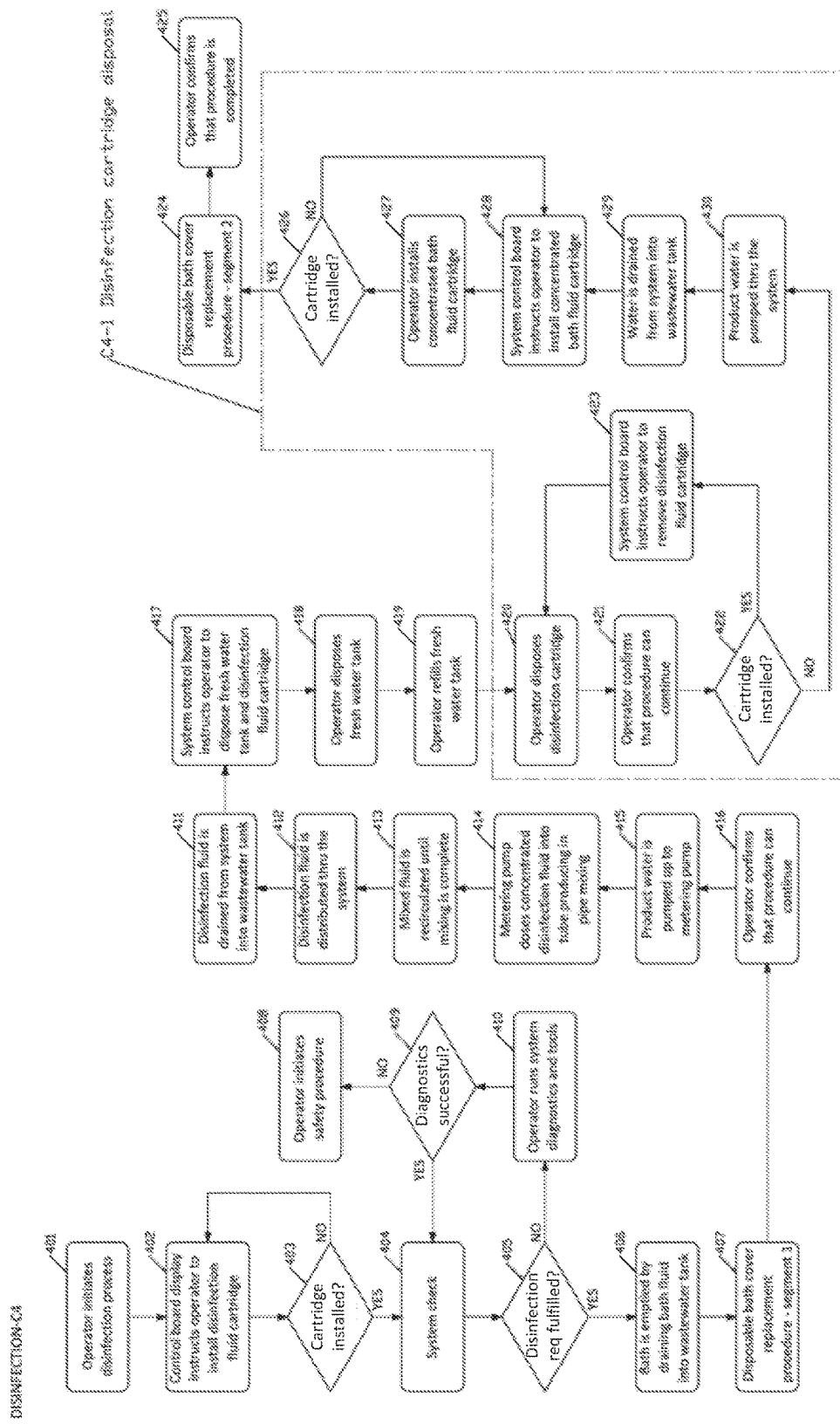
FIG. 23 is a block diagram depicting one or more embodiments of disinfecting an amniotic bath incubator system for premature infants.

FIG. 23 is a block diagram depicting one or more embodiments of disinfecting an amniotic bath incubator system for premature infants.

In some embodiments, an operator can initiate a disinfection process at block 401. Once the operator initiates a disinfection process, the control board of the system can be configured to display instructions to the operator to install a disinfection fluid cartridge at block 402. The operator can then install a disinfection fluid cartridge. In some embodiments, the system can then be configured to determine whether a cartridge with concentrated disinfection fluid is installed at block 403. If the system determines that a cartridge with concentrated disinfection fluid is not installed, the control board display of the system can be configured to again instruct the operator to install a disinfection fluid cartridge at block 402.

If the system determines that a cartridge with concentrated disinfection fluid is installed, the system can be configured to perform a system check at block 404. In performing the system check, the system can be configured to determine whether all the requirements for disinfection are fulfilled at block 405. If the system determines that not all of the requirements for disinfection are fulfilled, the system can prompt an operator and the operator can decide to run a system diagnostics and tools procedure at block 410. In some embodiments, the system can determine whether the diagnostics and tools procedure was successful at block 409. If the system determines that the diagnostics and tools procedure was not successful, the operator can initiate a safety procedure at block 408. However if the system determines that the diagnostics and tools procedure was successful, the system can be configured to then again perform the system check at block 404.

If the system determines that all the requirements for disinfection are fulfilled, then the system can be configured to empty the amniotic bath by draining bath fluid into a wastewater tank of the system at block 406. In some embodiments, the system can be configured to perform one or more processes of a disposable bath cover replacement procedure. For example, the system can be configured to perform one or more processes of segment 1 of a disposable bath cover replacement procedure at block 407.

In some embodiments, the system prompts the operator to confirm whether the procedure can continue at block 416, for example after completion of one or more processes of the disposable bath cover replacement procedure. If the operator confirms that the procedure can continue at block 416, the system can be configured to pump product water up to the metering pump at block 415. In some embodiments, the metering pump can be configured to dose a necessary amount of concentrated disinfection fluid into the tube, producing in pipe mixing at block 414. In other embodiments, the concentrated disinfection fluid is mixed with fresh water in a batch process. The mixed fluid can then be recirculated until the mixing is complete at block 413. Once the mixing is complete, the disinfection fluid can be distributed through the system at block 412. The disinfection fluid can then be configured to be drained from the system into the wastewater tank at block 411.

After the disinfection fluid is distributed through the system and is consequently drained from the system into the wastewater tank, the system control board can be configured to instruct the operator to dispose the contents of the fresh water tank and also the disinfection fluid cartridge at block 417. The operator can dispose the contents of the fresh water tank at block 418 and then refill the fresh water tank with fresh water at block 419.

In some embodiments, the system can then be configured to perform a disinfection cartridge disposal by performing one or more processes depicted within the box numbered C4-1. More specifically, the operator may dispose the disinfection cartridge at block 420. In some embodiments, the system can then prompt the operator to confirm whether the procedure can continue. Once the operator confirms that the procedure can continue after disposing the disinfection cartridge at block 421, in some embodiments, the system can be configured to perform a check to determine whether the cartridge with concentrated disinfection fluid is still installed in the system at block 422. If the system determines that a disinfection cartridge is still installed in the system, the system control board can be configured to instruct the operator to remove the disinfection fluid cartridge at block 423. In some embodiments, the control board can refer to a digital touchscreen display and/or physical button control board. The operator may then dispose the disinfection cartridge at block 420.

If the system determines that a cartridge with concentrated disinfection fluid is no longer installed at block 422, the system can be configured to pump product water through the system at block 430. In some embodiments, water from the system can be drained into the wastewater tank at block 429. In certain embodiments, the system control board can be configured to instruct the operator to install a concentrated bath fluid cartridge at block 428. The operator may install a concentrated bath fluid cartridge at block 427.

In some embodiments, the system can be configured to perform a check to determine whether a cartridge with concentrated bath fluid was installed at block 426. If the system determines that a cartridge with concentrated bath fluid is not installed, the system control board can again be configured to instruct the operator to install a concentrated bath fluid cartridge at block 428. However, if the system determines that a cartridge with concentrated bath fluid is installed, the system can be configured to perform one or more processes of segment 2 of the disposable bath cover replacement procedure at block 424. After performing one or more processes of segment two of the disposable bath cover replacement procedure, the operator may confirm that the procedure is completed at block 425.

Disposable Bath Cover Replacement Procedure

Figure 24:
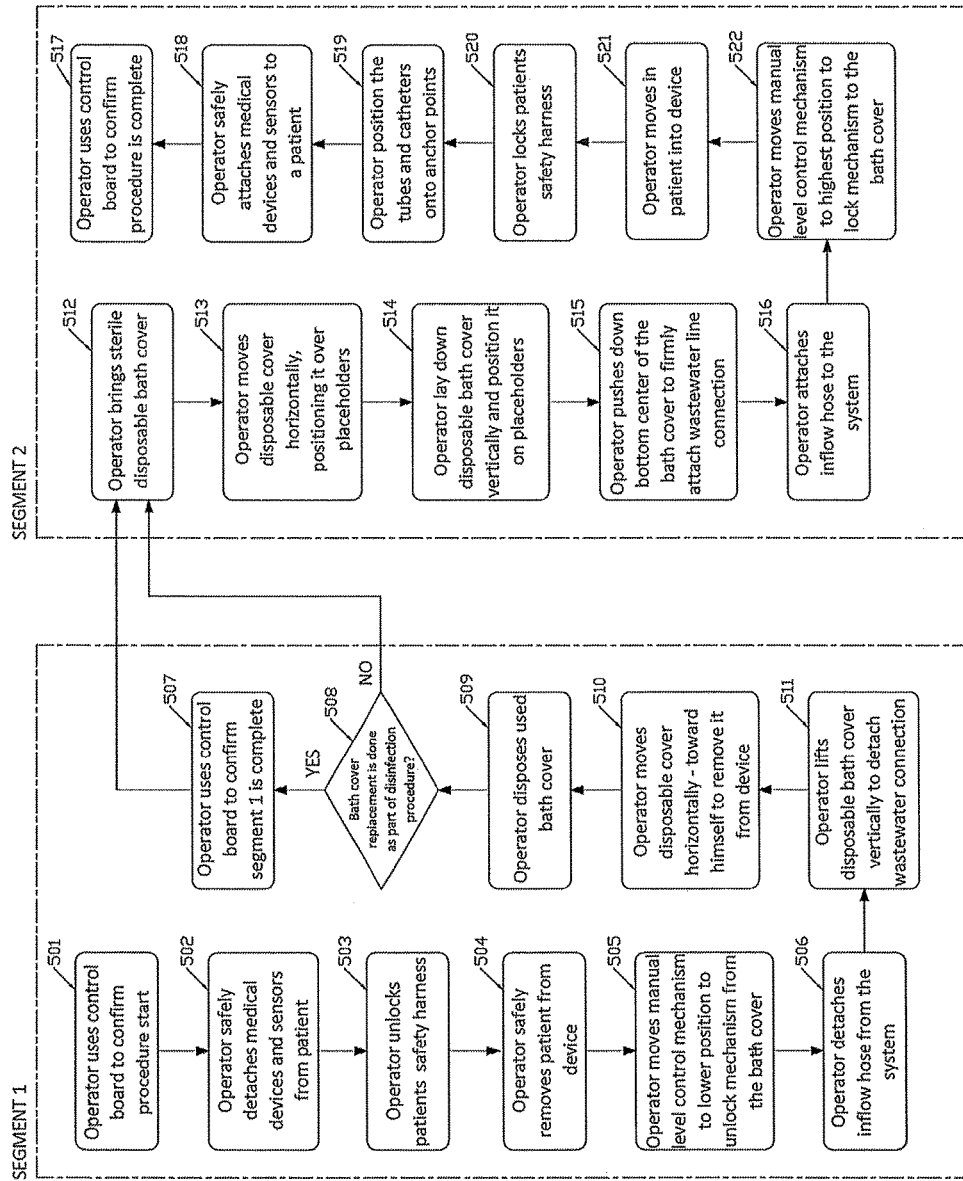
FIG. 24 is a block diagram depicting one or more embodiments of replacing a bath cover of an amniotic bath incubator system for premature infants.

FIG. 24 is a block diagram depicting one or more embodiments of replacing a bath cover of an amniotic bath incubator system for premature infants. In some embodiments, a disposable bath cover replacement procedure can comprise of one or more processes, which can be categorized into two segments denoted as segments 1 and 2 herein.

In some embodiments, an operator may use the control board of the system to confirm start of a disposable bath replacement procedure at block 501. The operator may then safely detach one or more medical devices and/or sensors from the patient or infant at block 502. The operator may also unlock a safety harness attached to the patient or infant at block 503. Once the safety harness and/or one more medical devices or sensors are all removed from the patient or infant, the operator may safely remove the patient or infant from the device at block 504.

In some embodiments, once the patient or infant is safely removed, the operator may move a level control mechanism to lower the position of the system at block 505. For example, the level control mechanism can be automatic or manual. The level control mechanism can be configured to lower the position of the system for easy removal of the bath cover after unlocking the mechanism by the operator.

In some embodiments, the operator may detach an inflow hose from the system at block 506. The operator may lift the disposable bath cover vertically, horizontally, and/or diagonally to detach from the wastewater connection at block 511. In some embodiments, the operator may move the disposable cover horizontally, vertically, and/or diagonally toward or from him or herself to remove the disposable cover from the device at block 510. The operator may then dispose the used bath cover at block 509.

The system can be configured to determine whether the bath cover replacement procedure is being performed as part of a disinfection procedure at block 508. If the bath cover replacement procedure is being performed as part of a disinfection procedure, the operator may use the control board to confirm to the system that segment 1 of the disposable bath cover replacement procedure is completed at block 507. The processes described in blocks 501 through 511 can be categorized as being part of segment 1 of the disposable bath cover replacement procedure.

If the operator uses the control board to confirm that segment 1 is complete as depicted in block 507 and/or if the bath cover replacement procedure was not performed as part of disinfection procedure as determined in block 508, the operator may bring a new sterile disposable bath cover at block 512, beginning segment 2 of the disposable bath cover replacement procedure. In order to attach the new sterile disposable bath cover, the operator may move the disposable cover horizontally, vertically, and/or diagonally to position the disposable cover over the placeholders at block 513. The operator may then lay down the disposable bath cover vertically, horizontally, and/or diagonally to position the disposable bath cover on placeholders at block 514. The operator may then push down the bottom center and/or rim or one or more other portions of the bath cover to firmly attach the wastewater line connection to the disposable cover at block 515. The operator may also attach an inflow hose to the system at block 516.

Once the inflow hose, wastewater line connection, and/or disposable bath cover is attached to the system, the operator may move a level control mechanism of the system at block 522. For example, the operator may utilize a manual and/or automatic level control mechanism of the system to its highest position to lock the mechanism to the bath cover at block 522.

In some embodiments, the operator may then move in the patient or infant into the device at block 521. Once the patient or infant is positioned within the amniotic bath, the operator may lock the patient or infant into the safety harness at block 520 in order to ensure that the infant is not accidentally submerged in the amniotic fluid. The operator may also, in some embodiments, position one or more tubes and catheters onto anchor points on one or more bridges above the bath at block 519. The operator may, in some embodiments, safely attach one or more medical devices and/or sensors, such as one or more tubes or catheters, to the patient or infant at block 518. In certain embodiments, the operator may use the control board to confirm that segment 2 of the disposable bath cover replacement procedure is completed at block 517.

Wastewater Tank Discharge

Figure 25A:
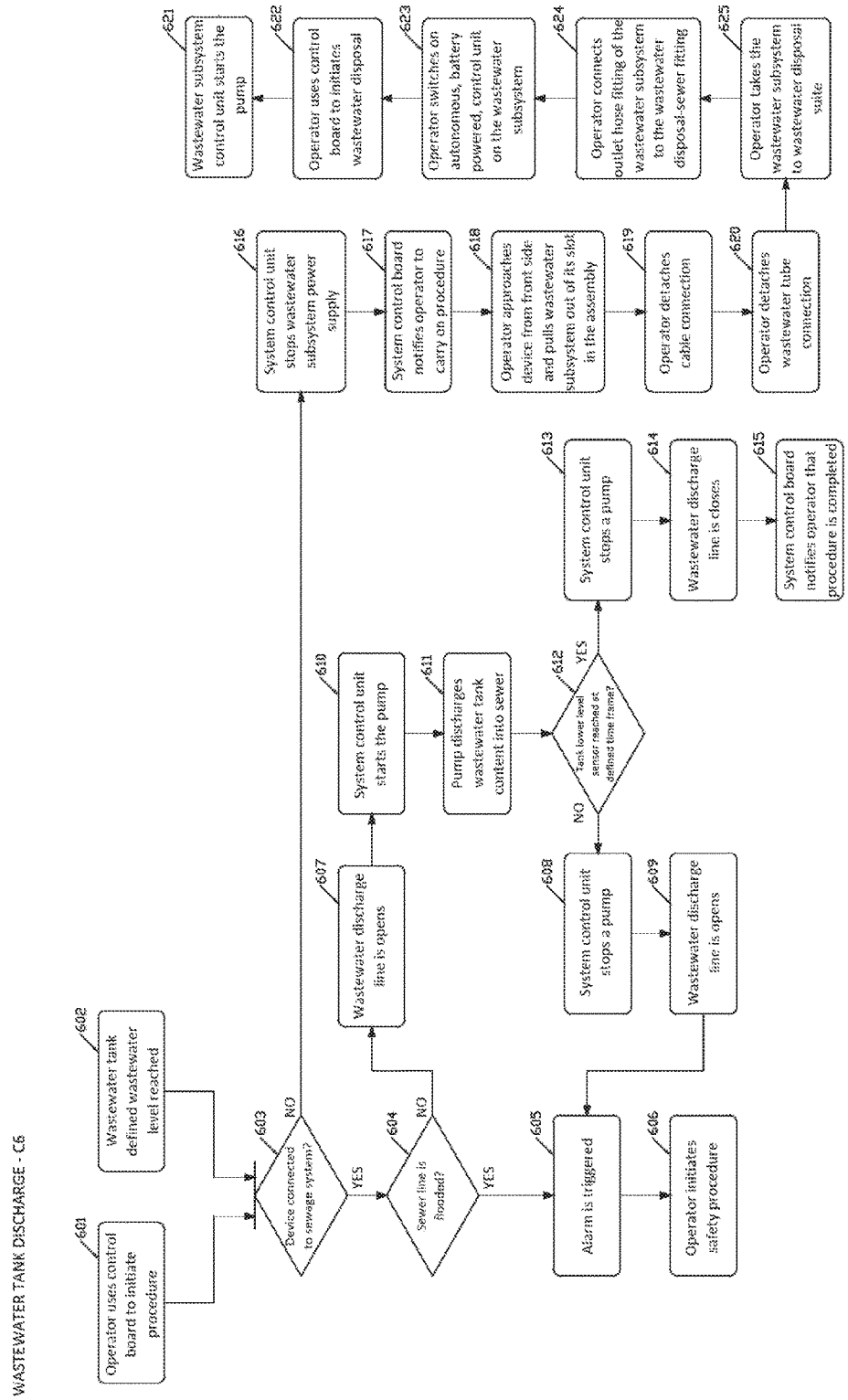
FIGS. 25A-B are block diagrams depicting one or more embodiments of discharging a wastewater tank of an amniotic bath incubator system for premature infants.
Figure 25B:
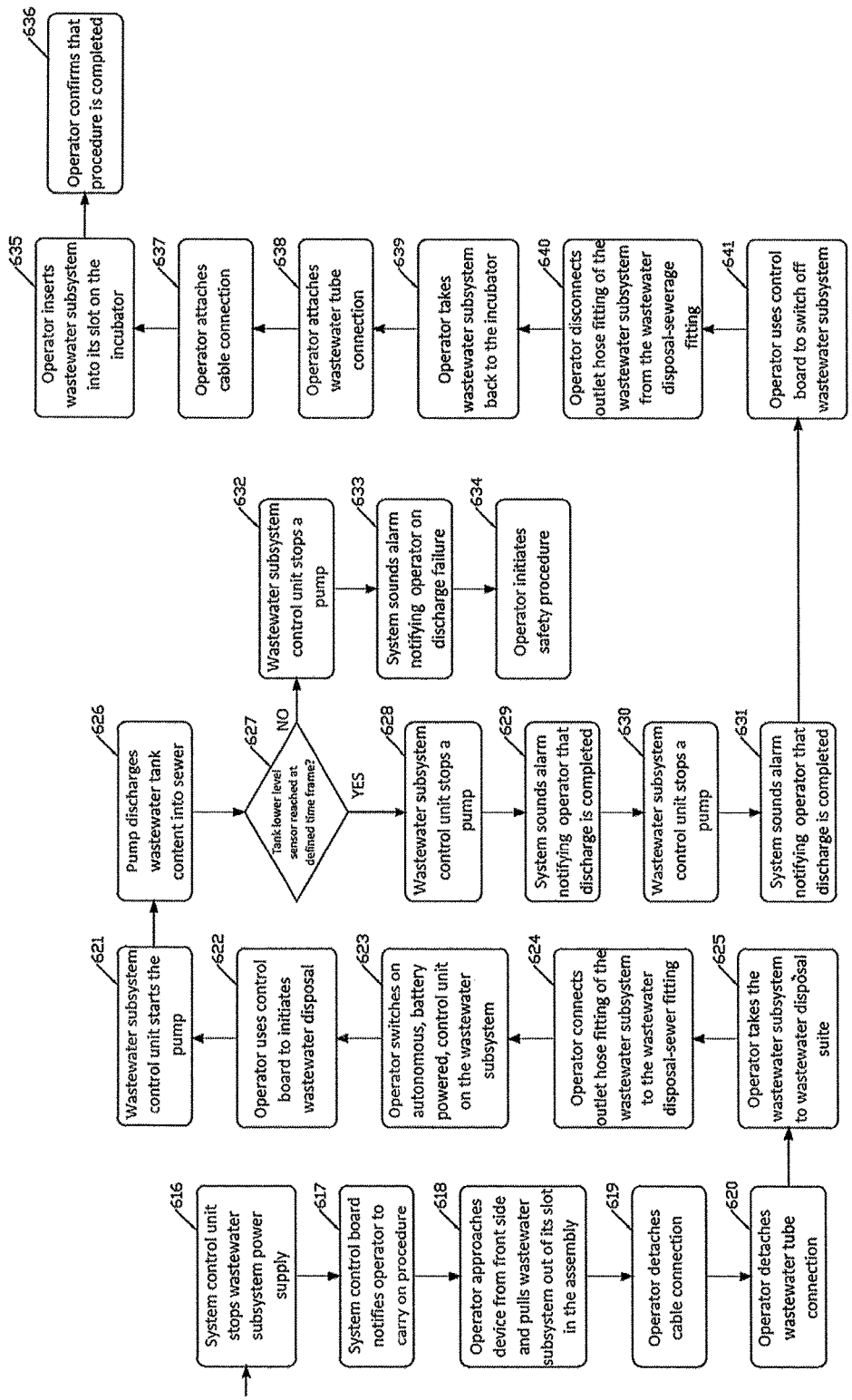

FIGS. 25A-B are block diagrams depicting one or more embodiments of discharging a wastewater tank of an amniotic bath incubator system for premature infants. In some embodiments, an operator can use a control board to initiate the wastewater tank discharge procedure at block 601. In certain embodiments, even without operator initiation, the system can be configured to determine whether a predefined wastewater level has been reached in the wastewater tank and initiate the wastewater tank discharge procedure automatically at block 602.

Once the wastewater tank discharge process has been initiated, the system can be configured to determine whether the system or device is connected to a sewage system at block 603. If the system or device is connected to a sewage system, the system can be configured to determine whether the sewer line is flooded at block 604. If the sewer line is not flooded, the system can be configured to open the wastewater discharge line at block 607. In some embodiments, a system control unit is then configured to start one or more pumps for the discharge process at block 610. In some embodiments, the one or more pumps then discharge the wastewater tank contents into the sewer at block 611.

In some embodiments, the system can be configured to determine whether a lower level sensor within the wastewater tank is reached at a defined timeframe at block 612. If the system determines that the tank lower level sensor is reached at a defined timeframe, the system control unit can be configured to stop the one or more pumps at block 608. Once the one or more pumps are stopped, the wastewater discharge line can be configured to be opened at block 609, triggering an alarm at block 605. Once the alarm is triggered at block 605, in some embodiments, the system can be configured to prompt an operator and an operator may initiate a safety procedure at block 606.

If the system determines that a tank lower level sensor is reached at a defined timeframe at block 612, the system control unit can be configured to stop one or more pumps at block 613. In some embodiments, the wastewater discharge line can be closed at block 614. In certain embodiments, the system control board can be configured to notify the operator that the wastewater tank discharge procedure is completed at block 615.

If the system determines that the system or device is not connected to a sewage system at block 603, the system control unit can be configured to stop power supply to the wastewater subsystem at block 616. In certain embodiments, the system control board can be configured to notify the operator to continue the procedure at block 617. The operator may approach the device or system from a front, side, or backside and pull the wastewater subsystem out of its slot in the assembly at block 618. The operator may detach a cable connection to the wastewater subsystem at block 619. The operator may also detach a wastewater tube connection at block 620.

The operator may take or roll the wastewater subsystem to a wastewater disposal suite at block 625. The operator may connect an outlet hose fitting of the wastewater subsystem to the wastewater disposal sewer fitting at block 624. In some embodiments, the wastewater subsystem can comprise a powered control unit. As such, in some embodiments, the operator may switch on an autonomous battery powered control unit on the wastewater subsystem at block 623. The operator may use the control board to initiate wastewater disposal at block 622.

Upon instruction from the operator, the wastewater subsystem control unit may be configured to power and/or start one or more pumps for discharge of the wastewater subsystem at block 621. The pump may be configured to discharge wastewater tank content into the sewer at block 626. The system in some embodiments can be configured to determine whether the tank lower level sensor is reached at a defined timeframe at block 627. If the system determines that the tank lower level sensor is not reached at the defined timeframe, the wastewater subsystem control unit can be configured to stop the one or more for discharge at block 632. The system can then be configured to sound one or more alarms notifying an operator of the discharge failure at block 633. The operator may initiate a safety procedure at block 634.

However, if the tank lower level sensor is reached after a defined timeframe, the wastewater subsystem control unit can be configured to stop the one or more pumps for discharge at block 628. The system in some embodiments can be configured to sound one or more alarms notifying the operator that the discharge process has been completed at block 629. Subsequently and/or at the same time, the wastewater subsystem control unit can be configured to stop the operation of the one or more pumps at block 630. In some embodiments, the system can be configured to sound one or more alarms notifying the operator that the discharge has been completed at block 631.

The operator may use the control board to switch off the wastewater discharge subsystem at block 641 in some embodiments. The operator may disconnect the outlet hose fitting of the wastewater subsystem from the wastewater disposal sewage fitting at block 640. The operator may then take or roll the wastewater subsystem back to the incubator at block 639. The operator may then attach the wastewater tube connection of the system or incubator to the wastewater subsystem at block 638. The operator may also attach a cable connection of the system to the wastewater subsystem at block 637. The operator may insert the wastewater subsystem into its slot in the incubator or device or system at block 635. The operator may confirm, in some embodiments, that the wastewater tank discharge process has been completed at block 636.

Fresh Water Tank Replacement and/or Fill Process

Figure 26B:
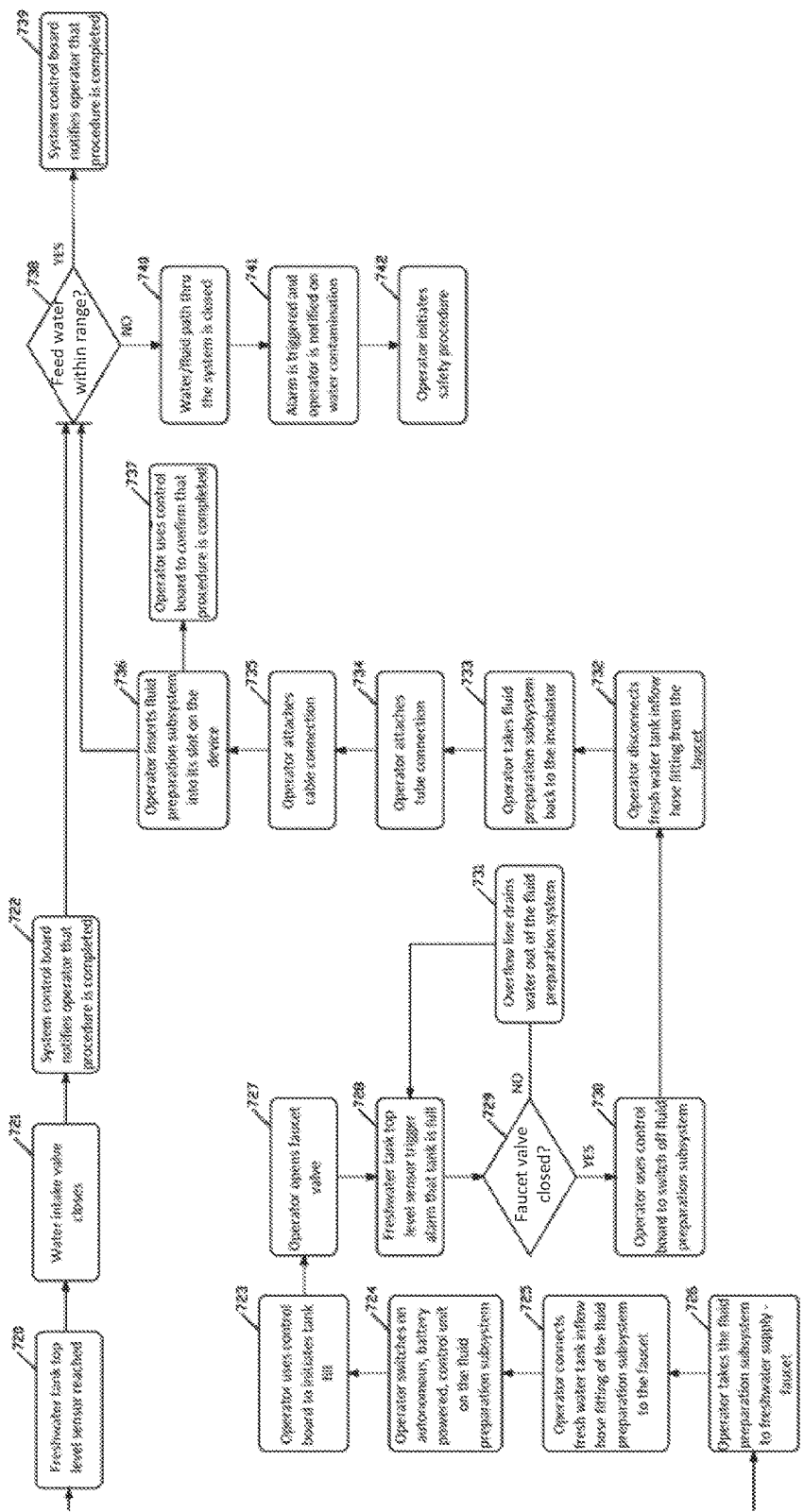

FIGS. 26A-B are block diagrams depicting one or more embodiments of replacing and/or filling a fresh water tank of an amniotic bath incubator system for premature infants. In some embodiments, an operator may use a control board of the system to initiate the fresh water tank replacement and fill process at block 701. In certain embodiments, even without instruction from an operator, the system can be configured to automatically initiate a fresh water tank replacement and fill process upon determining that the fresh water tank is empty at block 702. In some embodiments, the system can be configured to initiate a fresh water tank replacement and fill process according to a scheduled disposal time. As such, in some embodiments, when a scheduled disposal time is reached, the fresh water tank replacement and fill process can be automatically initiated at block 703.

Once the fresh water tank replacement and fill process has been initiated, the system control unit can be configured to turn off the power supply of the fluid preparation subsystem at block 704. In certain embodiments, the system control board can be configured to notify the operator to continue the procedure at block 705. The operator may approach the device or system from the front, side, or back and pull the fluid preparation subsystem out of its slot in the device at block 706. The operator may detach one or more cable connections connecting the fluid preparation subsystem with the amniotic bath incubator at block 707. The operator may also detach one or more tube connections connecting the fluid preparation subsystem and the amniotic bath incubator at block 708.

The system can be configured to determine whether to dispose the used fresh water tank and/or contents thereof at block 712. If the system determines to dispose the used fresh water tank and/or its contents at block 712, the operator may remove the fresh water tank from its slot in the subsystem at block 711. The operator may dispose the used fresh water tank and/or its contents at block 710. The operator may then insert a new disposable fresh water tank in its slot in the subsystem at block 709. If the system determines not to dispose the fresh water tank at block 712, the system can be configured to determine whether the amniotic bath incubator or device or system is connected to water supply system at block 719.

If the device or system is connected to a water supply system, an operator may connect the fresh water tank to an inflow line at block 718. The operator may also attach one or more tube connections connecting the fresh water tank to the amniotic bath incubator at block 717. The operator may also attach one or more cable connections to the fresh water tank at block 716. The operator may also insert a fluid preparation subsystem into its slot in the device at block 715. In some embodiments, the operator may also use the control board to initiate filling of the fresh water tank at block 714.

Upon initiation of the fresh water tank fill by the operator, the system can be configured to open a water intake valve at block 713. After the fresh water tank is filled with fresh water, a sensor of the fresh water tank can be configured to determine whether the fresh water tank top level has been reached at block 720. If the fresh water tank top level sensor has been reached, the water intake valve can be configured to close at block 721. Once the water intake valve has been closed, the system control board can be configured to notify the operator that the procedure has been completed at block 722.

If the device is not connected to a water supply system as determined at block 719, the operator may take or roll the fluid preparation subsystem to a fresh water supply or a faucet at block 726. The operator may connect a fresh water tank inflow hose fitting of the fluid preparation subsystem to the faucet at block 725. In some embodiments, the fluid preparation subsystem comprises a powered control unit. As such, in some embodiments, the operator may switch on an autonomous battery powered control unit on the fluid preparation subsystem at block 724. The operator may use the control board to initiate tank fill at block 723.

In some embodiments, the operator may open a faucet valve at block 727. In certain embodiments, a fresh water tank top level sensor can be configured to determine whether the tank is full or not at block 728. If the fresh water tank top level sensor determines that the tank is full, the sensor can be configured to trigger an alarm that the tank is full at block 728. Once the alarm is triggered, the operator may be prompted to close the faucet valve at block 729. If the operator does not close the faucet valve, an overflow line can be configured to drain excess water out of the flow preparation system at block 731, returning the process back to block 728.

If the operator closes the faucet valve at block 729, the operator may use a control board to switch off the fluid preparation subsystem at block 730. The operator may disconnect the freshwater tank inflow hose fitting from the faucet at block 732. The operator may take the fluid preparation subsystem back to the incubator at block 733. In some embodiments, the operator may attach one or more tube connections to the fluid preparation subsystem at block 734. The operator may also attach one or more cable connections to the fluid preparation subsystem at block 735. The operator may then insert and lock the fluid preparation subsystem into its slot and the amniotic bath incubator at block 736.

In certain embodiments, the operator may use a control board to confirm that the fresh water tank replacement and fill process has been completed at block 737. In some embodiments, the system can then be configured to determine whether the conductivity, resistivity, and/or TDS monitoring sensors show that one or more characteristics of the fluid and the fluid preparation subsystem is within a predetermined range at block 738. If the system determines that the one or more characteristics of the fluid and the fluid preparation subsystem are within a predetermined range, the system control board can be configured to notify the operator that the procedure has been completed at block 739.

In some embodiments, if one or more characteristics of the fluid and the fluid preparation subsystem are not within a permitted range, the water or fluid path through the system can be configured to be automatically closed at block 740. In certain embodiments, an alarm can be configured to be triggered and notify an operator about contamination of the water system at block 741. In some embodiments, the operator can then initiate a safety procedure at block 742.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

The ranges disclosed herein also encompass any and all overlap, sub-ranges, and combinations thereof. Language such as "up to," "at least," "greater than," "less than," "between," and the like includes the number recited and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. Numbers preceded by a term such as "about" or "approximately" include the recited numbers. For example, "about 3 mm" includes "3 mm."

The headings provided herein, if any, are for convenience only and do not necessarily affect the scope or meaning of the devices and methods disclosed herein.

What is claimed is:

1. A neonatal incubator for an infant, the neonatal incubator comprising:
   an amniotic bath basin configured to hold synthetic amniotic fluid, wherein the synthetic amniotic fluid comprises a controlled concentration of one or more electrolytes and one or more minerals, wherein the synthetic amniotic fluid is produced by:
      installing a cartridge in the neonatal incubator, wherein the cartridge comprises concentrated synthetic amniotic fluid having the one or more electrolytes and the one or more minerals in a higher concentration than the controlled concentration; and
      mixing a controlled amount of the concentrated synthetic amniotic fluid with purified water to obtain the synthetic amniotic fluid having the controlled concentration of the one or more electrolytes and the one or more minerals;
   a purified water supply tank configured to provide the purified water for dissolving the one or more electrolytes and the one or more minerals of the cartridge;
   a fluid injection pump configured to control the mixing of the concentrated synthetic amniotic fluid with the purified water such that the controlled concentration of the one or more electrolytes and the one or more minerals can be adjusted based at least in part on one or more characteristics of an infant in the amniotic bath basin;
   a waste water removal tank configured to remove waste water from the amniotic bath basin;
   a seat configured to hold the infant in the amniotic bath basin; and
   a safety harness configured to maintain a position of the infant in the seat such that a head of the infant is maintained above a fluid level of the synthetic amniotic fluid.

2. The neonatal incubator of claim 1, further comprising one or more bridges above the amniotic bath basin and extending generally parallel to the fluid level of the synthetic amniotic fluid.

3. The neonatal incubator of claim 2, wherein the one or more bridges are configured to anchor a first end of one or more of a feeding tube, an oxygen tube, and an umbilical catheter above the synthetic amniotic fluid.

4. The neonatal incubator of claim 3, wherein a second end of one or more of the feeding tube, the oxygen tube, and the umbilical catheter is connected to the infant.

5. The neonatal incubator of claim 1, further comprising:
a temperature sensor configured to detect a temperature of the synthetic amniotic fluid; and
a heater configured to heat the synthetic amniotic fluid when the detected temperature is below a predetermined threshold value.

6. The neonatal incubator of claim 1, wherein the purified water supply tank and the waste water removal tank are removable from the neonatal incubator.

7. The neonatal incubator of claim 1, further comprising a contamination sensor configured to detect a contamination level of the synthetic amniotic fluid and cause removal of at least a portion of the synthetic amniotic fluid when the detected contamination level is above a predetermined level.

8. The neonatal incubator of claim 1, wherein the synthetic amniotic fluid further comprises one or more amino acids.

9. The neonatal incubator of claim 1, wherein the synthetic amniotic fluid further comprises one or more therapeutic agents configured to be absorbed by the infant.

10. The neonatal incubator of claim 1, wherein a pH level and osmolality of the synthetic amniotic fluid is modified according to growth of the infant by adjusting the controlled amount of the concentrated synthetic amniotic fluid mixed with the purified water.

11. The neonatal incubator of claim 1, wherein the synthetic amniotic fluid is further produced by detecting a condition of the neonatal incubator and determining the controlled amount of the concentrated synthetic amniotic fluid for mixing with the purified water based at least in part on the detected condition of the neonatal incubator.

12. The neonatal incubator of claim 1, wherein the one or more characteristics of the infant comprises one or more of a gestation age of the infant, size of the infant, or other medical indication of the infant.

13. A neonatal incubator for an infant, the neonatal incubator comprising:
an amniotic bath basin configured to hold synthetic amniotic fluid, wherein the synthetic amniotic fluid comprises a controlled concentration of one or more electrolytes and one or more minerals;
a purified water intake tube for receiving purified water;
a removable cartridge comprising concentrated synthetic amniotic fluid having the one or more electrolytes and the one or more minerals in a higher concentration than the controlled concentration, wherein a controlled amount of the concentrated synthetic amniotic fluid is mixed with the purified water to produce the synthetic amniotic fluid comprising the controlled concentration of the one or more electrolytes and the one or more minerals;
a fluid injection pump configured to control the mixing of the concentrated synthetic amniotic fluid with the purified water such that the controlled concentration of the one or more electrolytes and the one or more minerals can be adjusted based at least in part on one or more characteristics of an infant in the amniotic bath basin;
a waste water removal tube for removing waste water from the amniotic bath;
a seat configured to hold the infant in the amniotic bath basin;
a safety harness configured to maintain a position of the infant in the seat such that a head of the infant is maintained above a fluid level of the synthetic amniotic fluid; and
a bridge extending above the amniotic bath basin, wherein the bridge comprises an anchor for anchoring one end of an umbilical catheter above the synthetic amniotic fluid.

14. The neonatal incubator of claim 13, wherein the bridge is configured to further anchor a first end of a feeding tube above the synthetic amniotic fluid.

15. The neonatal incubator of claim 13, wherein a second end of the umbilical catheter is configured to be connected to the infant.

16. The neonatal incubator of claim 13, wherein the synthetic amniotic fluid further comprises one or more medicines configured to be absorbed by the infant, and wherein the cartridge further comprises the one or more medicines.

17. The neonatal incubator of claim 13, wherein the controlled amount of the concentrated synthetic amniotic fluid mixed with the purified water is determined based at least in part on a detected condition of the neonatal incubator to determine the controlled concentration of the one or more electrolytes and the one or more minerals in the synthetic amniotic fluid.

18. The neonatal incubator of claim 13, wherein the one or more characteristics of the infant comprises one or more of a gestation age of the infant, size of the infant, or other medical indication of the infant.

19. A method of providing care for a neonatal infant, the method comprising:
providing a neonatal incubator for the infant, wherein the neonatal incubator comprises an amniotic bath basin;
providing purified water to the neonatal incubator;
mixing a controlled amount of concentrated synthetic amniotic fluid from a cartridge with the purified water using a fluid injection pump to obtain a synthetic amniotic fluid with a controlled concentration of one or more electrolytes and one or more minerals, wherein the concentrated synthetic amniotic fluid in the cartridge comprises the one or more electrolytes and the one or more minerals in a higher concentration than the controlled concentration, wherein the controlled concentration of the one or more electrolytes and the one or more minerals is adjustable by controlling the fluid injection pump based at least in part on one or more characteristics of the infant;
placing an attachable basin cover over the amniotic bath basin, wherein the basin cover is sterile and disposable;
filling the amniotic bath basin at least partially with the synthetic amniotic fluid;
placing the infant in the amniotic bath basin at least partially filled with the synthetic amniotic fluid and attaching the infant to a safety harness, wherein the safety harness maintains a position of the infant such that a head of the infant is maintained above a fluid level of the synthetic amniotic fluid; and
periodically removing waste water from the amniotic bath basin.

20. The method of claim 19, further comprising:
detecting a temperature of the synthetic amniotic fluid; and
heating the synthetic amniotic fluid when the detected temperature is below a predetermined threshold value.

21. The method of claim 19, wherein the purified water is provided to the amniotic bath by removing a modular purified water tank from the neonatal incubator, adding purified water to the modular purified water tank, and reattaching the modular purified water tank to the neonatal incubator.

22. The method of claim 19, wherein the purified water is provided to the amniotic bath directly from a purified water source connected to the neonatal incubator.

23. The method of claim 19, further comprising attaching a first end of a feeding tube to the infant and attaching a second end of the feeding tube to a bridge.

24. The method of claim 19, further comprising administering one or more medicines to the infant by dissolving the one or more medicines in the synthetic amniotic fluid.

25. The method of claim 19, further comprising detecting a condition of the neonatal incubator and determining the controlled amount of the concentrated synthetic amniotic fluid for mixing with the purified water based at least in part on the detected condition of the neonatal incubator.

26. The method of claim 19, wherein the one or more characteristics of the infant comprises one or more of a gestation age of the infant, size of the infant, or other medical indication of the infant.

\* \* \* \* \*